(12) United States Patent
Sokolov et al.

(10) Patent No.: US 12,053,163 B2
(45) Date of Patent: Aug. 6, 2024

(54) DISPOSABLE CONTROLS, RE-USABLE DEVICES, AND THEIR METHODS OF USE

(71) Applicant: Spiro Robotics, Inc., Palo Alto, CA (US)

(72) Inventors: Dimitri Sokolov, Palo Alto, CA (US); Vladimir Nekhendzy, Palo Alto, CA (US); Thomas Ruegg, Vancouver (CA)

(73) Assignee: Spiro Robotics, Inc., Castro Valley, CA (US)

( * ) Notice: Subject to any disclaimer, the term of this patent is extended or adjusted under 35 U.S.C. 154(b) by 0 days.

(21) Appl. No.: 18/298,184

(22) Filed: Apr. 10, 2023

(65) Prior Publication Data

US 2024/0057859 A1    Feb. 22, 2024

Related U.S. Application Data

(60) Provisional application No. 63/329,449, filed on Apr. 10, 2022, provisional application No. 63/352,774, filed on Jun. 16, 2022.

(51) Int. Cl.
  *A61B 1/267* (2006.01)
  *A61B 1/00* (2006.01)
  *A61B 1/005* (2006.01)

(52) U.S. Cl.
  CPC .......... *A61B 1/267* (2013.01); *A61B 1/00042* (2022.02); *A61B 1/00103* (2013.01); *A61B 1/00128* (2013.01); *A61B 1/0052* (2013.01)

(58) Field of Classification Search
  CPC . A61B 1/267; A61B 1/00042; A61B 1/00103; A61B 1/00128; A61B 1/0052
  See application file for complete search history.

(56) References Cited

U.S. PATENT DOCUMENTS

| | | |
|---|---|---|
| 4,688,555 A | 8/1987 | Wardle |
| 5,095,888 A | 3/1992 | Hawley |
| 5,658,238 A | 8/1997 | Suzuki et al. |
| 5,695,491 A | 12/1997 | Silverstein |
| 5,704,898 A | 1/1998 | Kokish |
| 6,164,277 A | 12/2000 | Merideth |
| 6,354,993 B1 | 3/2002 | Kaplan et al. |

(Continued)

FOREIGN PATENT DOCUMENTS

| | | |
|---|---|---|
| CN | 107997825 A | 5/2018 |
| CN | 109223178 B | 4/2021 |

(Continued)

OTHER PUBLICATIONS

Nekhendzy et al.; U.S. Appl. No. 18/056,965 entitled "Robotic-assisted navigation and control for airway management procedures, assemblies and systems," filed Nov. 18, 2022.

(Continued)

*Primary Examiner* — Bradley J Osinski
(74) *Attorney, Agent, or Firm* — Shay Glenn LLP

(57) ABSTRACT

Disposable controls, re-usable devices, and their methods of use. The disposable controls and reusable devices are adapted to in operable communication during a procedure or process, and thereafter the disposable control can be discarded while the reusable device can be reused in a subsequent procedure or process. The disposable controller and reusable portion can be part of an intubation system.

34 Claims, 48 Drawing Sheets

(56) References Cited

U.S. PATENT DOCUMENTS

| | | |
|---|---|---|
| 6,494,826 B1 | 12/2002 | Chatenever et al. |
| 6,743,166 B2 | 6/2004 | Berci et al. |
| 6,832,986 B2 | 12/2004 | Chhibber et al. |
| 6,875,169 B2 | 4/2005 | Berci et al. |
| 6,890,298 B2 | 5/2005 | Berci et al. |
| 7,089,928 B2 | 8/2006 | Besharim et al. |
| 8,460,184 B2 | 6/2013 | Nearman et al. |
| 8,652,033 B2 | 2/2014 | Berci et al. |
| 8,702,602 B2 | 4/2014 | Berci et al. |
| 8,882,682 B2 | 11/2014 | Qiu |
| 8,894,569 B2 | 11/2014 | Qiu |
| 8,894,570 B2 | 11/2014 | Jiang et al. |
| 9,010,320 B2 | 4/2015 | Furman et al. |
| 9,782,061 B2 | 10/2017 | Newcomb et al. |
| 9,795,753 B2 | 10/2017 | Qiu |
| 10,286,171 B2 | 5/2019 | Gardner |
| 10,299,668 B2 | 5/2019 | Walker et al. |
| 10,398,287 B1 | 9/2019 | Genova et al. |
| 10,709,514 B2 | 7/2020 | Au |
| 10,820,792 B2 | 11/2020 | Yazdi et al. |
| 10,980,404 B2 | 4/2021 | Dray et al. |
| 11,147,634 B1 | 10/2021 | Nekhendzy et al. |
| 11,213,645 B2 | 1/2022 | Nekhendzy et al. |
| 11,324,559 B2 | 5/2022 | Nekhendzy et al. |
| 11,504,190 B2 | 11/2022 | Nekhendzy et al. |
| 11,596,494 B2 | 3/2023 | Nekhendzy et al. |
| 2003/0078476 A1 | 4/2003 | Hill |
| 2004/0220449 A1 | 11/2004 | Zirps et al. |
| 2005/0288547 A1 | 12/2005 | Okada |
| 2006/0004260 A1 | 1/2006 | Boedeker et al. |
| 2006/0041245 A1 | 2/2006 | Ferry et al. |
| 2007/0078301 A1 | 4/2007 | Kura et al. |
| 2008/0064920 A1 | 3/2008 | Bakos et al. |
| 2008/0177146 A1 | 7/2008 | Chen |
| 2008/0236575 A1 | 10/2008 | Chuda |
| 2008/0319260 A1 | 12/2008 | Murakami et al. |
| 2009/0024018 A1 | 1/2009 | Boyden et al. |
| 2009/0192350 A1 | 7/2009 | Mejia |
| 2009/0198111 A1 | 8/2009 | Nearman et al. |
| 2009/0264708 A1 | 10/2009 | Pacey et al. |
| 2010/0022825 A1 | 1/2010 | Yoshie |
| 2010/0041949 A1 | 2/2010 | Tolkowsky |
| 2011/0077466 A1 | 3/2011 | Rosenthal |
| 2011/0137127 A1 | 7/2011 | Schwartz et al. |
| 2011/0315147 A1 | 12/2011 | Wood et al. |
| 2013/0317300 A1 | 11/2013 | Berci et al. |
| 2014/0055582 A1 | 2/2014 | Demers et al. |
| 2015/0099935 A1 | 4/2015 | Runnels |
| 2015/0173598 A1 | 6/2015 | Alexander |
| 2015/0190044 A1 | 7/2015 | Livnat |
| 2015/0342690 A1* | 12/2015 | Zubiate .................. A61B 34/70 606/130 |
| 2016/0206189 A1 | 7/2016 | Nearman et al. |
| 2016/0227991 A1 | 8/2016 | Hayut et al. |
| 2016/0250432 A1 | 9/2016 | Hendrix et al. |
| 2017/0325667 A1 | 11/2017 | Alonso Babarro |
| 2018/0071473 A1 | 3/2018 | Ferrario |
| 2018/0110950 A1 | 4/2018 | Runnels et al. |
| 2018/0147381 A1 | 5/2018 | Chen |
| 2018/0153389 A1 | 6/2018 | Dixon et al. |
| 2018/0221610 A1 | 8/2018 | Larson et al. |
| 2019/0125177 A1 | 5/2019 | Sutherland |
| 2019/0133430 A1* | 5/2019 | Inglis .................. A61B 1/00052 |
| 2019/0142262 A1 | 5/2019 | Inglis et al. |
| 2019/0328224 A1 | 10/2019 | Nevin |
| 2020/0029793 A1 | 1/2020 | McGrath et al. |
| 2020/0275824 A1 | 9/2020 | Tata et al. |
| 2021/0030265 A1 | 2/2021 | Inlis et al. |
| 2021/0045822 A1 | 2/2021 | Landey et al. |
| 2021/0121155 A1 | 4/2021 | Macguire et al. |
| 2021/0259521 A1 | 8/2021 | Hwang |
| 2022/0008140 A1* | 1/2022 | Nekhendzy ........ A61B 1/00096 |

FOREIGN PATENT DOCUMENTS

| | | |
|---|---|---|
| CN | 113400304 A | 9/2021 |
| WO | WO2018/112057 A1 | 6/2018 |
| WO | WO2020/020558 A1 | 7/2018 |
| WO | WO2021/242736 A1 | 12/2021 |
| WO | WO2022/132600 A1 | 6/2022 |
| WO | WO2023/060241 A1 | 4/2023 |
| WO | WO2023/164434 A2 | 8/2023 |

OTHER PUBLICATIONS

Nekhendzy et al.; U.S. Appl. No. 18/172,538 entitled "Robotic-assisted navigation and control for airway management procedures, assemblies and systems," filed Feb. 22, 2023.

* cited by examiner

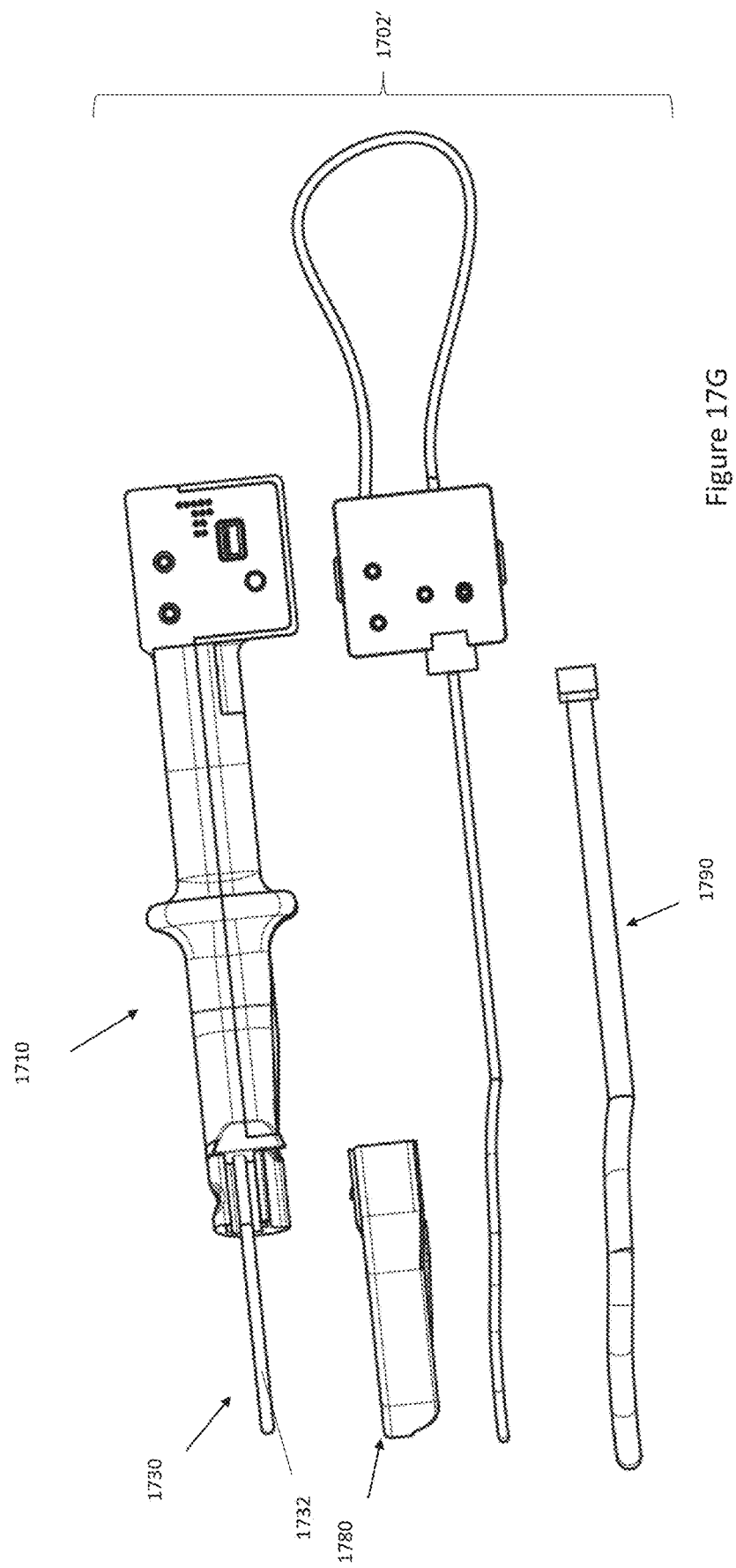

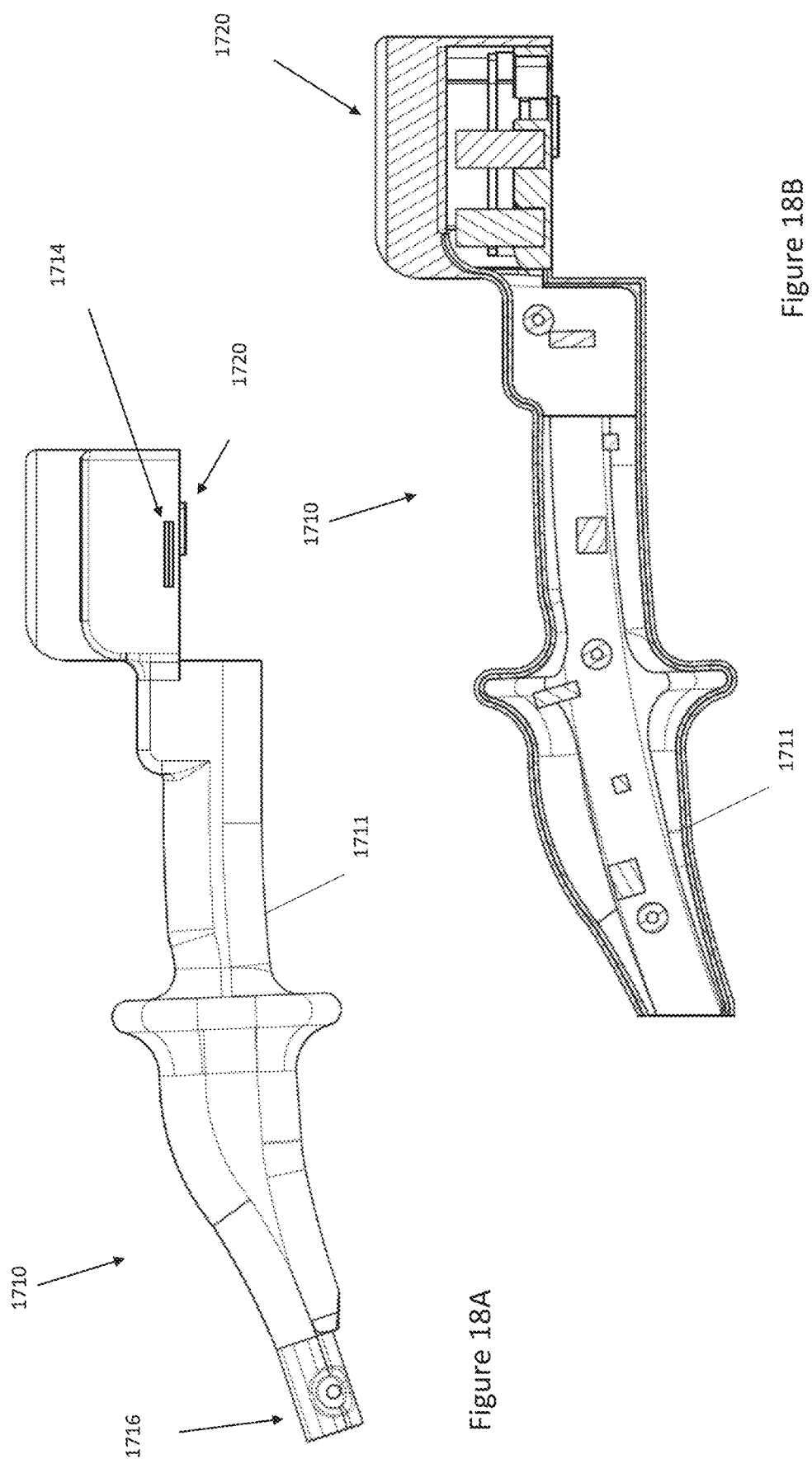

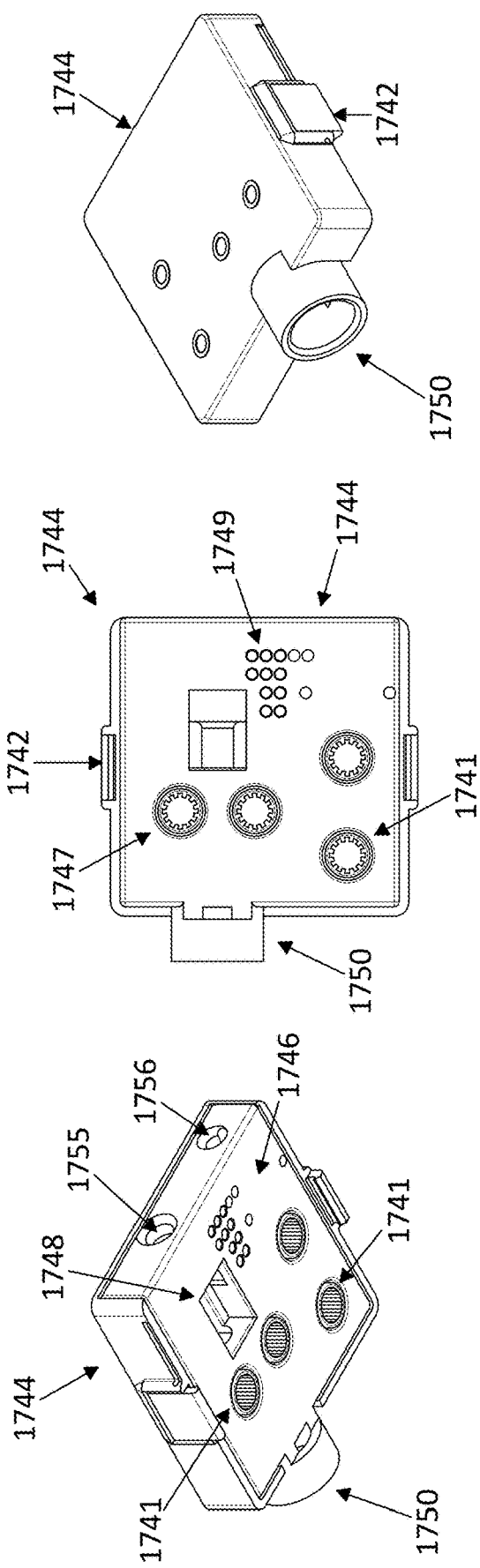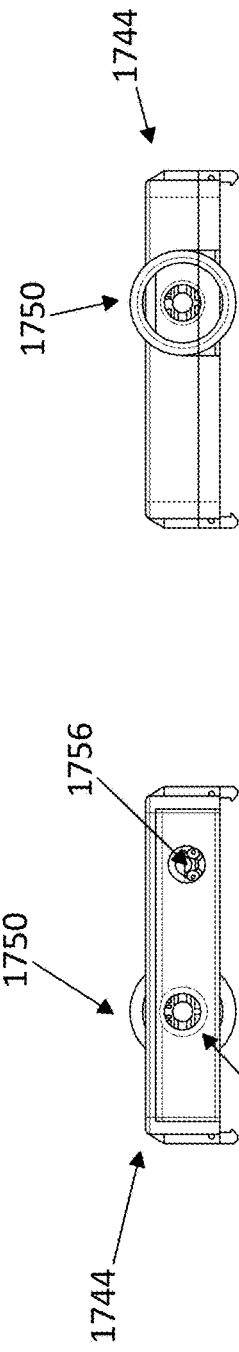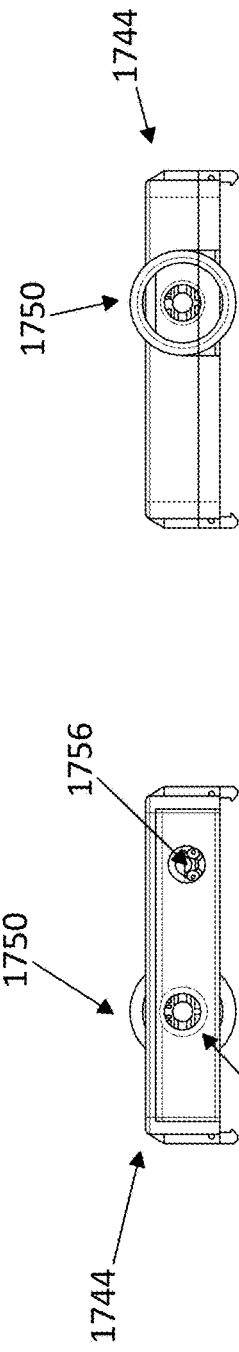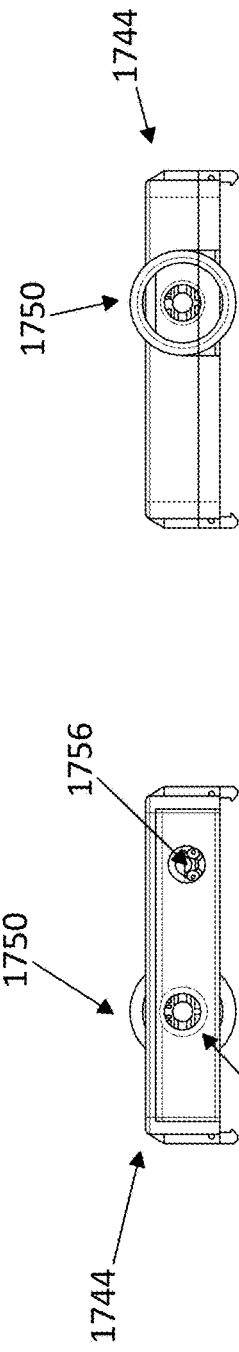

DISPOSABLE CONTROLS, RE-USABLE DEVICES, AND THEIR METHODS OF USE

INCORPORATION BY REFERENCE

This application claims priority to U.S. Provisional Application Nos. 63/329,449, filed Apr. 10, 2022, and 63/352,774, filed Jun. 16, 2022, the entire disclosures of which are incorporated by reference herein in their entireties for all purposes.

The following references are fully incorporated by reference herein in their entireties for all purposes: PCT Pub. No. WO2021/236677, published Nov. 25, 2021; U.S. patent Ser. No. 11/147,634, issued Oct. 19, 2021; and PCT App. No. PCT/US2023/062952, filed Feb. 21, 2023.

All publications and patent applications mentioned in this specification are herein incorporated by reference to the same extent as if each individual publication or patent application was specifically and individually indicated to be incorporated by reference.

BACKGROUND

A variety of medical devices include a portion that is controllable during a procedure. For example, without limitation, any of the following may include one or more controllable parts: colonoscopes, bronchoscopes, esophageal scopes, articulating laparoscopes, other endoscopes, articulating surgical tools, feeding tube systems, articulating catheters, laparoscopic devices, bone surgery devices, any handheld controllable device, or other devices that may be used in procedures with the aforementioned devices. The device or system may generally include one or more operator controls, or components that are adapted to be actuated by an operator to control a portion of the device (e.g., buttons, joysticks, sliders, etc.). Once contaminated during the procedure, the control must be sterilized before the device can be used again. For handheld devices, the controls are usually integrated into a portion of the device that is difficult or expensive to sterilize. Devices and systems are needed that allow for accurate control of the medical device to fulfill its intended purpose(s), while allowing one or more of its parts (e.g., expensive components and/or integrated controls) to be re-used in a subsequent procedure without requiring re-sterilization. There may be other applications as well outside of the medical device industry, such as in industrial applications.

SUMMARY OF THE DISCLOSURE

The disclosure is related to disposable controls and methods of use. The disposable controls may have applications in the medical device field, and may have applications in other fields such as in industrial applications. The phrases disposable controls and disposable controllers may be used interchangeably herein.

Disposable controls or controllers are generally adapted to be placed in operable communication with a re-usable device. The disposable controls are adapted to be controlled by an operator to thereby control one or more components of the re-usable device. Once the procedure or process is complete, the disposable control can be separated from the re-usable and discarded. The re-usable device can be used again for a subsequent procedure or process, and in the medical device field the re-usable need not be sterilized before being reused.

A merely exemplary implementation of the disposable controls and re-usable devices herein is in the medical device field, and even more exemplary is for airway management, examples of which are described throughout this disclosure.

One aspect of the disclosure is a disposable controller for a controllable medical system. The controller optionally includes a body or housing that includes at least one control member that is adapted to be actuated by a user (optionally manually actuated). The body optionally also includes a cavity therein.

In this aspect, the disposable controller optionally has an articulatable tool at a distal end thereof, such as without limitation, graspers, scissors, energy delivery devices, etc.

In this aspect, the disposable controller is optionally adapted to be coupled and uncoupled from a reusable electronics package, an example of which is shown in FIG. 33.

This aspect may include any suitably combinable feature(s) from any other aspect, embodiment, or example herein, including the figures and claims.

One aspect of the disclosure is a re-usable device. The re-usable device may optionally include at least one control member interface element that is adapted and positioned to be in operable communication with the at least one control member of a disposable controller and responsive to the actuation of the at least one control member when the re-usable and disposable controller are placed in operable communication.

This aspect may include any suitably combinable feature(s) from any other aspect, embodiment, or example herein, including the figures and claims.

One aspect of the disclosure is a controllable medical system. The system may optionally include a disposable controller and a robotically controllable medical device ("medical device").

In this aspect, the disposable controller optionally includes a body that includes at least one control member that is adapted to be actuated (optionally manually actuated) by a user. The body also optionally includes a cavity.

In this aspect, at least a portion of a robotically controllable medical device is sized and configured to be disposed in a cavity of the disposable controller.

In this aspect, the medical device optionally includes at least one control member interface element that is adapted and positioned to be placed in operable communication with the at least one control member of the disposable controller (optionally within a cavity) and responsive to the actuation of the at least one control member, optionally when at least a portion of the medical device is disposed in a cavity.

In this aspect, the medical device optionally includes a controllable member, at least a portion of which is movable in at least one direction during a procedure or process (e.g., a controllable or articulatable shaft, tool, etc.).

In this aspect, the re-usable medical device optionally includes at least one controllable member actuator (such as a motor, for example) in operable communication with the at least one control member interface element and in operable communication with a controllable member to cause controlled robotic motion of the controllable member in response to user actuation of the at least one control member.

In this aspect, a controllable member optionally comprises an endoscope.

In this aspect, a controllable member optionally comprises a controllable catheter.

In this aspect, a controllable member optionally comprises a surgical tool.

In this aspect, a controllable member optionally comprises an endotracheal tube introducer, such as any of the ETT introducers herein.

This aspect may include any suitably combinable feature(s) from any other aspect, embodiment, or example herein, including the figures and claims.

One aspect of this disclosure is a method of performing a medical procedure on a subject with a disposable controller.

In this aspect, the method may include positioning at least a portion of a reusable device into a cavity of a disposable controller, whereby the positioning step positions a control member of the disposable controller in proximity to a control member interface element of the reusable device such that the control member interface element is responsive to user actuation (e.g., manual actuation) of the control member, wherein the reusable medical device further comprises a controllable member interface element and at least one controllable member actuator, the at least one controllable member actuator in operable communication with the at least one control member interface element and in operable communication with the controllable member.

In this aspect, the method may further comprise manually moving the control member to cause controlled robotic motion of the controllable member in at least one direction of motion.

In this aspect, the method may include removing the reusable device from the disposable controller such that the control member interface element of the reusable device is no longer responsive to user actuation of the control member of the disposable controller.

This aspect may include any suitably combinable feature(s) from any other aspect, embodiment, or example herein, including the figures and claims.

One aspect of this disclosure is a disposable controller for an intubation procedure. In this aspect, the disposable controller may comprise a distal blade region that is sized and configured to be positioned in a mouth. In this aspect, the disposable controller may include an extension that extends from and is optionally unitary with the distal region, and which is configured and sized to be handheld. The extension may include a disposable controller means for being actuated by a user to communicate with a re-usable device (e.g., joystick, magnet, button, etc.).

This aspect may include any suitably combinable feature(s) from any other aspect, embodiment, or example herein, including the figures and claims.

One aspect of this disclosure is a reusable introducer assembly adapted for an intubation procedure. In this aspect, at least a portion of the assembly may be sized and configured to be disposed in a cavity of a disposable controller. In this aspect, the assembly may optionally include responsive control means for responding to actuation of the at least one control member of a disposable controller, optionally when at least a portion of the assembly is disposed in a cavity of a disposable controller.

In this aspect, the assembly may further include at least one introducer actuator in operable communication with the at least one responsive control means for responding and in operable communication with the introducer to cause controlled robotic motion of the introducer in at least one degree of motion in response to user actuation of the at least one control member.

This aspect may include any suitably combinable feature(s) from any other aspect, embodiment, or example herein, including the figures and claims.

One aspect of the disclosure is an intubation system.

In this aspect, the system may include a disposable blade that includes a distal region sized and configured to be positioned in a mouth, and an extension that extends from the distal region, and which is configured and sized to be handheld. The extension may comprise at least one control member or control means that is adapted to be actuated (e.g., manually) by an operator. The extension may optionally include a cavity.

In this aspect, the system may include a reusable introducer assembly ("assembly"), at least a portion of which is optionally sized and configured to be disposed in a cavity of the disposable blade. The assembly may optionally include at least one control member interface element that is adapted to be disposed in the cavity, positioned to be in operable communication with the at least one control member and responsive to the manual actuation of the at least one control member when at least a portion of the assembly is disposed in the cavity. The assembly may optionally include an ETT introducer ("introducer"). The assembly may optionally include at least one introducer actuator in operable communication with the at least one control member interface element and in operable communication with the introducer to cause controlled robotic motion of the introducer in at least one direction of motion in response to user actuation of the at least one control member.

In this aspect, the at least one control member interface element may be adapted and positioned to sense one or more of motion, proximity, positioning, velocity, acceleration, or current.

In this aspect, the at least one control member may comprise a magnet and the at least one control member interface element may comprise a Hall sensor.

In this aspect, the at least one control member may include a joystick, and the at least one control member interface element may comprise one or more metal contact surfaces.

In this aspect, the at least one control member and the at least one control member interface element are optionally in at least one of electrical, magnetic, mechanical or optical operable communication.

In this aspect, the at least one control member may comprise a flexible material.

In this aspect, the extension may comprise a rigid material.

In this aspect, the at least one control member may comprise a rigid, movable material.

In this aspect, the at least one control member may comprise one or more pogo pins.

In this aspect, the assembly may include a housing that comprises the at least one control member interface element and the at least one introducer actuator, and wherein the introducer is optionally adapted to be releasably coupled to the housing to facilitate operable communication between the at least one introducer actuator and the introducer when the introducer is releasably coupled to the housing.

In this aspect, the disposable blade may comprise an endotracheal tube side channel, examples of which are shown and described herein.

In this aspect, the at least one introducer actuator may comprise a motor.

This aspect may include any suitably combinable feature(s) from any other aspect, embodiment, or example herein, including the figures and claims.

One aspect of this disclosure is an intubation system. The system may include a disposable controller that is configured and sized to be handheld, wherein the disposable controller includes at least one control member that is adapted to be actuated (e.g., manually) by an operator. The disposable controller optionally also includes a cavity.

In this aspect, the system includes a reusable housing, at least a portion of which is optionally sized and configured to be disposed in an optional cavity of the disposable controller. The reusable housing may include at least one control member interface element that is optionally adapted to be disposed in the cavity, positioned to be in operable communication with the at least one control member and responsive to the manual actuation of the at least one control member optionally when at least a portion of the assembly is disposed in the cavity. The reusable housing may further include at least one endotracheal tube introducer actuator in operable communication with the at least one control member interface element and adapted to be in operable communication with an endotracheal tube introducer to cause controlled robotic motion of the introducer in at least one direction of motion in response to user actuation of the at least one control member.

This aspect may include any suitably combinable feature(s) from any other aspect, embodiment, or example herein, including the figures and claims.

One aspect of this disclosure is related to packaging the disposable controllers and the re-usable devices, wherein the disposable controllers and the re-usable devices may be packaged together or separately, and if together, they may be packaged in operable communication or not in operable communication. In this aspect, a plurality of disposable controllers (e.g., any of the disposable blades with controllers herein) may be packaged together, with or without a re-usable device that they are adapted to be used with during a procedure or process.

One aspect of the disclosure herein is just the re-usable device, without necessarily requiring a disposable controller. For example, a re-usable device may be packaged separately, and may be adapted for use with a variety of disposable controllers. This aspect may include any suitably combinable feature(s) from any other aspect, embodiment, or example herein, including the figures and claims.

One aspect of this disclosure is a disposable handheld intubation controller, comprising a distal blade region sized and configured to be positioned in a mouth, an extension that extends from the distal blade region, the extension configured and sized to be handheld.

In this aspect, the extension may include at least one user control member or control means that is adapted to be actuated (optionally manually) by a user.

In this aspect, the extension may include a cavity, optionally an elongate cavity, such as cavities shown and described herein.

In this aspect, the at least one control member may be 180 degrees offset from a distal end of the distal blade region, as shown in representative figures herein.

This aspect may include any suitably combinable feature(s) from any other aspect, embodiment, or example herein, including the figures and claims.

BRIEF DESCRIPTION OF THE DRAWINGS

FIG. 17G illustrates a top view of an exemplary integrated and handheld dual-video tracheal intubation assembly, shown unassembled.

FIG. 18A shows a side view of an exemplary housing.

FIG. 18B shows a side view of an exemplary section view of housing from FIG. 18A.

FIG. 19G shows a bottom perspective view of an exemplary housing of a second imaging member.

FIG. 19H shows a bottom view of an exemplary housing of a second imaging member.

FIG. 19I shows a top perspective view of an exemplary housing of a second imaging member.

FIG. 19J shows a front, end view of an exemplary housing of a second imaging member.

FIG. 19K shows a back, end view of an exemplary housing of a second imaging member.

DETAILED DESCRIPTION

Figure 1:
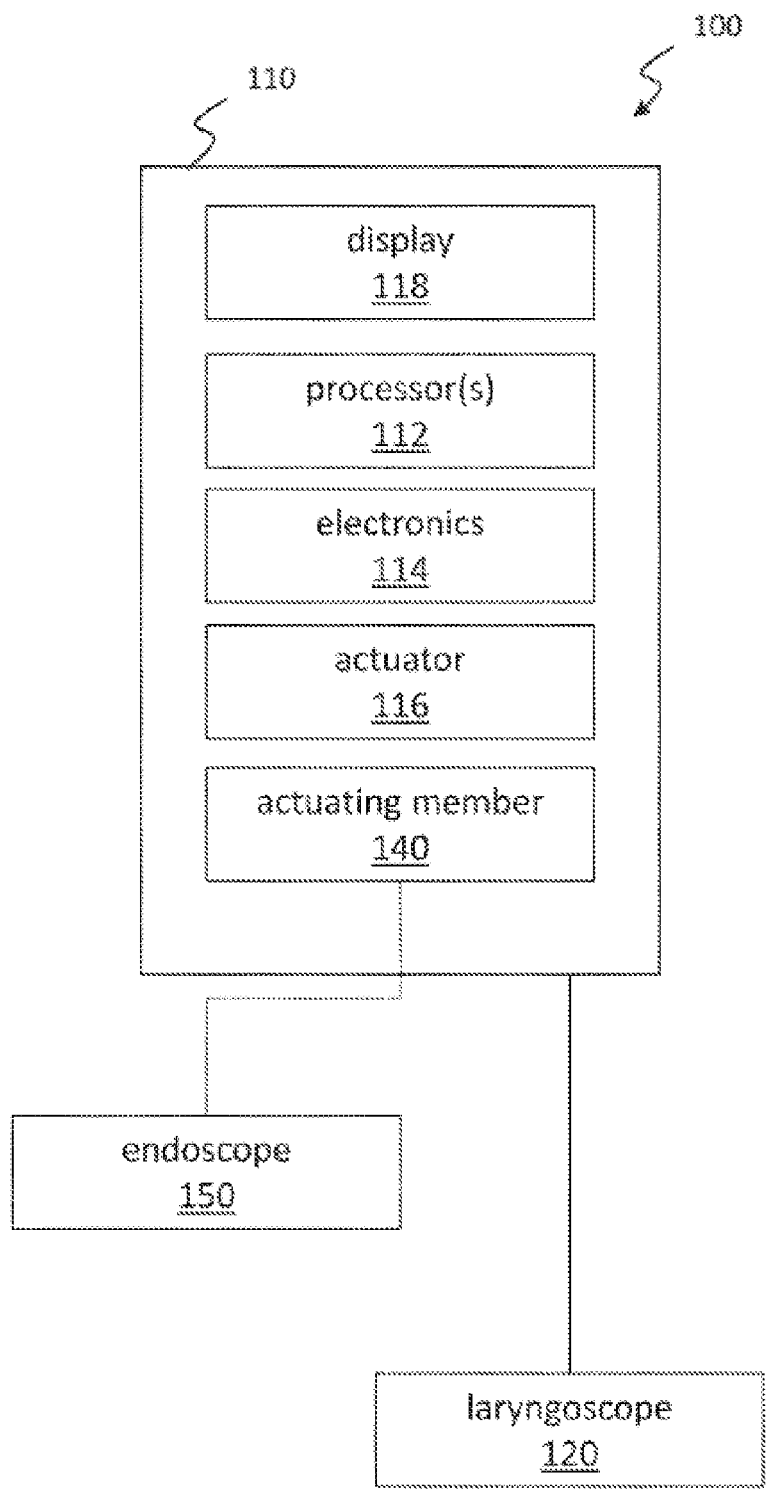
FIG. 1 depicts a schematic of an example variation of a device for assisting navigation and/or intubation in a patient.

Examples of various aspects and variations of the inventions are described herein and illustrated in the accompanying drawings. The following description is not intended to limit the inventions to these embodiments, but rather to enable a person skilled in the art to make and use these inventions.

The disclosure herein is related to devices that include a disposable control (not intended to be re-used in subsequent procedures) and a re-usable portion. The disposable control and the re-usable portions are generally adapted such that the disposable control can be actuated (e.g., handheld) by an operator to control one or more portions of the re-usable portion. During the procedure or process, the re-usable portion remains sterile and need not be sterilized to be used again, while the disposable control can be separated from the reusable after the process or procedure and discarded. A new disposable control can be used with the reusable in a subsequent procedure or process.

Some exemplary devices herein that incorporate the disposable controls herein are related to airway management, but these are merely exemplary devices and uses, and it is understood that the disposable controls and controllers herein have much broader applicability with other medical devices, as well as in other fields such as in industrial applications. While tracheal intubation is provided as an example of airway management herein, the concepts herein may be applied or applicable to other airway management procedures, locations and settings. For example, concepts herein may be used in bronchoscopy procedures or in endoscopic ENT procedures such as flexible nasolaryngoscopy, esophagoscopy, vocal cord injections, certain laryngologic surgical procedures, and other endoscopy procedures involving upper gastrointestinal (GI) tract (e.g., gastroscopy, esophagoscopy) etc.

Airway management procedures herein may include any of the following exemplary and non-limiting procedures in both adult and pediatric patients: 1) endoscopic evaluation of the airway in a patient to determine or establish: (a) the presentation of and the relationship between different parts of the upper airway anatomy, (b) the size and location of the lesion(s) and/or location and the extent of the pathological process(s), (c) the feasibility of the supraglottic airway devices (SGAs, e.g., laryngeal mask airway, etc.) placement and the likelihood of successful SGA ventilation, (d)

whether awake and/or TI is feasible, (e) an optimal TI navigation pathway to the larynx, (f) the optimal TI device use and the optimal TI strategy; 2) facilitating the exchange of the ETT; 3) Evaluation of the positioning and/or patency of ETT and/or confirming the correct placement of ETT inside the trachea; 4) facilitating placement and confirming proper positioning of the double lumen tubes; 5) facilitating an extubation trial; 6) performing the bronchoscopy; 7) performing a nasal and/or an oral TI; 8) performing the ENT procedures, such as endoscopies, esophagoscopies, biopsies, injections, certain laryngologic surgical procedures; and 9) performing other airway therapeutic, interventional and/or diagnostic procedures.

As used herein, airway management procedures may be used in any of these non-limiting locations and settings: OR, ICU, ED, out-of-OR locations (e.g. endoscopy suits, imaging scanners, different ambulatory and hospital settings, procedure rooms, etc.), and in the field (e.g. EMS) and battlefield airway management, both on site and during the patient transport.

Airway management as used herein may include or be used in visualization procedures, diagnostic procedures, interventional procedures, surgical procedures, and/or therapeutic and diagnostic procedures.

Airway management concepts described herein may find utility in non-medical applications.

Devices and systems adapted for assisting navigation and/or intubation.

Some non-limiting aspects of the disclosure herein are directed to portable, hand-held, and integrated dual-video enhanced visualization and navigation systems that are adapted for guiding an ETT into a patient's trachea during a TI procedure. Such systems are adapted and configured to provide and improve all 3 critical steps required for successful TI: Visualization, Navigation/Movement and Placement. An integrated dual-video system that is configured, adapted and sized to be held in a single hand of a user provides the benefit that the user is able to single-handedly hold and optionally control the dual-video integrated and enhanced visualization and navigation system, allowing a single operator to reliably facilitate the navigation and movement of an ETT introducer guide into a trachea of the patient. The integrated dual-video systems herein provide enhanced visualization of the patient's airway anatomy, which facilitates enhanced navigation of the ETT in and around the patient's anatomical structures as well as improved ETT placement (insertion) both through the glottic opening and into the patient's trachea during a TI procedure, all of which help reduce TI trauma, increase the likelihood of first pass TI success (the success of TI on the first TI attempt).

The disclosure herein may refer to navigation when describing movement of an introducer. It is understood that in some instances navigation may also refer to automatic determination of how or where the introducer is to be robotically moved (e.g., using image recognition). Navigation may be performed manually in embodiments in which an operator determines how or where to move the introducer, such as, for example, based on viewing an image on a display.

Described herein are variations of devices, systems and methods for robotically assisting navigation and movement of an introducer within an airway or other passageway in a patient, such as during an intubation procedure (e.g., orotracheal intubation, nasotracheal intubation, etc.). In some examples herein, the robotically assisted movement herein may include using artificial intelligence (AI) to enable the robotically assisted navigation. As shown in the schematic of FIG. 1, in some variations, an integrated robotic device or system 100 may include a housing 110, a laryngoscope or baton 120 (e.g., a video laryngoscope) coupled to the housing and including a first image sensor, and an actuating member 140 disposed at least partially in the housing. Housing 110 may, for example, be an integrated, handheld device so as to be portable and/or configured to be easily operated by a single person. The actuating member may be movable within the housing, and an introducer such as an endoscope 150 (e.g., video endoscope) may extend from the actuating member 140. The introducer may include a second image sensor and may be configured to be slidably coupled to an intubation tube such as an ETT, wherein the coupling may comprise the ETT being slidably disposed about the introducer. When the introducer is robotically moved to a passageway of a patient (e.g., trachea), the introducer may function as a steering guide for intubation tube advancement during the intubation procedure. Intubation tube advancement may be performed, for example, either manually or automatically by passing the intubation tube over the introducer. Once intubation tube placement (such as in a trachea) is confirmed via real-time images from the one or more image sensors (such as the introducer image sensor when the introducer is in the trachea), the intubation tube may be decoupled from the introducer (which may include sliding the introducer proximally out of and relative to the ETT), and the introducer and the rest of the device 100 may be withdrawn from the patient's anatomy, leaving the intubation tube (e.g., ETT) in place.

In any of the examples and embodiments herein, the robotically assisted navigation/movement can include robotically assisted navigation of an introducer, of which endoscopes (which may be referred to as scopes herein) described herein are examples. The introducers herein are generally described as including one or more image sensors, but in alternative systems they may not include an image sensor, or the image sensor may not be continuously used. In examples in which the introducer does not include an image sensor (or the image sensor is not in continuous use), the introducer may be robotically navigated with AI-assistance using images obtained from an integrated image sensor, such as an image sensor associated with a first imaging member, such as a video laryngoscope, for example, exemplary details of which are described herein. When utilizing a non-optical introducer, placement of the intubation tube below the vocal cords (lower airway) is not visualized with the non-optical introducer, and thus intubation tube placement below the cords cannot be immediately confirmed. A non-optical introducer, may, however, depending on the application and clinical situation, provide simplicity and cost advantages compared to optical introducers such as the optical introducers described herein that include one or more image sensors.

Although the devices, systems, assemblies and methods are primarily described herein with reference to an intubation procedure, it should be understood that the devices and methods may be used to assist other medical airway management procedures involving navigation through one or more passageway, such as endoscopy procedures (e.g., bronchoscopy, etc.). For example, navigation of the introducer may be robotically-assisted using devices and methods such as those described herein, except that the introducer may be automatically guided using AI/automated techniques without being coupled to an intubation tube. For example, the device may robotically assist navigation of the introducer during any suitable medical endoscopic procedure to provide for a faster and/or less traumatic endoscopic procedure compared to conventional manual techniques. As an illustrative example, the devices, systems, assemblies and methods described herein may, instead of automatically guiding an intubation tube, automatically guide an introducer (e.g. endoscope 150) based one or more images obtained with the introducer and or first imaging member (e.g., laryngoscope). In some variations, the introducer (e.g. endoscope 150) may include one or more channels for irrigation, drug delivery, tissue biopsy and/or deployment of a surgical instrument, for example.

Even further, in some variations, devices, system, assemblies and methods herein may be used in other applications (e.g., non-medical applications) in which automated navigation/movement may be helpful, such as navigation within a passageway that is challenging to otherwise access.

Exemplary system 100 in FIG. 1 may optionally include at least one display 118 configured to display one or more images from a first image sensor in a first imaging member (e.g., laryngoscope) and/or a second image sensor of a second imaging member (which may comprise an introducer), and may be configured to display images from both the first and second image sensors simultaneously, such as split-screen or picture-in-picture. The images may be displayed continuously or substantially continuously or sequentially during the procedure. System 100 may further include at least one actuator 116 in the housing that is configured to automatically guide/move the introducer (e.g., an endoscope) via the actuating member 140, based at least in part on one or more images from the first image sensor and/or the second image sensor. In some variations, the system may further include a cover or blade coupled to the housing, where the cover may include a first channel sized and configured to receive a first elongate imaging member (such as a video baton) and a second channel configured to stably receive at least a portion of an intubation tube (in which an introducer may be disposed). The cover may further include a tongue retracting member (such as an angled or curved member) configured to retract a tongue of a patient during an intubation procedure, examples of which are shown in figures herein.

In some variations, one or more actuators may be under operational control by one or more processors 112 configured to analyze images or image data from one or both of first and second image sensors in the system using suitable AI (e.g., machine learning methods). Various electronics 114 (e.g., power source(s), electronic communication lines, etc.) in the system or housing 110 and/or display 118 may power the one or more processors, image sensors, light guides, etc. in the system. AI-based image recognition in real-time or near real-time of the patient's upper airway anatomy (above the vocal cords) and/or lower airway anatomy (below the vocal cords) may, for example, trigger robotic-assisted tracheal intubation with the system. As described in further detail below, the visualization and navigation/movement to or towards the vocal cords may, for example, be based on identifying one or more key anatomic recognition points provided by the image sensor(s) of the first and/or second imaging members. The system may perform robotic-assisted navigation that is activated either automatically in response to recognizing airway anatomy, and/or in response to a manual activation (e.g., through user operation of a user interface element). For example, in a fully automated mode of exemplary device or assembly 100, the actuator may automatically maneuver the endoscope using AI and/or other robotic-assisted navigation, and electromechanical control of the actuating member.

Additionally or alternatively, the device or system may operate in an automated mode with an exemplary manual assist. In such an automated-manual assist mode, for example, the actuating member and/or introducer may be controlled manually, such as with the use of a user interface device (e.g., joystick) or through the device display 118. Articulation of a distal tip of the introducer when the device is in the automated-manual assist mode may, for example, occur automatically under automatic robotic control of one or more actuators in the system.

When used for TI, the systems herein may be user-friendly, portable, handheld, video-triggered and AI-enabled robotic assisted automated intubation systems with enhanced functionality that improve all three critical steps required for successful TI: visualization, navigation and placement, and increase first-pass intubation success rate, decrease overall intubation time, reduce intubation-related airway trauma, and/or improve patient safety. For example, the systems herein may, in an ergonomic package operable by a single user, combine multiple imaging (e.g., video) modules that allow the device to perform intubation using AI or robotic-assisted introducer navigation. The robotic-assisted intubation interface may, for example, maneuver at least the guiding introducer through the glottis and into the patient's trachea, where it may serve as a guide for ETT advancement and placement. The ETT may, for example, be preloaded onto the introducer and advanced over the introducer after the introducer is advanced into the trachea and after proper placement in the trachea is confirmed.

Among other advantages such as those described herein, the systems herein may be configured to provide continuous visual feedback and optional closed-loop robotic assistance for real-time troubleshooting and/or intelligent intervention during tracheal intubation, both from above and below the vocal cords, thereby improving TI success rate, improving the intubation speed and reducing TI trauma. Additionally, combined use of the first and second imaging members may allow for reliable and faster triggering of AI and the associated robotic interface, due at least in part to an enlarged and clear view of the upper airway anatomical landmarks provided by the first imaging member (such as laryngoscope 120). Another advantage of acquiring initial imaging through the first imaging member refers to the fact that visualization of the patient's anatomy is much less affected by blood and secretions compared to the image provided by the second imaging member (e.g. an image sensor at a distal region of an introducer). Furthermore, combined use of a first and second imaging members, the angular orientation of their respective video cameras and the placement and maintenance of their video cameras in close axial proximity to each other and to the glottic opening, provides for the shortest, quickest navigation pathway for the introducer and ETT to the vocal cords and trachea. Furthermore, the actuation of the introducer within the patient's airway is greatly facilitated by the device cover or blade, which is configured to perform tongue retraction, thereby creating greater pharyngeal space for introducer actuation and maneuvering. One of the optionally significant benefits of some of the systems herein is that the system may be configured to allow a user to observe the intubation procedure in its entirety, both from above (upper airway) and below the vocal cords (lower airway), to permit immediate visual confirmation of intubation tube placement inside the trachea during intubation using an introducer imaging sensor, and to assure that the intubation tube is positioned optimally inside the patient's airway, exemplary embodiments of which are described below.

Furthermore, the merely optional integrated dual-video capability of some exemplary systems herein may significantly reduce intubation-associated airway trauma and soft tissue injury that is often associated with conventional devices, even in the situations when visualization of the upper airway anatomical landmarks is limited (e.g. in the absence of full glottis exposure). For example, after identifying the anatomical structures reliably associated with the glottic opening (e.g. epiglottis, arytenoid cartilages, etc.) during initial video image capture with a first image sensor, the system can automatically maneuver the introducer through the glottic opening into the patient's trachea even when the glottic opening cannot be visualized. The device may also reduce the risk of esophageal intubation and/or disturbance, defragmentation, bleeding, and/or airway soiling during intubation, such as when tumors or other space-occupying lesions are present inside the patient's airway.

In some variations, the systems may be useful in situations in which increased distance from the patient's airway is desirable to decrease the likelihood of airborne and/or contact transmission of infection from the patient to the operator of the device. For example, because of the minimal airway manipulation required and the automated nature of the intubation performed, the operator of the integrated system may be able to hold the system from a suitable distance (e.g., arm's length) and avoid the risk of directly looking inside the patient's airway to reduce the likelihood of transmission of infection (e.g., from patients with contagious bacterial and/or viral disease, such as COVID-19 and others).

The systems herein may be used in, for example, for routine elective and/or anticipated and/or unanticipated difficult tracheal intubation in any suitable setting, such as OR, ICU, emergency department, out-of-OR locations (e.g., clinics, code situations, etc.), pre-hospital conditions (e.g. field and battlefield airway management), and/or other elective and/or urgent and/or emergent situations. Additionally, the systems may be used for TI for a wide range of patients and across a variety of diagnostic and/or therapeutic procedures, such as where airway support and/or protection of the patient's airway and/or pulmonary hygiene is desired or indicated, such as the patients undergoing interventional endoscopy procedures (bronchoscopy, GI endoscopy, etc.), transesophageal echocardiogram, CT and MRI imaging procedures, any medical procedures that may require sedation and/or airway support and/or airway protection, etc. The systems may be useful for TI in specific patient populations where increased TI difficulty may be anticipated, such as those who are obese, have obstructive sleep apnea, patients with head and neck cancer and other pathology, elderly patients, patients at high risk for dental damage, patients in whom neck movements are not desirable, trauma patients, patients for whom it is important to minimize adverse cardiovascular responses to intubation (e.g., hypertension, tachycardia, arrhythmias, etc.), critically ill patients and others. The device may, in some variations, by useful for TI among adults and pediatric patients.

Figure 2A:
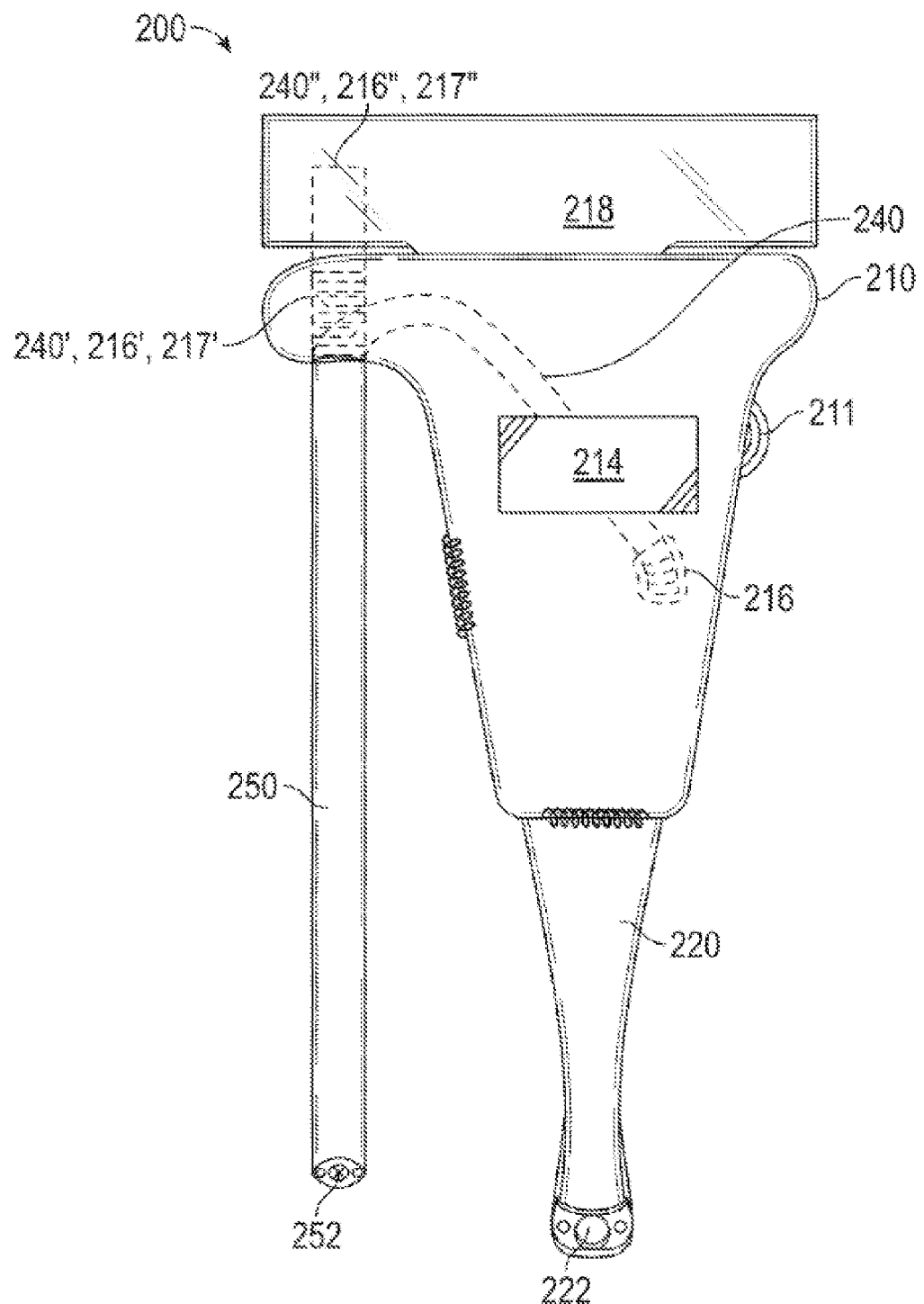
FIG. 2A depicts an example variation of a device for assisting navigation and/or intubation in a patient.
Figure 2B:
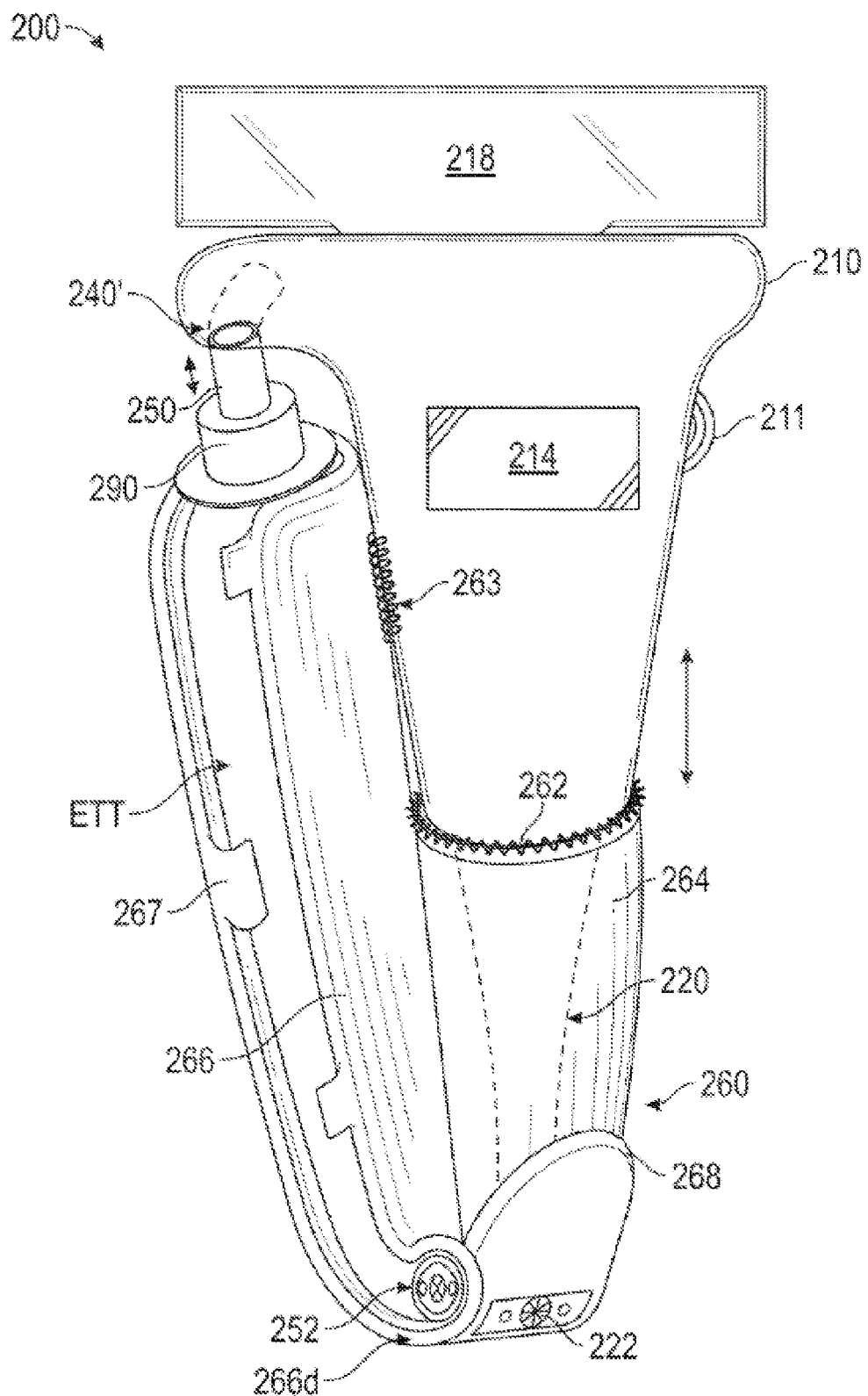
FIG. 2B depicts a front view of the example variation of a device shown in FIG. 2A, including a cover.
Figure 2C:
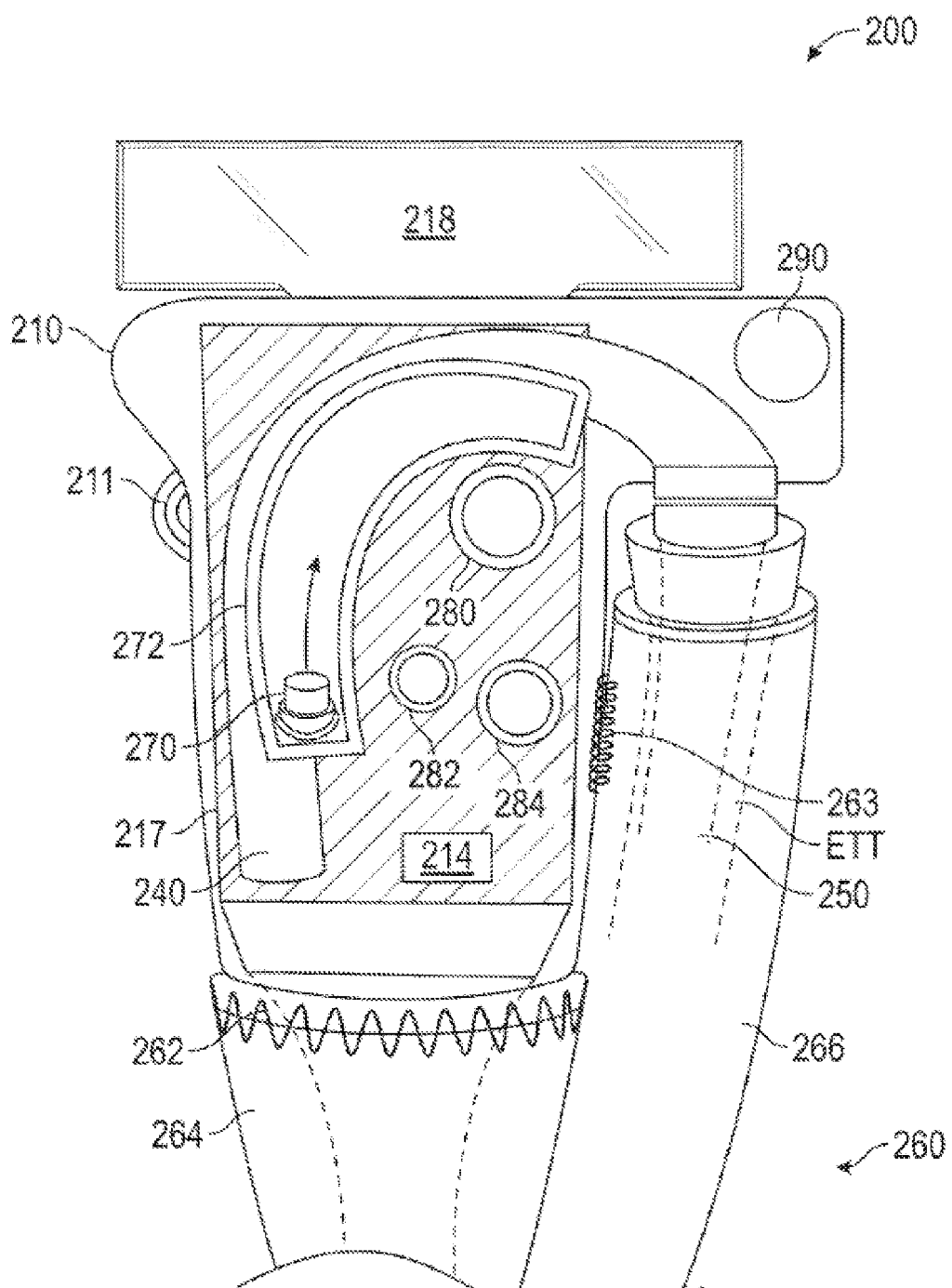
FIG. 2C depicts a rear view of the example variation of the device shown in FIG. 2B.
Figure 3A:
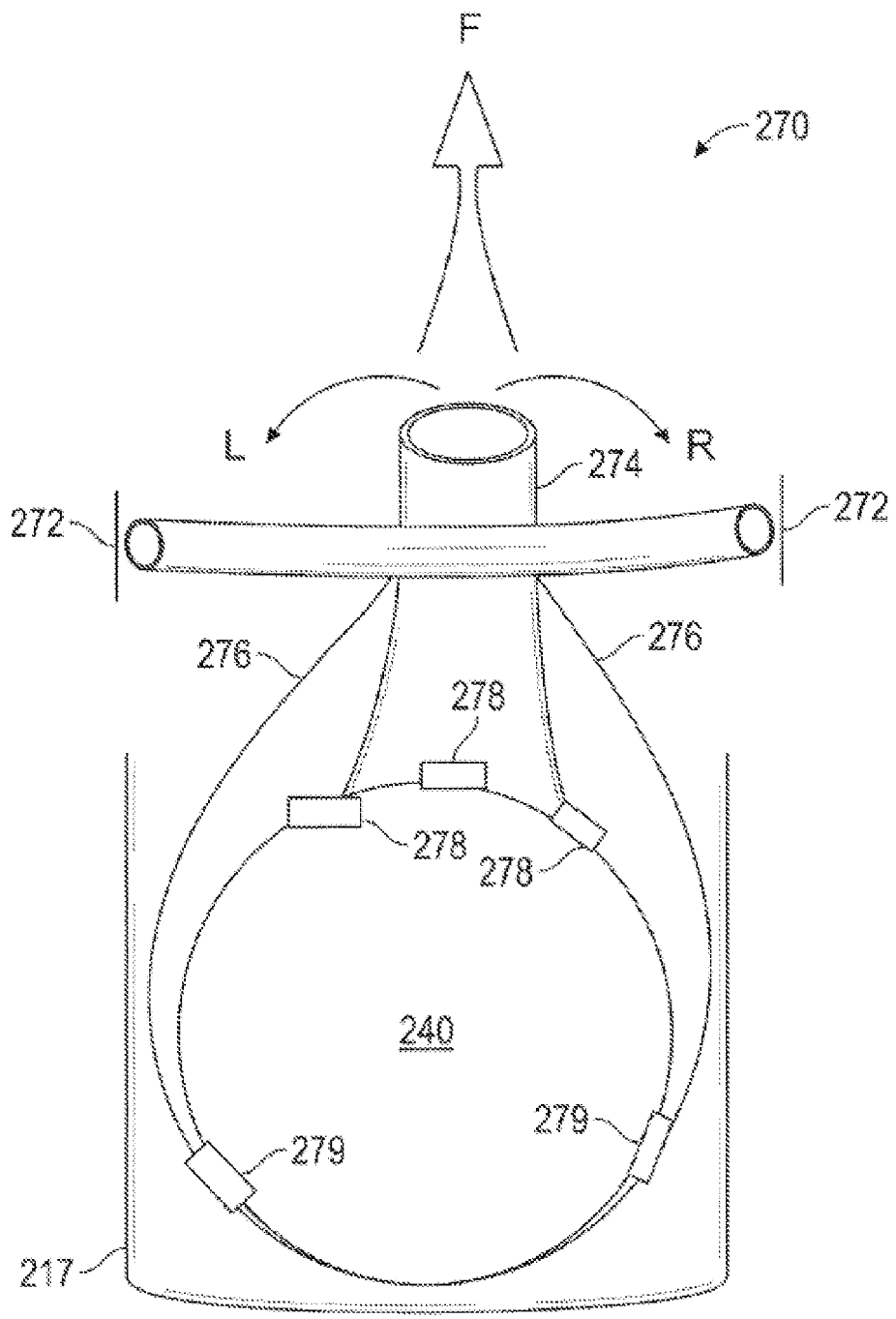
FIG. 3A depicts a cross-sectional view of an example variation of a manual actuating system for guiding an actuating member in a device for assisting navigation and/or intubation in a patient.

FIGS. 2A-2C are schematic illustrations of a merely exemplary portable, hand-held integrated dual-video robotic assembly or system 200, which may be adapted for visualization and navigation and placement during of an intubation procedure. As shown in FIG. 2A, system 200 may include handheld housing 210, electronics system 214 (e.g., including one or more processors, one or more power sources, etc., examples of which are described herein), and one or more actuators 216. The device may further include a first elongate imaging member such as a laryngoscope with a baton 220 (or other imaging member) with at least one image sensor 222 disposed at a distal region of the first imaging member as shown, and an actuating member 240 movable within housing 210. Additionally, system 200 may include an introducer such as endoscope 250 with image sensor 252 disposed at a distal region of the introducer as shown. Introducer 250 may be configured to be coupled to an intubation tube (e.g., an ETT for use during a TI procedure). In this context, "coupled to" includes an ETT being axially movable about or over the introducer. As shown in FIGS. 2B, 4A, and 4B, system 200 may further include cover 260 including channels sized and configured for receiving the first imaging member (e.g., laryngoscope baton 220) therein and at least part of the ETT and introducer (e.g., endoscope 250). As shown in FIGS. 4A and 4B, cover 260 may further include a distal region that includes member 268 that is configured to manipulate tissue (e.g., patient tongue) during an intubation procedure. Any of the covers herein may include a member similar to member 268 configured to manipulate tissue (e.g., patient tongue) during an intubation procedure. While additional exemplary aspects of system 200 for enhanced visualization and navigation during intubation are described in further detail below with reference to FIGS. 2A-2C, FIGS. 3A-3D, FIGS. A-4B, FIG. 5, and FIG. 6, it should be understood that the described aspects may be applied to other variations of systems and devices having other sizes, shapes, etc.

Handheld Housings

Exemplary housing 210 may be sized and configured to enclose various software and hardware components for performing robotic-assisted TI, such as electronic components (e.g., processor(s), memory, power source(s), motor(s), etc.) and/or an actuator(s) for guiding the introducer, such as during an intubation procedure. The housings herein may further be sized and configured to integrate the first imaging member (e.g., a video laryngoscope) and the second imaging member (e.g., endoscope) into a single, user-friendly portable and handheld system that may be operable and controlled by a single hand or a single user. Both the handheld housings herein (e.g., housing 210) and the integrated dual-video assemblies herein (which may include the handheld housing) may advantageously be sized and configured to be held by a single hand of a single operator, providing the benefits described herein.

The housings herein (e.g., housing 210) may be configured as a handheld housing that may be held ergonomically in the hand of a user. The handheld housing may be contoured (e.g., with finger grips, etc.) or otherwise configured for a particular hand (e.g., left hand, right hand), or may be suitable for either hand. For example, as shown in the front view depicted in FIG. 2A, the handheld housing may be configured for use with a left hand. In some variations, the housing may include one or more other ergonomic features, such as cushioning to improve user comfort (e.g., foam or rubber padding, silicone gel, etc.), frictional features (e.g., rubberized grip, textural features such as ribbing, etc.).

In some examples, the handheld housing may be between about 10 cm and 75 cm in length, such as between about 15 and about 45 cm in length, but may be any suitable size that is compatible with device ergonomics that is able to be held by a single hand of an operator. In some embodiments the housing is from 2 cm to 15 cm wide, such as from 4 cm to 10 cm wide. In some embodiments the housing is from 5 cm to 20 cm measured top to bottom, such as from 5 cm to 15 cm.

The housings herein (e.g., housing 210) may be made of any suitable rigid or semi-rigid material. For example, the housing may include plastic that is formed through a suitable injection molding process. In some variations, the housing may include one or more separate components (e.g., shells) that are coupled together through one or more suitable fasteners (e.g., epoxy or other adhesive, mechanical fasteners) and/or mating features (e.g., threaded or snap-fit or complementary features on different housing components). The housing may enclose, in an interior volume, various electronic components, actuator(s), and/or other aspects of the device, examples of which are described herein.

Electronics Systems

The systems or assemblies herein may include an electronics system (e.g., electronic system 214) that may include at least one processor and/or at least one memory device. At least a portion of electronics system 214 may, for example, be arranged in the housing and/or a display coupled to the housing described in further detail below. A memory device may store instructions (e.g., in the form of software, computer executable methods) for one or more processor to analyze images from the first imaging sensor and/or the second imaging sensor, and/or perform AI-based analysis of such images (with smart image recognition technology and/or machine learning) to automatically navigate the introducer into the trachea during intubation. The processor(s) may also be configured to perform automated control of the actuator in the device for guiding at least a portion of the actuating member and/or introducer for intubation assistance. The automated navigation may perform the intubation procedure in a user-friendly manner, with little user training or experience to enable successful intubation. Additional details of such AI or machine learning algorithms are described further below.

Electronics system, conceptually designated as exemplary electronics system 214, may further include other components for supporting the device, such as at least one power supply. In some variations, the power supply may include at least one battery as a self-contained power supply (e.g., to help facilitate device portability). Additionally or alternatively, the housings and/or display may include a power supply connector or port 211 that may enable a wired power connection, such as to an external AC or DC power supply. Additionally or alternatively, the housings may include a wired connection (e.g., cable) and/or wireless communication module for communicating with a free-standing video monitor. Furthermore, in some variations, the housings may include an emergency stop control (e.g., button) which halts automated robotic assistance of the device such as by intention of the operator (e.g., suddenly ceasing current to actuator(s), etc.). In some variations, the housings may further include a power button that controls powering the system on and off, and/or port(s) for downloading the images and updating software program(s).

Actuation Unit(s), Actuators, Actuating Members

The housings herein (e.g., housing 210) may include one or more actuators 216 configured to automatically guide movements of actuating member 240 for AI or robotic-assisted intubation while the introducer is coupled (e.g., releasably coupled) to an intubation tube. In the example of FIG. 2A, advancement of actuating member 240 may also extend the effective operating length or working length of endoscope 250. As described in further detail below, actuator(s) 216 may be integrated in the housing and exert its actuation on the actuating member 240 through a coupled interface, such that the generated movements are transmitted along the longitudinal axis of the actuating member and along the longitudinal axis of the endoscope 250 extending from the actuating member. One or more actuators 216 may additionally be included to operate and/or articulate the distal end of the endoscope 250, as further described below.

The device may include any suitable actuator and mechanical or electromechanical assemblies for controlling the actuating member 240 and/or the introducer. For example, exemplary actuator(s) 216 and associated controller(s) may include suitable drive electronics, one or more electrical motors, hydraulics, and/or pneumatics, as well as suitable mechanical assemblies, connections, joints, and/or controllers. For example, control assemblies, connections, and joints for controlling the actuating member and/or endoscope may include longitudinal elements with bidirectional push-pull cables, wire pulley assemblies, chain drives, hinges, slide-crank mechanisms, piezoelectric elements, pneumatic elements and assemblies, magnetic elements, adjustable couplings, sleeves, belts, gears, pushers, plungers, movable racks, compressions springs, translational rotary-to-linear and/or linear-to-rotary motion modules, gear drives, or other suitable motors and/or joints, etc. Other suitable fasteners and bearing surfaces may furthermore be included in actuator(s) assemblies 216.

Exemplary Actuator(s) 216 may be activated automatically and/or manually. For example, in some examples, actuator(s) 216 may be activated through one or more processors executing image recognition software instructions, in response to the processor(s) recognizing one or more anatomic landmarks through such image recognition techniques. This automatic activation may, for example, be part of a fully automated mode of the device. Additionally, or alternatively, actuator(s) 216 may be selectively engaged and/or disengaged in response to a user selection of one or more user interface elements. For example, actuator(s) 216 may be activated by selection of an AI operational button 280 or the like as shown in FIG. 2C and deactivated by selection of a STOP button 284 or the like as shown in FIG. 2C. It should be understood that the system may additionally or alternatively include other user interface elements to activate/deactivate a fully automated mode of the device, such as a toggle switch, touch-sensitive pad, touch screen, user interface icon on display screen, etc. In some variations, manual actuation of actuating member 240 (e.g., with a joystick or other user interface element, as described below) may instantly override the fully automated mode. In these variations, the fully automated mode may then be allowed to resume after the user presses AI operation button 280, for example. Additionally, or alternatively, the fully automated mode may resume after a predetermined period of time (e.g., period of inactivity or non-movement of the actuating member 240, predetermined duration of time, etc.) while in the manual assist mode. In yet other variations, a selected manual assist mode may override the fully automated mode as long as a clutch (e.g., button, switch, joystick, or other suitable selectable mechanism) is engaged, while release of the clutch button may allow the fully automated mode to resume.

Displays

As shown in exemplary FIGS. 2A-2C, any of the systems or assemblies herein (e.g., system 200) may optionally further include a display, such as display 218, such as a monitor screen, touch screen, or the like. The display may be configured to display image data and/or a user interface. For example, the display may be configured to display single-channel images from only the first image sensor (e.g., a laryngoscope image sensor 222) or only the second image sensor (e.g., introducer image sensor 252). As another example, the displays herein may be configured to display multi-channel images from both the first and second image sensors (e.g., 222 and 252), such as in a split screen and/or picture-in-picture arrangement of images from the, for example only, laryngoscope and/or endoscope image sensors. In some variations, the display may be configured with default or preprogrammed display sequences. As one example of a default display sequence, the display may be configured to initially display a video feed or signal from a video laryngoscope to provide visual feedback of initial entry into the patient's airway (e.g., upper airway) and/or of identified anatomic structure(s), then automatically transition to display a multi-channel set of images (e.g., split screen, picture-in-picture) from an endoscope image sensor (e.g., 252) and/or an laryngoscope image sensor (e.g., 222) upon activation of AI-based actuation (either automatically or through manual activation, as described above) and/or upon pressing a selectable user interface element on the device and/or display. In some variations, other toggling of video feeds from the various image sensors may be accomplished through certain preprogrammed operation of user interface elements (e.g., pressing a picture-in-picture button or icon twice or several times in succession may result in a full image of the patient's trachea and intubation tube placement (or other anatomy) as provided from the endoscope image sensor 252).

In some examples, the displays herein may be coupled to the housing 210 or other housing herein (e.g., on a proximal portion of the housing). The display may include any suitable display elements (e.g., LCD). In some variations, the display may be coupled to the housing via a rotatable or pivoting coupling, such that it may swivel around a longitudinal axis and/or tilt around a vertical and/or lateral axes and be viewable from multiple angles. Alternatively, the systems herein may include a multi-faced (e.g., dual-sided) display to permit viewing of displayed content from multiple angles simultaneously. In any of the embodiments herein a display coupled to a handheld housing may be portable sized, such as between about 8 cm and 15 cm high and between about 10 cm and about 18 cm wide, but the display may be any suitable size and/or shape.

Additionally, or alternatively, any of the systems herein may include and be communicatively coupled to a remote display that is not part of an integrated assembly. For example, the systems herein may include one or more ports in any of the housings herein for a wired communication to a display device. As another example, the systems may include a wireless communication module and antenna to communicate content for display to other screens (e.g., via cellular mobile network, WiFi, etc.).

First (Elongate) Imaging Member (e.g., a Laryngoscope)

Any of the integrated dual-video systems or assemblies herein may include a first imaging member (e.g., a video laryngoscope), which may include an elongate flexible body and a first image sensor (e.g., a video camera) disposed at a distal region of the elongate body. Any of the first imaging members herein may also be referred to as first elongate imaging members, indicating in general that they have an elongate configuration. For example, as shown in exemplary FIGS. 2A-2C, system 200 may include a first imaging member (e.g., video laryngoscope). The first imaging member may include a baton 220 (or other elongate member) extending distally from housing 210, as shown. Baton 220 may include a high-resolution image sensor(s) at a distal region for providing video images (e.g., video camera), one or more light guides for providing illumination to the image sensor field of view, and electronic signal wires for transmitting video data or images for processing and/or display on the display 218 (or other suitable display). The image sensor(s) 222 may be located at a distal end of the elongate member, and may be adapted to provide a relatively wide angle of view for enlarged and clear visualization of the patient's anatomy in both axial and horizontal planes during an intubation procedure. The relatively wide angle of view and the angular position of the first imaging sensor (relative to the second image sensor) can help reliably visualize and identify critical anatomical landmarks in an upper airway, thus enhancing the navigation of the introducer as it is moved distally relative to the first image sensor. The combined use of the first and second imaging members, the optionally large angle of view and the placement and maintenance of the video cameras of the first and second imaging members in close axial proximity to each other and to the glottic opening, provide for the shortest, quickest navigation pathway for the introducer and ETT to the vocal cords and trachea, as described in more detail below. In some merely optional but not limiting examples, a first image sensor(s) of a first imaging member may have a wider angle of view than a second image sensor of an introducer. Accordingly, a first imaging member may provide for an enlarged and clearer image of patient's anatomy compared to conventional devices, which may facilitate a faster, more reliable AI image recognitions and/or initiation of robotic-assisted control and movement of the introducer using the system. Any of the image sensor(s) herein may optionally include a charge-coupled device (CCD), CMOS sensor, and/or other suitable sensor(s), and may be combined with any suitable optical elements such as an objective lens, etc. In some embodiments, first and second video cameras of the first and second imaging members may have the same angle of view, while the first image sensor can still provide visualization of a larger anatomical area relative to the second image sensor by being maintained proximal or behind the second image sensor as the introducer is advanced distally toward a glottic opening, for example. In some embodiments still, the first video camera may have the smaller angle of view than the second video camera, but the first image sensor can still provide visualization of a larger anatomical area relative to the second image sensor by being maintained proximal to or behind the second image sensor as the introducer is advanced distally toward a glottic opening, for example. Exemplary methods of use that include utilizing first and second simultaneously presented video signals from the first and second video cameras are included in more detail below.

In any of the systems herein, a first imaging member may comprise a laryngoscope, which may include a baton or other elongated member that is between about 10 cm and about 15 cm long, but may be any size appropriate for an adult and/or pediatric patient population. As is described below, the systems herein may optionally include universal handheld housings that are adapted to be able to be used interchangeably with first imaging members of different sizes for different patient populations (e.g., adult and pediatric), which provides more functionality to the universal handheld housing. As shown in exemplary FIG. 2A, exemplary laryngoscope baton 220 may generally taper in diameter as it extends away from the housing 210, and/or may gently curve or flare to accommodate imaging components, and/or provide for better angling during an intubation procedure, etc. However, first imaging member 220 may have any suitable shape and size for use with patient anatomy. In some examples, the first imaging member (e.g., which may include a laryngoscope baton), may be flexible and may have an at-rest curved configuration, and in some examples it may have a straight or substantially straight configuration that is adapted to be bent within the cover. First imaging member 220 may be either removably or releasably coupled to, or integrally or permanently coupled to housing 210 (e.g., intended for reuse). For example, first imaging member 220 may remain sterile between uses by use of a disposable cover 260 (as further described below), or may be sterilized between uses with a suitable disinfectant, etc. Alternatively, in some variations, first imaging member 220 may be modular, or detachable from housing 210 (e.g., snap-fit connections, etc.), and may be disposable and/or swapped out and replaced by different first imaging member 220 between different uses of system 200. For example, first imaging member 220 may be swapped and replaced by a different first imaging member 220 to avoid the need to sterilize the baton between uses. As another example, first imaging member 220 may be removed to facilitate separate sterilization between uses. As another example, different first imaging members 220 may have different lengths, diameters, and/or shapes for different types of patients (e.g., adult patients, pediatric patients), such that first imaging member 220 may be replaced by a different first imaging member 220 of a different desired size depending on the patient and/or situation. Furthermore, as described in further detail below, a cover (such as cover 260) may be sized appropriately (e.g., with a channel defining a lumen of a suitable diameter and/or length) for the dimensions of first imaging member 220.

Actuating Member and Introducer (e.g. Endoscope)

In some examples, the integrated assembly or system may optionally include one or more actuating members as well as an introducer. For example, in exemplary FIGS. 2A-2C, device 200 may include an actuating member 240 and an introducer (e.g., endoscope 250) extending from the actuating member 240. In this non-limiting example, actuating member 240 and endoscope 250 may, for example, be joined or couplable together end-to-end to form a flexible member.

Generally, a combination of actuating member 240 and endoscope 250 or other introducer may include a flexible insertion tube (or rigid video stylet or the like) to engage with an intubation tube, at least one image sensor 252 arranged at a distal end of the introducer 250, and an articulable distal tip of the introducer 250 that may be controllable by one or more tensioning elements such as one or more pullwires secured to a distal region of the introducer, or other suitable control mechanism(s).

For example, the introducer (e.g., introducer 250) may include a high resolution image sensor(s) or video chip camera module at its distal end, such as is shown in exemplary FIG. 2A, such as a CCD or CMOS image sensor(s), an objective lens, and/or other suitable optical configurations. In an exemplary embodiment, the image sensor may, for example, be between about 2 mm and about 4 mm in size and provide a wide angle of view (e.g., at least 90 degrees, at least 180 degrees, at least 270 degrees, or 360 degrees, etc.). One or more light guides (e.g., carrying LED or other illumination) may pass through the shafts of the actuating member and introducer to provide illumination during an airway management procedure. Signal wires along the shafts of the introducer may carry images or image data from the image sensor to an image processor, which may optionally be disposed in the housing and/or a display, or which may be disposed in an external device. Furthermore, the distal end of the introducer 250 may include a bendable, articulating structure (e.g., with jointed segments) that may be controlled by angulation pullwires or tensioning cables or other suitable mechanism(s). Such angulation wires may, for example, control up-down and right-left steering movements of the articulating tip of the introducer 250.

At least a proximal end of optional actuating member 240 may be coupled to and/or located within housing 210 and controlled by one or more actuators. Actuating member 240 may be longitudinally advanced (e.g., at least partially out of housing 210) and retracted proximally back along a longitudinal axis and/or rotated by one or more actuators 216, and therefore control advancement, retreat and/or rotation of introducer 250. In some variations, actuating member 240 may extend the working length of introducer 250, in that the advancement of actuating member 240 may enable the distal end of introducer 250 to be located farther distally than introducer 250 is capable of doing so alone. Furthermore, actuating member 240 may be retractable inside the housing 210, such as, for example, with selectable button 290 as shown in FIG. 2C.

In some variations, actuating member 240 and introducer 250 may be integrally connected, such as in a permanent fashion. In other words, actuating member 240 and the introducer may optionally be structurally and functionally integrated. Thus, in some variations, an entire flexible member including both actuating member 240 and introducer 250 may remain coupled to housing 210, and the entire flexible member (and potentially the entire device 200) may be fully sterilized between uses. In other variations, actuating member 240 may be detachable from housing 210, such that actuating member 240 and introducer 250 may be sterilized separately from housing 210. For example, actuating member 240 may be releasably coupled to housing 210 through connector fittings, fasteners, mechanical interfit (e.g., threads, interference fitting), nesting, or in any suitable manner In some variations, a disposable protective sheath or other cover may be removably placed over at least introducer 250, which may eliminate the need for full sterilization of the actuating member, introducer, and/or entire device between uses. In other variations, actuating member 240 with its connections to user interface device 270 (e.g., including guide 217 and/or a control member 274 such as a joystick as shown in FIGS. 2C and 3, for example) may be integrated in a single module, which removably attaches to housing 210 and to actuating controls 216 (e.g., snap-fit, "plug-and-play" connections, etc.). In another variation, the actuation controls, in full or in part, can also be included in such module. Such an integrated module, with either permanent or detachable connection to introducer 250, can easily be removed from housing 210 and replaced with a new instance of a similar module and/or swapped out for a new and different module that contains, for example, a different actuating member 240 with a different outside diameter, length, etc. This can further allow the housing to function as a universal handheld that is adapted for use with introducers of different sizes, which may allow a single handheld housing to be used to treat different patient populations (e.g., adults and pediatrics).

Alternatively, in some variations, any actuating member and any introducer (e.g., an endoscope) herein may be detachable from one another. An actuating member and an introducer may be coupled together through connector fittings, fasteners, electromechanical interfit (e.g., threads, interference fitting), bands, nesting, or in any suitable manner Once coupled, an actuating member and an introducer may function as a continuous single member. For example, introducer 250 may be removably attached from actuating member 240 or housing 210 such that introducer 250 may be disposable. In this example, introducer 250 need not be sterilized, as it may optionally be discarded after use.

External surfaces of actuating members and introducer may optionally be covered in a coating (e.g., a polymeric material) that provides for an atraumatic, biocompatible, and watertight smooth surface. In some embodiments, an actuating member and/or an introducer may include an outer diameter that is between about 2.5 mm and about 7.0 mm. The proximal part of an actuating member (e.g., between about 0.5 cm and about 6.0 cm long) or even the whole length of an actuating member may, in some variations, have a larger outer diameter as needed to accommodate various connections to an actuator(s) in a housing and/or the user interface device (as further described below). The total combined length of the actuating member and introducer may be, for example, between about 30 cm and about 70 cm. In some variations, an actuating member may be between about 10 cm and about 40 cm long, and the introducer may be between about 20 cm and about 30 cm long. However, diameters, and lengths of an actuating member and/or an introducer may be varied for different applications (e.g., adult vs. pediatric patients, etc.). For example, a variation of the device that may be suitable for assisting nasotracheal intubation may include an introducer that is longer, such as between about 20 cm and about 60 cm, which may contribute to an overall combined length between an actuating member and an introducer that is between about 30 cm and about 100 cm long. Other exemplary structural aspects of actuating members and introducers are described in further detail below.

Actuating Members

Any of the integrated systems or assemblies herein may optionally include one or more actuating members, and the disclosure that follows may apply to any actuating members herein. At least a proximal end of exemplary actuating member 240 may be located in housing 210 and/or display 218. Actuating member 240 may be driven in multiple degrees of freedom to result in corresponding motions of the introducer (e.g., endoscope 250). For example, actuating member 240 may be actuated via an electromechanical coupling in linear advancement (forward-back along a longitudinal axis), and axial rotation (rotation around a longitudinal axis). Other actuation at or near actuating member 240, such as via guidewires described above, may cause the distal end of the introducer to additionally articulate in up-down and/or right-left tip movements.

Collectively, actuating member 240 and the introducer may be constructed such that actuation and movements at actuating member 240 may result in transmission of all desired degrees of freedom to the introducer Similar to that described above, any suitable actuator(s) 216 and accompanying control systems for driving actuating member 240 may be included in the device, such as drive electronics, one or more electrical motors, hydraulics, pneumatics, and/or various mechanical parts (assemblies, connectors, joints, controllers, etc.) as suitable. Control assemblies, connections, and joints may be configured for smooth and precise transmission of the desired actuated mechanical motions along the actuating member to the introducer and the distal articulating tip of the introducer.

As shown in exemplary FIG. 2A, in some variations actuating member 240 may travel along a designated path within housing 210. For example, as shown in FIG. 2C, actuating member 240 may be arranged along guide 217 in housing 210 (or on a surface of the housing 210). Guide 217 may, for example, include a guiding channel (e.g., at least between about 0.5 cm to about 1.0 cm wider than the actuating member 240), or any suitable rail, track, or other guiding structure). In other words, actuating member 240 may travel within the guiding channel as it is driven by the one or more actuators 216 described above in a fully automated mode of the device. Although guide 217 is shown in FIG. 2C as curved, it should be understood that in other variations guide 217 may be straight or another suitable shape that fits within housing 210.

Figure 3B:
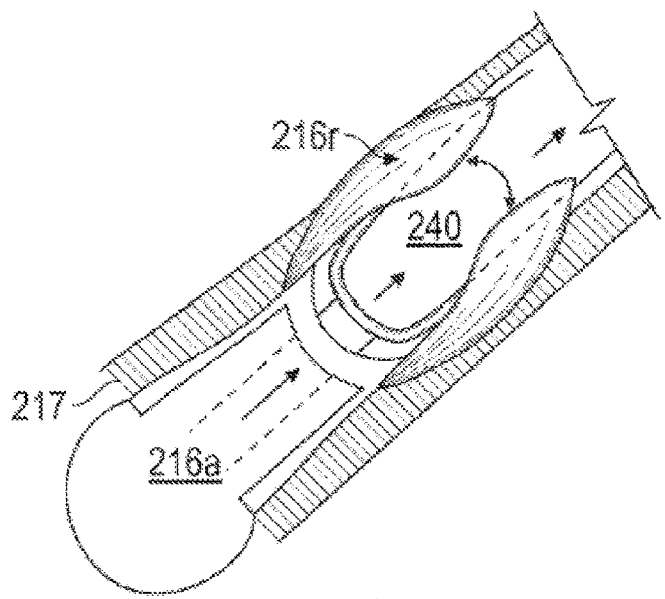
FIG. 3B depicts a perspective view of an example variation of an automatic actuation system for guiding an actuating member in a device for assisting navigation and/or intubation in a patient.
Figure 3C:
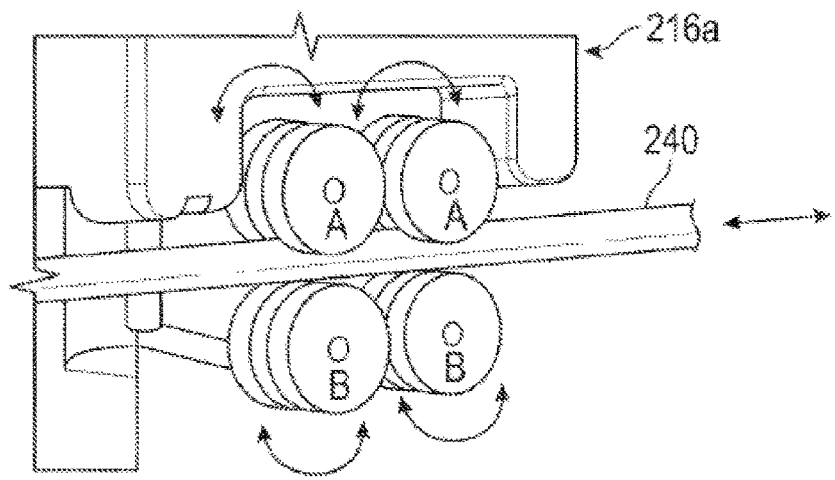
FIGS. 3C and 3D depict example variations of actuation units for guiding an actuating member in a device for assisting navigation and/or intubation in a patient.
Figure 3D:
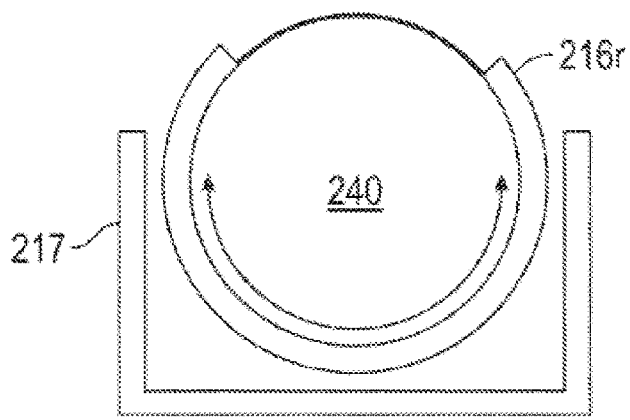
Figure 4A:
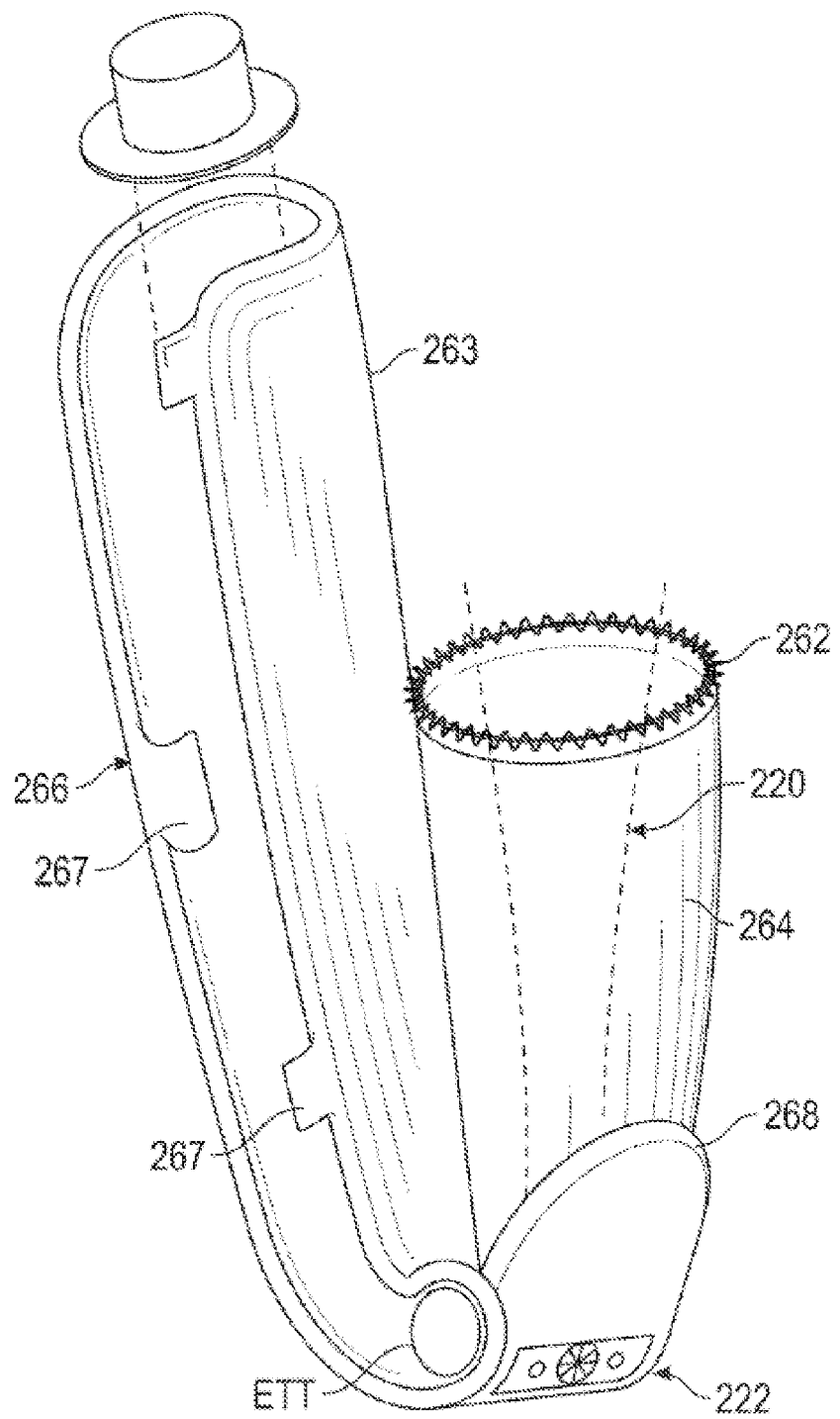
FIGS. 4A and 4B depict example variations of a cover in a device for assisting navigation and/or intubation in a patient.
Figure 4B:
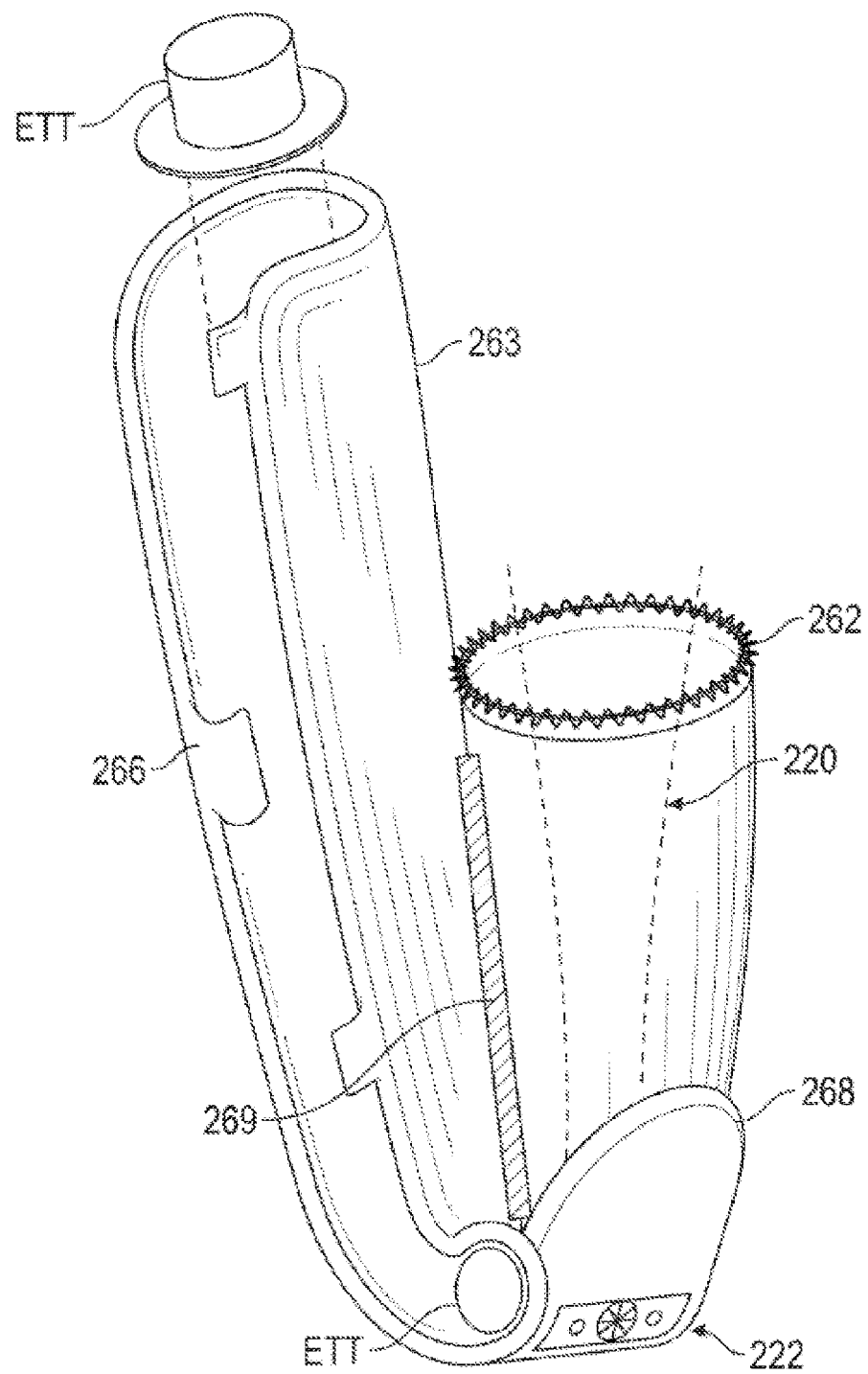

FIGS. 3B-3D illustrate exemplary variations of actuators that are configured to move the actuating members herein along a guide. FIG. 3B is a schematic illustration of axial actuator 216a configured to move actuating member 240 in an axial or longitudinal direction (e.g., in advancement and/or retreat), to thereby axial move the introducer in a similar fashion. For example, as shown in FIG. 3C, axial actuator 216a may include one or more matched pairs of opposing driving wheels which engage actuating member 240 via grooves, frictional elements, and/or the like. The driving wheels in each matched pair of driving wheels (wheel A and wheel B) may be located on opposite sides of actuating member 240 or the introducer such that their synchronous rotation in opposite directions urges actuating member 240 of the introducer forward and backward in an axial or longitudinal direction, such as along guide 217. Other suitable mechanisms, such as one or more of slider crank systems, belt or pulley systems, plunger actuators, corkscrew mechanisms, etc. may additionally or alternatively provide axial actuation of actuating member 240. Furthermore, as shown in FIGS. 3B and 3D, one or more actuator connections to rotational actuator 216r may also be coupled to actuating member 240. The rotational actuator 216r may include one or more pullwire or other tensioning element attachments coupled to actuating member 240 configured to control a side-to-side, or left and right, movement, similar to that described below with respect to FIG. 3B. However, any other suitable mechanism such as rollers, etc. may be used to automatically actuate the rotational movement of actuating member 240 and hence the guiding introducer.

Additionally or alternatively, actuating member 240 may travel within guide 217 as actuating member 240 is driven manually such as via the user interface device 270, a touch screen, voice commands, etc., such as in a manual assist mode. For example, as shown in FIG. 3A, user interface device 270 (e.g., including a control member 274 such as a joystick) may be coupled to actuating member 240. User interface device 270 may be engaged within control member guide 272 as shown in FIG. 2C and FIG. 3A, which may generally follow or parallel the trajectory of guide 217 for the actuating member 240. User interface device 270, including a control member 274, such as a joystick may be coupled to actuating member 240 as shown in FIG. 3A via control wires 276 attached at connection points 278 and 279 (e.g., with fasteners, welding, or in any other suitable manner). For example, the top connections 278 between control member 274 and actuating member 240 may control a manual forward movement (F) as a user manually manipulates (e.g., pushes and/or pulls) the control member 274 forward and backward within the guide 272. As another example, the side connections 279 between the control member 274 and actuating member 240 may control a side-to-side, or left and right movement (L) and (R) as a user manually manipulates (e.g., pushes side to side) the control member 274 within the guide 272. Accordingly, user interface device 270 may allow for a manual assist mode (e.g., manual advancement and/or rotation of the actuating member 240 and hence the introducer (e.g., endoscope 250), but with automated actuation of the endoscope's distal articulated tip). These connections 278 and 279 may remain inactive in a fully automated mode. In some variations, the manual assist mode may be confirmed with a user interface element 282 (e.g., button) shown in FIG. 2C, whereby selection of the user interface element 282 may cause the device to enter the mode in which automated movements are limited to articulation of the distal tip of the introducer (e.g., endoscope 250), while linear and/or rotational endoscope movements are controlled manually as described above (e.g., with user interface device 270). The user interface element 282 may, for example, help the operator activate the manual assist mode if such a mode is desired.

In some variations, any of the actuating members herein may be self-expanding. For example, as shown in FIG. 2A, actuating member 240' may include a self-expanding construction, such as including interlocking rings and/or spiral elements that transition from a compressed state to an extended state. Similar to that described above, actuating member 240' may be oriented along a guide 217' and actuated with an actuator(s) 216' and/or manually with a suitable user interface device. Although actuating member 240' is shown in FIG. 2A as compressed within a straight guide channel, it should be understood that other shapes of guide channels may be possible.

Furthermore, at least a portion of one or more of any actuating member, any actuator, a user interface device, and/or a guide may be in a module (e.g. display 218) coupled to the housing 210. For example, as shown in FIG. 2A, in some variations, the proximal end of actuating member 240" may terminate in the display, where one or more actuators 216" similar to that described above may automatically move (axially and/or rotationally) actuating member within a guide 217" that is in the display and articulate the tip of the endoscope, as described above. Additionally or alternatively, in some variations, the proximal end of actuating member 240 may terminate in the display or module, where a user interface device similar to that described above may be used to manually move (axially and/or rotationally) actuating member 240" within a guide that is in the display. Furthermore, additionally or alternatively, in some variations, the proximal end of an actuating member 240" may terminate in the display, where the actuating member may self-expand in a manner similar to actuating member 240' as described above. For example, the actuating member 240" with a proximal portion in the display may be straight and axially aligned with the endoscope 250, such that self-expansion of the actuating member 240" results in easier extension of the endoscope working length.

Introducers (e.g., Flexible or Rigid Endoscope)

Figure 5:
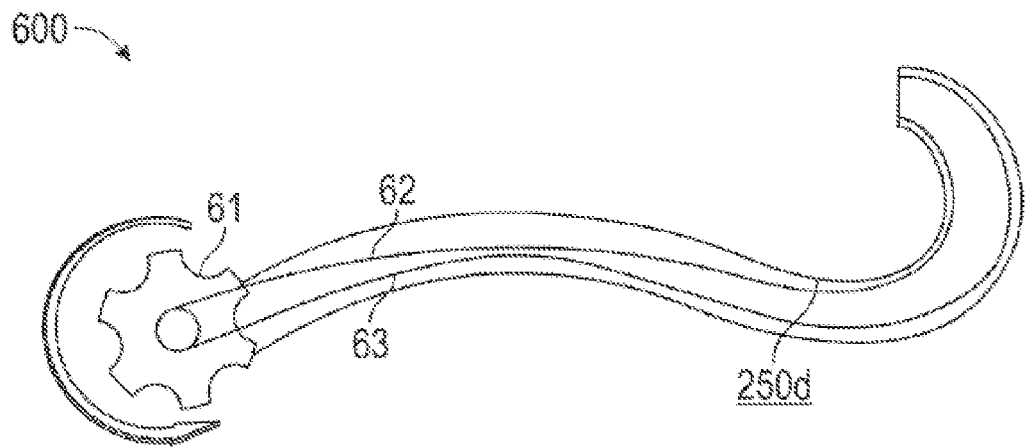
FIGS. 5 and 6 illustrate example variations of an automatic actuation system for articulating a distal end of a scope member in a device for assisting navigation and/or intubation in a patient.

Any of the dual-video integrated systems or assemblies herein may include an introducer that is sized such that it can be used to guide the delivery of an intubation tube such as an ETT into a trachea, for example. A ETT may be advanced over any of the introducers herein. Any endoscope described or shown herein may be considered to be a mere example of an ETT introducer. It is understood that the description of any endoscope or scope herein may be considered to inherently be a description of a more general introducer, as that term is used herein. In an example herein, introducer 250 may be an endoscope, such that endoscope 250 may be removably coupled (e.g., telescopically engaged) to an intubation tube for an intubation procedure. Endoscope 250 may be configured to enter and navigate inside the patient's airway, and serves as an introducer for ETT advancement during an intubation procedure. As described above, the introducer may have multiple degrees of freedom controlled by driving an actuating member, including longitudinal forward-back movement, axial right-left rotation, and up-down, and right-left articulating motions at its distal end. For example, as shown in FIG. 5, an arrangement 600 including the distal end of introducer 250 may include one or more sets of antagonistic cables 62 and 63 extending from a navigation wheel 61 towards the distal end region 250d of introducer 250. Each set of antagonist cables may, for example, correspond to a degree of freedom for the articulating tip of introducer 250.

Figure 6:
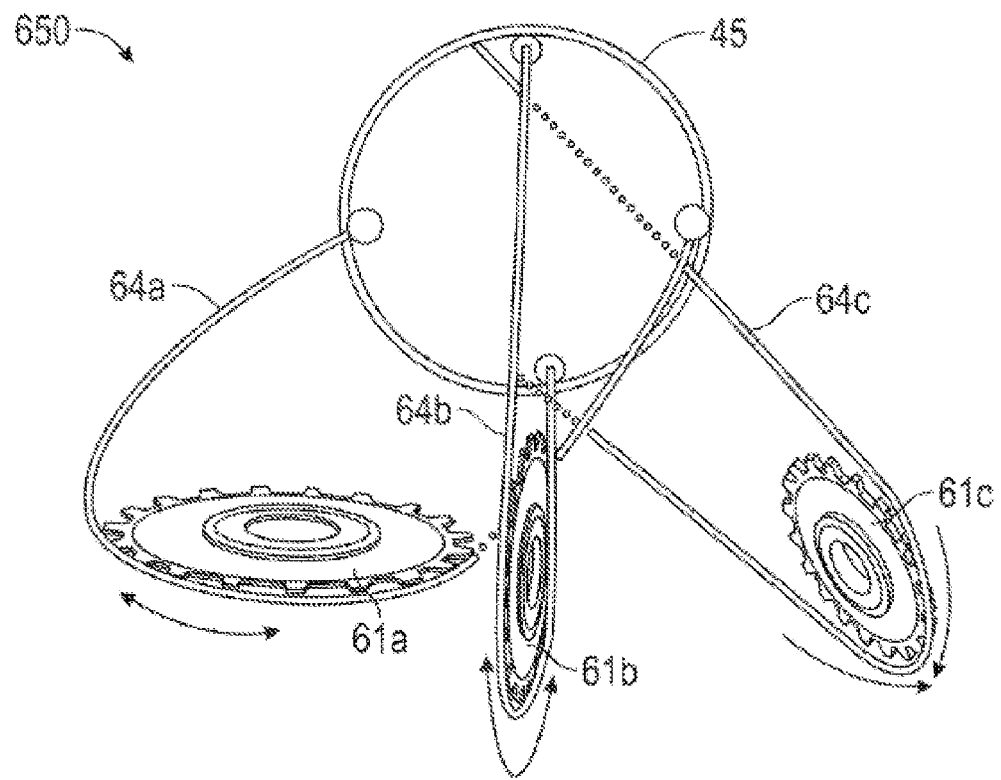

As shown in the exemplary FIG. 6, for example, an arrangement 650 may include at least a first set 64a of antagonistic cables operated by a navigation wheel 61a to control right-left articulation, a second set 64b of antagonistic cables operated by a navigation wheel 61b to control up-down articulation, and/or a third set 64c of antagonistic cables operated by a navigation wheel 61c to provide for tensioning of actuating member 240. An arrangement for articulating scope tip movement may alternatively include only one or two of these sets (e.g., only a set 64b of antagonistic cables operated by a navigation wheel 61b to control up-down articulation). The cables may, for example, be coupled to the actuation portion 240 via mechanical fasteners, welding, etc. The navigation wheels 61a-61c may include wheels, sprockets, rotation knobs, and/or the like. In some variations, the length of the distal tip bending section may be between about 4-5 cm, and the articulation (steering) of the tip at the bending section may be between about 120 degrees and 180 degrees in all directions (up-down, right-left). Furthermore, the axial rotation of the introducer may be between about 90 degrees and about 180 degrees in both right and left directions.

In some variations, an introducer (e.g., an endoscope) includes a flexible member with optical, electrical, and mechanical functionality as described above, including transmission of light, video capture, mechanical actuation, and distal tip articulations. Alternatively, in some variations, the introducer may include a video stylet. The stylet may, for example, have the same optical, electrical, and mechanical functionalities similar to a flexible scope member, but may be more rigid to due to material and/or structure (e.g., a more rigid construction including metal). In some variations, at least a portion of the stylet may be malleable. Use of a rigid video stylet instead of a flexible member may be useful, for example, in some applications in which greater torsional rigidity is desirable to permit better transmission of linear and rotational movements between an actuating member and the introducer, easier maneuverability around the patient's airway (e.g., obstructing glottic lesions), smoother advancement during insertion and navigation in patient anatomy, and easier advancement of the intubation tube.

As is stated herein, the endoscopes herein are examples of more generalized introducers for the intubation tubes, and the introducer may (e.g., an endoscope) or may not include an image sensor. As such, any description herein of a device or system that includes an endoscope or scope is understood to include an introducer, which optionally may not include an imaging sensor.

Transitional Region

Any of the integrated assemblies or systems herein may optionally include a transitional region or segment between an actuating member and an introducer. The transitional region may have intermediate stiffness and/or other gradual changes in structural characteristics, to help ensure smooth and uninterrupted transmission of actuation from an actuating member to the introducer. In some variations, a transitional region may additionally or alternatively include a series of successively increasing flexible segments and/or a coil spring to transition from a stiffer actuating member to a more flexible introducer.

Alternatively and/or additionally, in variations such as where an actuating member and introducer are removably coupled, a relatively stiff transition region (e.g., between about 1-2.5 times the length of the outer diameter of an actuating member and/or an introducer) may be helpful between the actuating member and the introducer to restore continuity of electromechanical functionality and/or other functions. The transitional region may include coupling that provides the same structural and task functionality (including uninterrupted transmission of light, video capture/analysis, and mechanical actuation, etc.) as described elsewhere for variations in which an actuating member and introducer are integrally coupled. Optical/electrical functionality may be maintained between the actuating member and the endoscope with one or more suitable mating connectors (e.g., connectors associated with respective routing PCBs), etc. Control of the distal tip may also be maintained through mechanical solutions such as coaxial cable connectors, push-button latches, pin and socket arrangements, wire lugs, plates, pins, screws, articulating joints, etc.

Other Structural Features

Any of the integrated systems or assembles herein may include one or more structural features that are adapted to help prevent buckling and/or loop formation during its forward-back advancement along the linear axis and/or rotation, which helps improve smooth transmission of movements from the actuating member to the introducer. In some variations, shaft stiffness and torqueability may be increased by incorporating flat, spiral interlocking metal bands with gaps therebetween (e.g., bands under an outer polymer cover) to maintain flexibility. These spiral bands may be covered by fine strands of stainless steel wire or other suitable material, braided into a tubular mesh and covered with an extruded polymer layer to create a smooth outer surface. Some exemplary solutions for improving advancement ("pushability") and rotation ("torqueability") are described in further detail below.

For example, an actuating member and/or the introducer may be guided through a somewhat continuous physical guide, such as a guide channel (e.g., similar to an overtube environment). This guide channel may help constrain the actuating member and/or the introducer and keep the combined length taut during maneuvering, thereby reducing kinks and other issues. For example, as described above, an actuating member 240 may be constrained in a guide 217 in the housing 210 and/or display 218, and the endoscope 250 may be lodged within an intubation tube, which in itself provides a rigid guiding channel for the endoscope 250. Additionally, as described below, the endoscope 250 may be constrained in an intubation tube channel 266 in the cover 260. Furthermore, as described in further detail below, the overtube environment may provide an active channel in which manipulation (e.g., manual manipulation) of the intubation tube may be easily performed, even while maintaining automatic, robotic-assisted guidance of the endoscope.

Furthermore, the surrounding intubation tube and/or the cover may help constrain the introducer into a straight path generally aligned with the patient's airway during intubation, which further reduces buckling and/or loop formation within the actuating member and/or introducer.

Other structural features may help reduce friction. For example, a guide (such as guide 217) for the actuating member, an actuating member itself, and/or the introducer itself, may be lubricated (e.g., with long-lasting commercial lubricants) and/or having an outer surface of low-friction materials to provide for decreased friction during actuation of the actuating member.

Additionally or alternatively, an actuating member may have increased shaft stiffness that may help prevent buckling and loop formation during its linear advancement and rotation inside the curved trajectory of the guide. For example, actuating member 240 may be stiffer than introducer 250, which may be softer and more flexible to better facilitate maneuvering. In some variations, shaft stiffness along the length of the combined actuating member 240 and introducer 250 may be varied by varying the outer layer material composition of actuating member and/or introducer 250. For example, the outer base layer may include a polymer with two types of resin, and the polymer may be extruded over a wire mesh forming an outer structure. The stiffness may be varied by varying the composition of the combined resin, and the resulting polymer layer may further provide an atraumatic, biocompatible, and watertight surface. Shaft stiffness may additionally or alternatively be varied with an adjustable shaft stiffening coil wires, or other suitable mechanical elements. In some variations, shaft stiffness may additionally or alternatively be increased at actuating member 240, making at least part of actuating member 240 have a larger outer diameter. For example, the proximal end of actuating member 240 may have a flared diameter, which may also advantageously allow for increased operating surface with actuator(s) 216.

Covers

Any of the systems and assemblies herein may further include a cover (e.g., cover 260) which allows for and is adapted to provide an integrated dual-imaging enhanced visualization and navigation system that is adapted to be held and controlled by a single hand of a single operator. Covers herein may be configured to be advanced over a tongue of the patient both above the epiglottis of the patient (e.g., in or near the vallecular) and under the epiglottis of the patient, providing for versatile placement of the cover. Additionally or alternatively, a cover may be preferentially configured for placement either above or below the epiglottis. In some variations, such as that shown in FIGS. 4A and 4B, cover 260 (or any other cover, such as the cover shown in FIGS. 17A-17G) may also include a displacement member 268 configured to facilitate retraction of a patient's tongue, thereby improving the pharyngeal space to improve scope movement inside the airway. The displacement member may be, for example, angled, linear, curved, or otherwise shaped to be placed inside a patient's mouth in an atraumatic manner In an example variation, the displacement member may be between about 3 cm and about 4 cm wide (e.g., for adult patients, and suitably smaller for pediatric patients).

As shown in FIG. 4A, the cover may comprise two sections, including a first channel (e.g., 264) and a second channel (e.g., 266). First channel may include a lumen that is sized and configured to receive a first imaging member therein (e.g., a laryngoscope baton), and second channel may be sized and configured to releasably secure an intubation tube (e.g., ETT) thereto and restrict movement of the tracheal tube relative to the cover in at least one direction. The channels may optionally be form fit to the received first imaging member and tracheal tube. First channel 264 may be adapted to be releasably coupled to, such as snap onto, housing 210 at connection 262, thereby removably attaching to the housing 210. In some variations, the first channel may be between 15 cm and 20 cm long, and angulated forward between about 4 cm and about 6 cm from the tip in a manner and direction that will maximize the view of different parts of the patient's upper airway anatomy (above the vocal cords) and glottic structures to enhancing visualization and movement of the introducer. However, these dimensions may be different for covers that are adapted for use with pediatric patients.

Second channel 266 is adapted to be releasably secured to the intubation tube (e.g., ETT), which may be disposed about the introducer (e.g., a preloaded ETT). The intubation tube channel may function to provide a mechanism for secure positioning of the intubation tube close to the displacement member 268. The intubation tube channel 266 may optionally be configured to be coupled to (e.g., snap onto) the housing 210 at connection 263. The intubation tube channel may further include one or more latches, clips, or other fasteners 267 to help retain the intubation tube within the intubation tube channel. In an example variation, the intubation tube channel may be between about 15 cm and about 30 cm long for adult patients and about half this length for pediatric patients. Various sizes (e.g., diameters) of intubation tube may be accommodated within the intubation tube channel 266. Furthermore, the second channel (intubation tube channel) need not define an internal lumen, but rather may be partially open on its side (e.g., with a longitudinal slot) to allow intubation removal from the cover when intubation has been completed. For example, the second channel may comprise a cross sectional configuration that is semi-circular, or with a groove or depression formed therein (also see 1713 in FIG. 17A) that is sized and configured to be releasably secured to an ETT.

In some examples, as shown in FIG. 4B, intubation tube channel 266 and first imaging member channel 264 may optionally be detachable from one another, such as along detachable joining region 269 with one or more connectors, perforations, etc. This may be useful, for example, as one of the options to enable a laryngoscope to provide an effective video laryngoscopy only back-up intubation option, in the event that AI navigation fails or become problematic. For example, intubation tube channel 266 may be detached along joining region 269 and removed, which allows a first imaging member and remaining portion of cover 260 to be used in a conventional manual video laryngoscopic intubation manner, where the intubation tube is manipulated by an operator outside of cover 260 (it should be understood that detaching the intubation tube channel 266 may not be required for all the patients if a preloaded intubation tube can be pushed through the intubation tube channel 266 of cover 260 into the patient's trachea). In another back-up intubation option, intubation tube channel 266 of the cover may be used for a combined video laryngoscopy—flexible endoscopy technique, where one operator performs video laryngoscopy, and a second operator manually performs flexible video endoscopy-assisted intubation. In yet another variation of a back-up intubation technique, detachable introducer 250 (or any other introducer herein) may be manually used as an intubation tube introducer to facilitate intubation tube placement into the trachea.

At the distal end of cover 260, the two channels 264 and 266 may terminate adjacent to and substantially axially aligned with each other, such that the image sensors of the first imaging member and the introducer are very near to one another. In this manner, the location of the distal end of the intubation tube (optionally coaxial and surrounding introducer 250) may be better localized to the field of view, thereby improving the ability to place introducer 250 and the intubation tube. Additionally, the dual channel arrangement can allow for a shortest distance of introducer robotically controlled movement to the glottis and into the trachea (compared to the other approaches where an introducer is separately advanced over a longer total distance), thereby resulting in quicker and more successful intubation on the first attempt. Dual channel covers or blades may result in the first imaging member and the introducer assuming or having similar curvatures along the length of the cover, which is shown generally in, for example, FIGS. 17C and 17D.

The integrated dual-image sensor systems and assemblies herein are generally adapted such that when the introducer or second imaging member (optionally a housing thereof) is releasably coupled to the housing, the first and second image sensors are disposed or maintained at an initial distance relative to one another, which may optionally but not necessarily provide predictable starting locations for the image sensors relative to one another. As used herein, being disposed or maintained at an initial distance from each may refer to any frame of reference and may include any spacing therebetween in space. For example, the image sensors may be maintained at a horizontal and axial distance relative to each other. In some examples, the sensors may be aligned in one frame of reference but still maintained at a distance from one another with a different reference point or axis. For example, in some exemplary embodiments, first and second image sensors may be substantially axially aligned with each other (in the proximal-distal direction), and spaced at some distance laterally or horizontally from each other. In these examples, the sensors are considered to be disposed and maintained at an initial distance from one another even though they are axially aligned. In some exemplary embodiments, the two image sensors may be initially substantially axially aligned with each other when assembled even if there is some minimal axial offset. The images sensors may be quite close to each other, and in some embodiments, the two image sensors may be maintained relative to each other such that the axial distance between the two sensors is not greater than 3 cm when the second imaging member (which includes an introducer) is releasably coupled to the housing. The actual distance between the sensors may be different than an axial spacing therebetween (if there is an axial spacing) due to a natural horizontal lateral offset of the two sensors when assembled together. When integrated into an assembly, a single hand of the operator can hold the integrated system with the two image sensors disposed or maintained at an initial distance relative to each other, such as not greater than an axial distance of 3 cm. In some examples, the second image sensor may initially be disposed within a proximal region of an ETT, or even within the second imaging member housing and not yet advanced into the ETT. In these examples, the assembly is still considered to be adapted such that the assembly disposes the first video camera at an initial distance from the second video camera prior to actuation of the actuator.

In some examples, the two images sensor may be maintained at a distance relative to each other when the sensors are assembled into the assembly, and at some time during use the sensors may become axially aligned while the two sensors are disposed in an upper airway. This may occur if, after assembly, the second image sensor is initially proximal to the first image sensor at some maintained initial distance, and wherein the second image sensor is moved distally some distance relative to the first image sensor until it becomes axially aligned with the first image sensor. The two sensors in this example may be axially aligned only for a moment if the second image sensor continues to be moves distally, for example.

Exemplary Methods for Providing Enhanced Visualization and Navigation of an Intubation Tube Introducer in Airway Management Procedures (Optionally During an Intubation Procedure)

Figure 7:
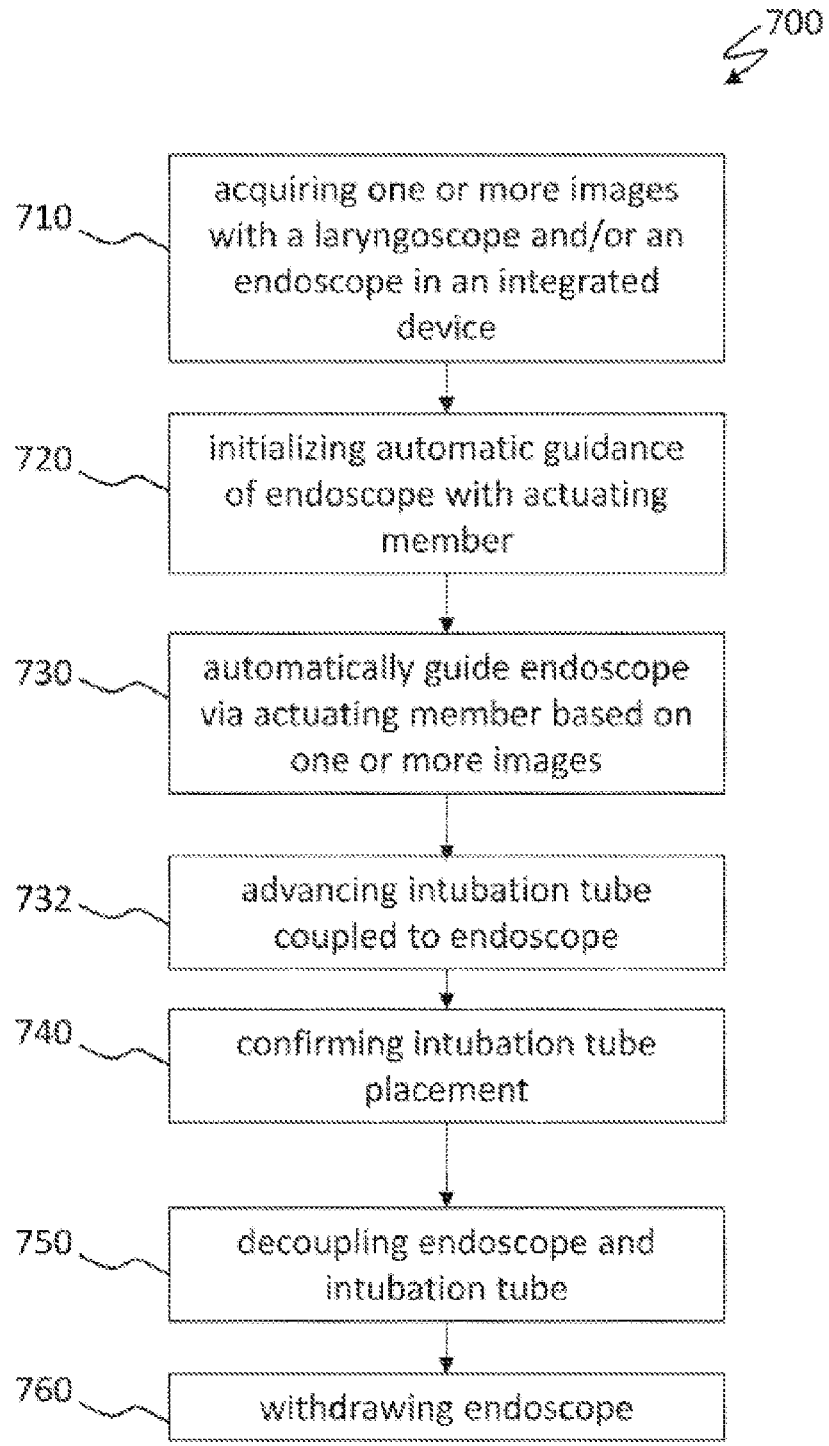
FIG. 7 is a flowchart of an example variation of a method for tracheal intubation of a patient.

The disclosure herein includes aspects related to methods of enhanced visualization, navigation and placement of intubation tube introducers. FIG. 7 illustrates as a flow chart a merely exemplary method of positioning an ETT in a trachea during an intubation procedure. As shown in exemplary FIG. 7, method 700 for assisting performance of a robotically-assisted intubation procedure may include acquiring one or more images 710 with a first imaging member (e.g., laryngoscope) or a second imaging member (e.g., an endoscope) with an integrated hand-held system or assembly, initializing automatic guidance of an introducer (e.g., endoscope) with an actuating member 720, automatically guiding the introducer (e.g., endoscope) 730 via the actuating member based on one or more images, advancing an intubation tube over the introducer (e.g., endoscope) 732, visually confirming intubation tube placement 740, such as with an introducer image sensor, decoupling the introducer and intubation tube 750, withdrawing the handheld system or assembly (including introducer 760 and first imaging member 710 portions) out of patient's mouth. In some variations, the method 700 may be performed with one or more variations of the devices described herein.

The acquiring one or more images step 710 may comprise one or more images acquired using one or more image sensors in the integrated system or assembly, such as with a laryngoscope (e.g., video laryngoscope) and/or an endoscope that are part of the integrated system or assembly. The images may be interpreted manually and subsequently automatic guidance of the introducer may be initiated with, for example, a user selection of an automated mode (e.g., activating an "AI" button such as button 280 shown in FIG. 2C) or by selection of the automated-manual assist mode as described herein. Additionally or alternatively, images may be interpreted by one or more processors applying one or more suitable computer vision and/or machine learning algorithms to the one or more images to identify a suitable anatomical target and automatically initiate actuated guidance of the endoscope. In some variations, initialization of the automatic guidance of the introducer (e.g., endoscope) (720) may be based on one or more images acquired from a laryngoscope, while in some variations such initialization may be based on one or more images acquired from both a laryngoscope and an introducer, and in some examples such initialization may be based on one or more images acquired from the introducer alone.

As shown in the exemplary FIG. 7, the method may include automatically guiding the introducer (e.g., endoscope) (730) via an actuating member in the handheld housing based on one or more images from a laryngoscope and/or an endoscope. Guiding the introducer may include, for example, automatically guiding the introducer via the actuating member in a longitudinal forward and backward motion, and/or axial left-right rotations. Furthermore, guiding the introducer may include articulating the distal end of the introducer with at least one of the several degrees of freedom, including up-down and left-right articulations. While in some variations the introducer may be guided automatically using a robotic system utilizing suitable AI image processing techniques, additionally or alternatively the introducer may be robotically guided manually (e.g. automated-manual assist mode) using a suitable user interface device (e.g., joystick), wherein the actuating mechanism disposed in the handle can robotically control the movement of the introducer in response to the operator's manual interaction with the system (e.g., a joystick).

Various AI or machine learning methods may be performed to automatically guide the introducer. For example, suitable image recognition or processing algorithms may identify anatomical landmarks in images from the device such as that described herein. AI-assisted intubation targeting of the vocal cords may utilize specialized targeting software, which analyzes multiple image streams, marks and displays the target (e.g. target crosshairs), analyzes an expected intubation tube navigation trajectory, identifies the distinct characteristics of the tracheal opening visible between the vocal cords, and/or displays this information in real time on display screen.

Different targeting methods have been described in the literature. One or more modules that perform particular functions, including but not limited to real time computerized image processing, recognition and mapping, visual guidance, guidance information, and interfacing with robotic intubation interface, can be used to achieve fully automated or automated-manual assist robotic intubation. The special purpose logic circuitry, such as FPGA (field programmable gate array) and/or an ASIC (application-specific integrated circuit) and/or other applications can be used in the methods and devices such as those described herein.

One or more various computer vision and machine learning algorithms may be used in this invention, including SLAM (simultaneous localization and mapping), Spatial Transformer Module (STM)-inspired techniques, deep neural networks (DNN) and convoluted neural networks (CNN) learning, and others.

If performed during an intubation procedure, the method 700 may further include advancing an intubation tube that is coupled to (disposed about) the introducer (e.g., endoscope) (732). The intubation tube may, for example, be telescopically engaged with (e.g., surround) the introducer. While the introducer is manually or automatically guided, the intubation tube may be advanced over the introducer toward a target position. In some variations, the intubation tube may be advanced manually. In some variations, the intubation tube may be advanced automatically using one more suitable actuating systems, such as those described herein. Furthermore, in some variations, the intubation tube may be advanced manually during certain parts of its travel, and advanced automatically during other parts of its travel (e.g., as desired by a user).

Furthermore, in some variations the method may include manually advancing the intubation tube while maintaining automated guidance of the introducer. For example, a user may be holding the integrated system with one hand, and manually manipulate the intubation tube over the introducer with the other hand (e.g., push the intubation tube forward on the introducer and/or rotate the intubation tube (and/or introducer together as a unit) toward a location in a targeted image, such as an image from an introducer image sensor that is disposed in a trachea. Accordingly, in some variations, the manual advancement of the intubation tube may, for example, help reduce the travel distance of the intubation tube toward a target position and further improve the speed of intubation.

Throughout an intubation procedure, as the introducer and intubation tube are automatically and/or manually advanced into a target position, images from the first imaging member and/or the second imaging member may be displayed, optionally continuously for some epoch or period of time, in real-time or near real-time to the user. The images, such an image from an introducer image sensor while in the trachea, may be used to immediately confirm proper intubation tube placement (740), an optionally optimal intubation tube positioning, and/or allow immediate identification of intubation tube misplacement, and/or allow a user to troubleshoot the intubation procedure both from above and below the vocal cords, including problems with intubation tube advancement, which may prompt suitable intervention(s). For example, the first imaging sensor is proximally spaced from the introducer image sensor and may provide a view and identification of a larger anatomical region, which can provide an additional view of the tracheal tube movement that provides more information about placement than simply using the introducer image sensor alone. Once the intubation tube is visually confirmed to be properly placed in the trachea, which is generally confirmed with the introducer imaging sensor that is also placed within the trachea and below the cords, the introducer may then be removed from within the intubation tube (750) automatically through robotic actuation and/or manually, and the introducer may be withdrawn (760) while leaving the intubation tube in place.

Example. A merely exemplary, non-limiting, method of performing TI using an integrate dual-video system or assembly such as those described herein is described below. It is understood that not all steps need be performed, and the order may be modified if suitable.

1. A disposable dual-channel cover (e.g., 260) is coupled to a handheld housing (e.g., housing 210), and a laryngoscopy baton (e.g., 220) is placed inside a laryngoscopy channel of the cover. The system is powered on. 2. A disposable introducer (e.g., endoscope) is coupled to the handheld housing directly or indirectly, such as to an actuating member of the system. The introducer is automatically checked by the device for full functionality upon connection with the handheld housing and such as to the actuating member. 3. The introducer is optionally lubricated and placed inside a selected ETT. The ETT is placed inside the intubation tube channel (which need not be an internal lumen) of the cover. 4. The user performs manual video laryngoscopy using the video laryngoscope (the display screen is in default single picture mode showing the laryngoscope image feed), and identifies anatomic structure(s) on the display of the system. Image recognition and/or AI interface is activated and initiates automated robotic actuation of the actuating member and introducer through the actuating interface. The motions of the actuating member are fully transmitted to the introducer. (The actuation may also be activated manually by selecting an AI operational mode button on the housing of the device or by using the automated-manual assist mode). 5. Upon actuation, a split or picture-in-picture video screen feature is displayed, allowing the user to observe TI in its entirety, optionally continuously and in real time. This display mode may be activated automatically or manually. 6. In a fully automated mode, the device automatically maneuvers the introducer into the patient's trachea using AI or robotic-assisted navigation, including forward-back movement, axial rotation, and/or steering tip articulation. In some examples this is performed using video data from the first image sensor alone, and in some examples this may be performed using video data from the first and second image sensors. For example, initial movement of the introducer may be based automatically based primarily or solely based on video data from the first imaging sensor (which may be a video laryngoscope image sensor) 7. In an automated-manual assist mode and in manual assist mode, manual operation of the device with a user interface device may instantly override a fully automated mode, for example. In a manual mode, the forward-back and/or axial rotation of the actuating member can be controlled manually, and the articulation of the distal end of the endoscope may be automated. Fully automated mode can be allowed to resume after the user presses the AI operational mode button, for example. In an automated-manual assist mode, the operator manually exerts the control of the automatic actuators in the system. 8. During navigation of the introducer, upon recognition of an airway anatomy, a visual indicator (e.g., a square or a circle) may optionally appear on the screen around the displayed airway. The introducer articulation can move the tip in the direction of the geometrical center point of the detected glottis opening and through the vocal cords. 9. Introducer actuation around the anatomic structures during the TI sequence may be continuously visualized by the user via the, for example, video laryngoscopy image feed or signal that is displayed on the display. Visually presenting video data from the first image sensor (e.g., video laryngoscope image sensor) with the larger angle of view on the display provides for operator/user to better troubleshoot navigation and to enable manual intervention or assistance, if needed. For example, while viewing a video signal from the first image sensor, the user can move the entire integrated system as a unit with a single handle, which may provide for slightly adjustment in positioning of the integrated system. 10. The introducer may be automatically navigated around the patient's anatomy, through the tracheal opening, and advanced inside the patient's trachea. 11. The ETT can be manually advanced distally off the introducer (or automatically advanced) into the patient's trachea, allowing for visual confirmation of proper ETT placement using image data from the introducer image source. ETT advancement can be observed continuously, both from above (first image sensor data) and below the vocal cords (send image sensor) on the display screen, and tracheal ETT placement is visually confirmed. Additionally, visual confirmation of tracheal ETT placement can be observed more closely by obtaining a full picture of the patient tracheal anatomy, by optionally pressing a picture-in-picture button twice on the display screen (optionally accomplished with other mechanisms such as using a remote control, audio commands, or a touch screen/display). Additionally, the ETT may be optimally positioned in the trachea (not too deep, not too high) above the tracheal carina. 12. The ETT can be released from the intubation tube channel 266 of the cover. The system is removed from the patient's mouth, while leaving the ETT in place in the trachea. 13. A cuff of the ETT can be inflated, and manual or mechanical ventilation through the ETT is commenced using a ventilating bag or automatic ventilator. ETT tracheal placement may optionally be further confirmed by any suitable means (e.g., breath sounds, EtCO2). 14. One of the advantages of the integrated dual-video systems herein is that if AI/robotic-assistance TI fails for any reason, the operator has a back-up option to complete TI using the system as only a video laryngoscope, for example, with a variety of conventional TI options, as described above. 15. In embodiments in which an actuating member and an introducer are separable, if a problem occurs while advancing the ETT through the vocal cords (e.g., ETT repeatedly "catches" on the glottic structures), the introducer can be disconnected from the actuating member and used as a hand-held introducer (endoscope) to further facilitate directing the ETT through the glottic opening.

Figure 15:
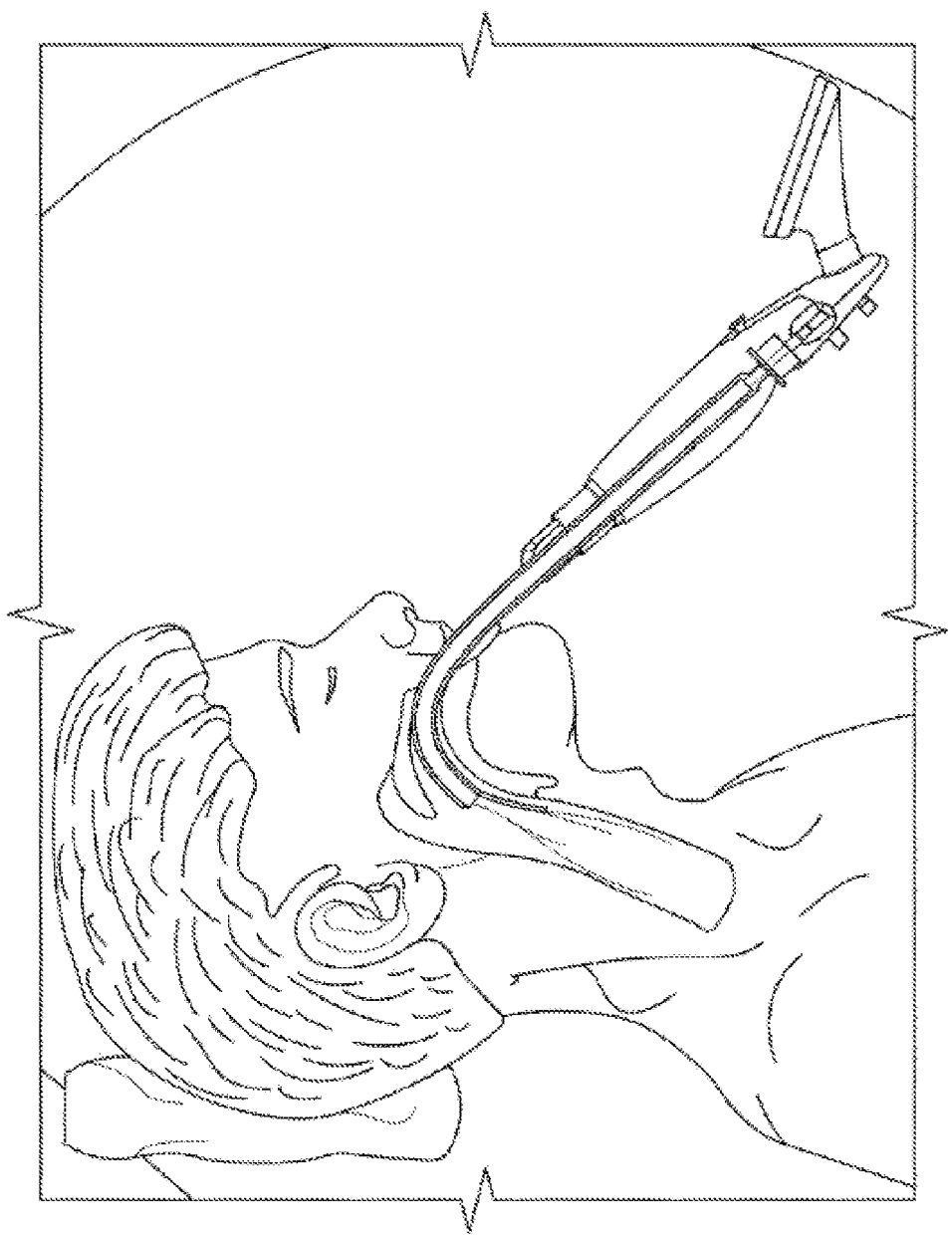
FIG. 15 illustrate an exemplary integrated and handheld dual-video tracheal intubation assembly disposed in an upper airway.

FIG. 15 illustrates generally an integrated, dual-video handheld intubation assembly (including any described herein) after it has been positioned into an upper airway of a patient.

Figure 16A:
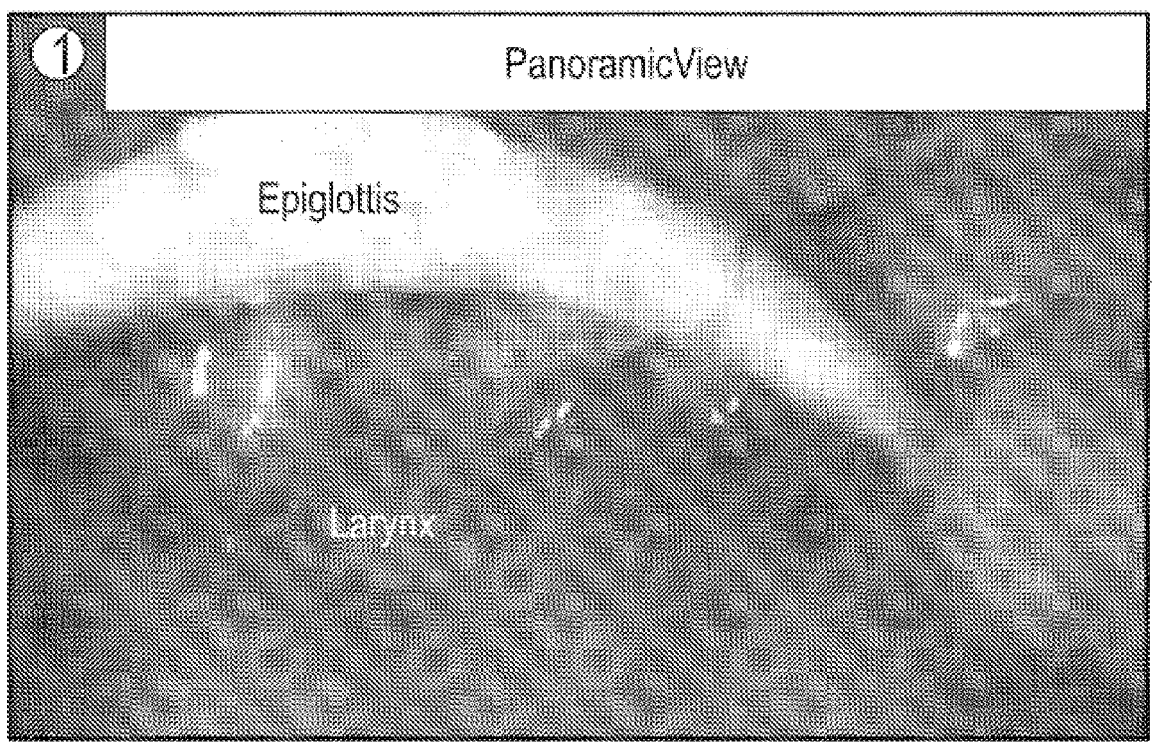
FIG. 16A illustrates an exemplary view on an exemplary display of image data from a first image sensor when maintained in an upper airway.

FIGS. 16A-16D illustrate merely exemplary images that may be captured and/or shown on a display during any of the intubation procedures described, which may include using any of the handheld systems or assemblies herein. The disclosure that follows describes FIGS. 16A-16D in the context of video data or video images displayed on a display during an intubation system and exemplary benefits of systems herein that are adapted to display the image data from first and second image sensors. FIG. 16A illustrates a view provided by a first image source disposed at a distal region of a first imaging member, such as a video camera. The epiglottis and larynx are labeled in the FIG. 16A, which may optionally, but not necessarily be, a panoramic view as indicated. As can be seen, it is difficult-to-impossible to view the vocal cords in this image. Any of the methods herein may optionally include receiving as input data that is indicative of the anatomical view shown in FIG. 16A, and causing an output that initiates an automatic robotic controlled movement of the introducer. In alternative embodiments (described in the context of exemplary modes herein), the system does not need to automatically control the movement, but rather a user may manually cause the robotic movement of the introducer via the operable communication between the disposable introducer and the housing.

Figure 16B:
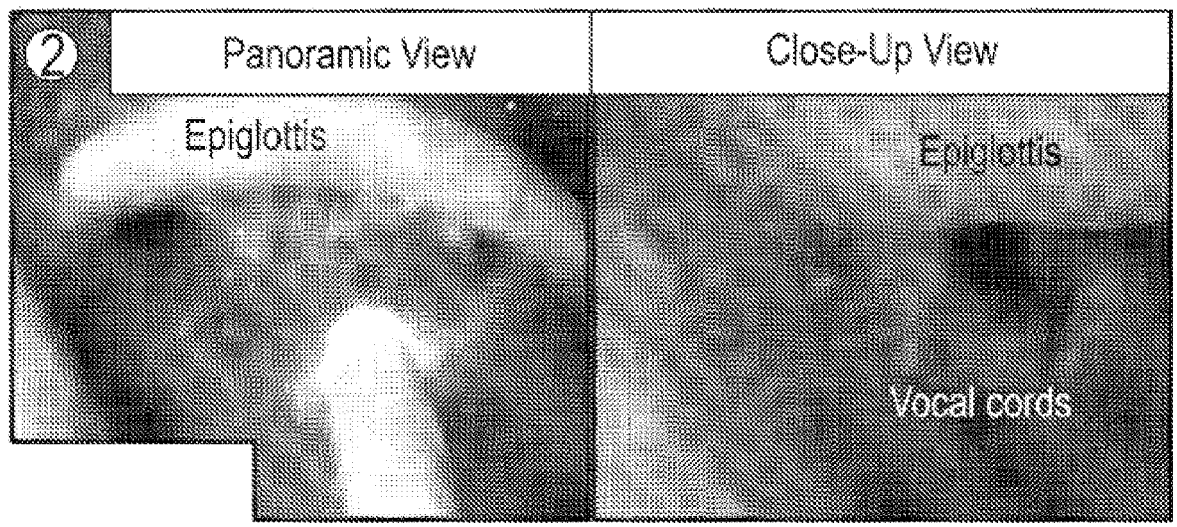
FIG. 16B illustrates an exemplary view displayed on an exemplary display of image data from first and second image sensors.

FIG. 16B illustrates image (e.g., video) data from a first image sensor on the left and image data from a second image sensor on the right. The image data from the first image sensor on the left provides visualization of the introducer as shown after the introducer has been moved distally relative to its initial position (in which the second image sensor (e.g. video camera)) is initially maintained at a distance from the first image sensor (e.g., video camera) and relative to the first image source. As can be seen, as the introducer is distally moved (optionally also rotated and/or deflected), the second image sensor at the distal end of the introducer is also advanced distally relative to the first image sensor. The image data captured by the first image sensor, as shown, provides a view of the introducer as it is being robotically advanced (automatically and/or manually) and also provides a view of a larger anatomical region than the view provided by the introducer image sensor. In the event that the second image data is compromised (e.g., due to blood or secretions in the vicinity of the second image sensor, for example), the image from the first image sensor can advantageously help determine where the introducer is, and also may help to further facilitate continued movement of the introducer (automatic or manual robotic movement). FIG. 16B illustrates the introducer after it has been robotically moved to some extent towards the glottic opening and under the epiglottis, as shown.

Figure 16C:
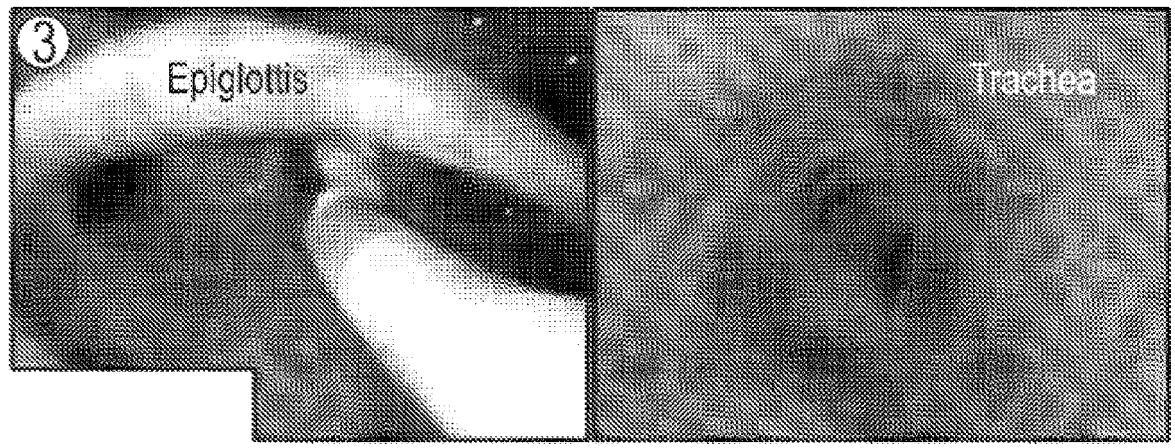
FIG. 16C illustrates an exemplary view displayed on an exemplary display of image data from first and second image sensors, while the first image sensor is maintained in an upper airway.

FIG. 16C illustrates the image data from the first and second image sensors after the introducer has been advanced through the glottic opening, wherein the second image sensor provides visualization of the trachea as shown in the view to the right in FIG. 16C. The first image sensor (image data on the left in the figure) continues to show the properly positioned introducer, which is again a benefit of the integrated nature of the dual-video intubation assemblies herein.

Figure 16D:
FIG. 16D illustrates an exemplary view displayed on an exemplary display of image data from first and second image sensors, while the first image sensor is maintained in an upper airway.

FIG. 16D again shows image data from the two image sources, and shows an endotracheal tube after it has been advanced over the introducer towards the glottic opening, through the glottic opening, and into the trachea, as shown. The window or opening shown in the upper left section of the right image of FIG. 16D is a standard side opening in the ETT (referred to as the Murphy eye). The generally linear feature extending from the top right corner is a radiopaque line of the ETT that illustrates where the main, distal, opening of the ETT is.

Figure 8B:
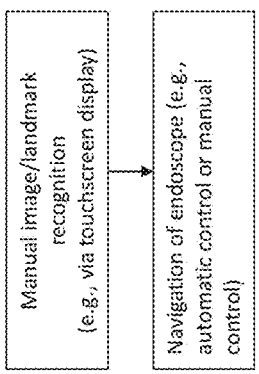
FIG. 8B illustrates an exemplary sequence showing manual image/landmark recognition.
Figure 8A:
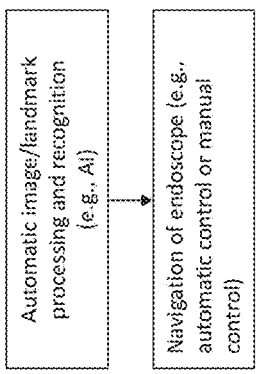
FIG. 8A illustrates an exemplary sequence illustrating automatic image/landmark recognition.

Some of the disclosure set forth above describes identifying or recognizing anatomical landmarks or locations in an image to help guide the introducer, towards vocal cords, through the vocal cords and into the trachea. For example, landmarks include but are not limited to the epiglottis, vocal cords, arytenoid cartilages, pyriform sinuses, tongue, a geometrical center point of the glottic opening, the trachea wall (tracheal rings), regions of an image that are darker than adjacent regions, etc. In some methods and devices herein, identifying or recognizing anatomical landmarks or location (which may generally be described herein as image recognition) may be performed or accomplished automatically. For example without limitation, and as is set forth above, the image or landmark recognition may be performed using AI or image recognition software configured and adapted to automatically recognize certain landmarks based on one or more images or image data received while using the system. FIG. 8A illustrates an exemplary sequence illustrating automatic image/landmark recognition, which may then facilitate the robotic control and navigation of the introducer (e.g., flexible and/or rigid endoscope), additional details of which are described herein. In some methods and devices herein, identifying or recognizing anatomical landmarks may be performed or accomplished manually by medical personnel or other operator(s). For example, a physician may provide input (e.g., touch, audio, etc.) to the system to identify or recognize one or more aspects of an image displayed on a screen or display. For example, a physician may touch a touchscreen at the location of recognized vocal cords in the displayed image, or a location to which the operator wants the introducer to be moved. FIG. 8B illustrates an exemplary sequence showing manual image/landmark recognition, which may then facilitate the robotic control and navigation of the endoscope, additional details of which are described herein. It is understood that aspects of FIGS. 8A and 8B may be combined. For example, without limitation, automatic recognition may take place (e.g., as part of a device mode), and manual confirmation of the automatically recognized aspect of the image (e.g., manually touching a confirmation icon on the display) may be required before endoscope navigation is initiated.

Any of the systems herein may include one or more processors that has stored therein an executable method (e.g., software, firmware, algorithm(s), etc.) that is adapted to receive instructions or input that is directly or indirectly based on a user interaction with a display (optionally touch and/or audio interaction and/or haptic feedback) while the display presents at least one image (still or video). The executable method(s) may facilitate robotic control of introducer movement via an actuating member in the housing and/or first imaging member or other member that is in operable communication with the introducer.

Figure 9B:
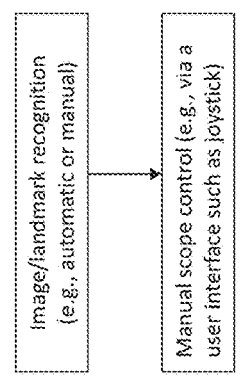
FIG. 9B illustrates an exemplary sequence of image recognition followed by manual robotic control of the introducer.
Figure 9A:
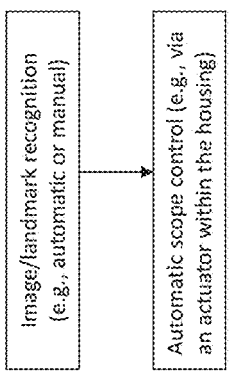
FIG. 9A illustrates an exemplary sequence of image recognition followed by automatic robotic control of the introducer.

Some of the disclosure set forth above describes robotic control of the movement of the introducer through the vocal cords and into the trachea. For example, some disclosure herein is related to automatic robotic control of an introducer. FIG. 9A illustrates an exemplary sequence of image recognition (such as either of those shown in FIGS. 8A and 8B) followed by automatic control of the introducer into the trachea (or other lumen depending on the medical procedure). For example, automatic movement of an introducer may occur with any of the actuators and/or actuation members herein following one or more image recognition and/or processing steps. In some instances, movement of the introducer may be at least partially manually controlled, such as (but not limited to) with user movement of an actuator such as a joystick, wheel, slider, or other similar actuator (which may be in operable communication with an internal housing actuator) to control one or more types of movement of the introducer. Additional details on types of optional movement control (e.g., distal-proximal, rotation, and/or distal-tip deflection) are described elsewhere herein. It is understood that the exemplary robotic control steps in FIGS. 9A and 9B may be combined with the image processing and/or image recognition from FIG. 8A and/or FIG. 8B.

Methods, devices and/or systems herein may not include automatic image processing and/or recognition. Alternatively, methods, devices and systems herein may be adapted and configured with a mode or used in a manner that does not include the use of automatic image processing and/or recognition. Both instances may generally be referred to herein as a manual mode. FIG. 8B includes exemplary steps that may be included in a manual mode (other steps, such as any of those herein may obviously be included in the overall introducer navigation process). The introducer control in FIGS. 9A and/or 9B (or as described elsewhere herein) may be included in a manual mode. In some instances, a manual mode may be initiated in response to a user action or triggering event, such as by pushing a button to initiate a manual mode, or by touching a touch screen to identify part of an image. In some instances, any of the devices herein may default to a manual mode or may not be adapted with AI or other automatic image processing and/or recognition. In some instances, the device may automatically enter manual mode, and/or sound, show, or vibrate an alert, when the video quality is poor, or when the confidence in the automatic navigation is below a certain threshold, or when abnormal or unusual anatomy is identified or in other circumstances.

As is described herein, methods, systems and devices herein may be used or include an automated mode (but it is understood that they may have other modes or be used in other ways as well). An automated mode may include automatic image processing or recognition (e.g., such as shown in FIG. 8A) and automatic robotic scope control and/or navigation (e.g., such as shown in FIG. 9A), which can optionally be performed in a continuous, closed loop manner In some instances, the device and methods operate in an automated mode in response to a user selection or initiation of the mode, such as by (for example only) pushing an AI button on the handheld (e.g., FIG. 2C). In some instances, an automated mode may be default and may function in automated mode without needed user initiation. In some instances, an automated mode may be initiated or occur after any number of modes or steps have already occurred, such as after a manual control mode (e.g., FIG. 9B) that the user wishes to discontinue and return to an automated mode. Any of the devices, systems and methods herein may be used or have a mode in which an automated mode continues while and as long as a medical professional continues to actuate an actuator such as a button or switch on the handheld. In these modes, the system can be adapted such that when the user stops actuating the actuator (e.g., releases a button or switch), the automatic scope control and/or navigation ceases. For example only, any of the "AI" buttons on the handheld may serve as this type of actuator that once released, the automated mode may cease (e.g., a dead man's switch). This mode may be used with any other mode or method herein.

Figure 10:
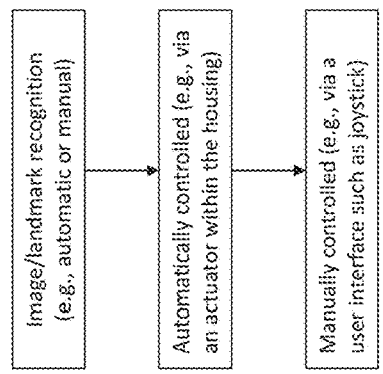
FIG. 10 illustrates exemplary steps that include manual robotic control at a time subsequent to automatic robotic control.

Any of the devices and systems herein may be adapted such that a user may override or stop an automated scope control/navigation by interacting with the handheld (including any display associated therewith). FIG. 10 (which is similar to FIG. 9B) illustrates exemplary steps that include manual robotic control at a time subsequent to automatic robotic control (other steps may of course be included). For example only, an operator may use a handheld housing actuator (e.g., a joystick, wheel, slider, etc.) to override (optionally immediately causing an automated mode to stop or be paused) an automated navigation. The user control may provide for one or more of forward-back (distal-proximal) and rotation. Some systems may be adapted such that an automated mode may be activated again after user interaction with the handheld (e.g., pressing an "AI" button). For example, in FIG. 10, after the manual control, the method may again return to automatic control, and may loop back and forth as desired by the operator or device.

Any of the systems, devices and methods herein may be adapted such that an operator may indicate a navigation pathway (or location along a pathway) on a display, such as by touching a particular location on the image that is presented on the display, or even using voice commands for which the system may be adapted to receive, process, and initiate an event. The system may be adapted to then automatically navigate to or towards that location. This is similar to FIG. 9A, wherein the landmark recognition in this example comprises indicating a location or intermediate pathway location (and not necessarily a particular anatomical landmark).

As shown in FIG. 9A, any of the devices and systems herein may be adapted to automatically control the introducer navigation (e.g., such as having a mode that is adapted to provide this functionality). With automatic image processing and/or recognition, the system may be adapted to receive image data and determine a pathway for the introducer (e.g., scope). With manual image recognition, the system may be adapted to process the manual identification and determine a pathway for the scope. The onboard AI may then communicate instructions to facilitate the control of the on-board actuator to thereby facilitate smart, atraumatic, AI-enabled, robotic-assisted navigation of the scope into the patient's airway. The sequence may repeat in a closed loop manner. As is set forth above, once the scope is placed inside the patient's trachea, the operator can manually advance the tracheal tube over the scope using the scope as an atraumatic intubation guide, similar to a guidewire in other medical procedures. Tracheal tube advancement may be continuously visualized by the operator on a display screen (such as the handheld or stationary monitor), optionally both from above and below the vocal cords, with either a single image (optionally able to toggle between more than one) or at least two images being displayed at the same time.

When the term laryngoscope is used herein, it is understood that the term may refer to a traditional laryngoscope, but the term may also refer to any type of device that is adapted to provide at least video imagery to an operator, and preferably (but not required) panoramic video. In general, these are referred to herein as first imaging members (or first elongate imaging members). First imaging members may be manufactured and packaged coupled to the handheld housing, or they may be releasably coupled to the housing just prior to the procedure by an operator or assistant. A laryngoscope herein may generally be referred to as any of a video guide ("VG"), and optional a panoramic video guide ("PVG"), and a first imaging member, and may include an image sensor (e.g., video camera) at its distal end, and optical and electrical wiring and communication functionality. The first imaging member may be functionally similar to the video baton of existing video laryngoscopes and may include any features or functionality thereof.

It is also understood that any of the video monitors (e.g., displays) herein may be integrated into any of the handheld housings herein, or they may also be a separate, free-standing video monitor (including being part of a detachable component that can be releasably secured to the handheld). As is set forth herein, any of the video monitors may include a touch screen, which may be adapted to respond to taps, swipes, and any other type of manual commands. Any of the video monitors herein may also be adapted to be responsive to audio input (e.g., voice commands) or haptic commands. The terms display, screen, and monitor may be used interchangeably herein.

In any of the systems herein, the introducer may be an endoscope (rigid and/or flexible), which may also simply be referred to herein as a scope. The terminology is understood to not necessarily be limiting in functionality. In some instances, the introducer is adapted to be robotically controlled (automatically and/or manually), and may include a flexible (optionally at least partially flexible) elongate tubular member or shaft and one or more of an optional distal camera, electrical wiring, optional optical transmission element(s), or one or more elongate elements (e.g., pull wires) used in articulating the distal tip. As is set forth herein, the introducer may be adapted to be releasably secured to any of the housings (indirectly or directly), optionally via a coupler wherein the coupling creates operable robotic communication between the introducer and the handheld housing to facilitate robotic control of the introducer, which is described in more detail elsewhere herein.

Any of the covers herein (which may also be referred to herein as blades) may include a first elongate channel adapted to receive a first imaging member therein, and the covers may also be adapted to be releasably secured to a tracheal tube to restrict movement of the tracheal tube relative to the cover in at least one direction. The covers may include a separate tracheal tube lumen, or they may be configured with a tracheal tube stabilizer to which a tracheal tube may be releasably secured, such as one or more clips or a partial channel. The covers are generally configured such that the position of the tracheal tube, when it is initially releasably secured to the cover, is generally maintained relative to the first imaging member channel and lumen, additional details of which are set forth above.

As is set forth herein, the housings may be packaged with an introducer (e.g., an endoscope) or other elongate tracheal tube guiding device already attached or coupled to the housing. In alternative examples, an introducer is not packaged securely coupled to the housing, and is releasably secured or coupled to the housing prior to the medical procedure by an operator or assistant. In either scenario, an introducer is in operable communication with the housing to facilitate robotic control of the introducer and optionally transmit optical data from the introducer to the housing, which may be displayed on a display as set forth herein. The introducer may optionally be releasably secured to a coupler on the housing, wherein the coupler may be any suitable component or components (including a separate component such as an adaptor that couples to both the handheld and the introducer) sized and configured to interact or interface with the guiding introducer and become releasably secured thereto. Releasably secured in this context refers to being able to secure the introducer to the housing so the two are not easily separated during normal use of device during an intubation procedure, and may include a locking mechanism that may be additionally actuated to lock the introducer to the handheld. For example, a locking mechanism may include an additional step or movement of the introducer to lock the introducer in place relative to the handheld housing. FIG. 2A illustrates an example of an introducer 250 that is releasably secured to a coupler of the housing, which may be considered to include an end of actuating member 240. In the example of FIG. 2A, actuating member 240 (and other similar internal movable actuating members) may be considered to be a robotic extension of the introducer after the introducer is releasably secured to the coupler of the housing. That is, the actuating member and introducer may be moved together and may be considered part of the same movable unit and data can be communicated from the introducer to the housing. FIG. 2C illustrates an additional example of housing that includes an internal movable robotic extension or actuating member.

As shown in the example of FIG. 2C, the internal movable robotic extension or actuating member is at least partially disposed or arranged along and/or within a guide 217 within the housing. As described above, the guide is sized and shaped to allow the actuating member to move relative to the guide yet guide the movement of the actuating member within the housing.

Figure 11:
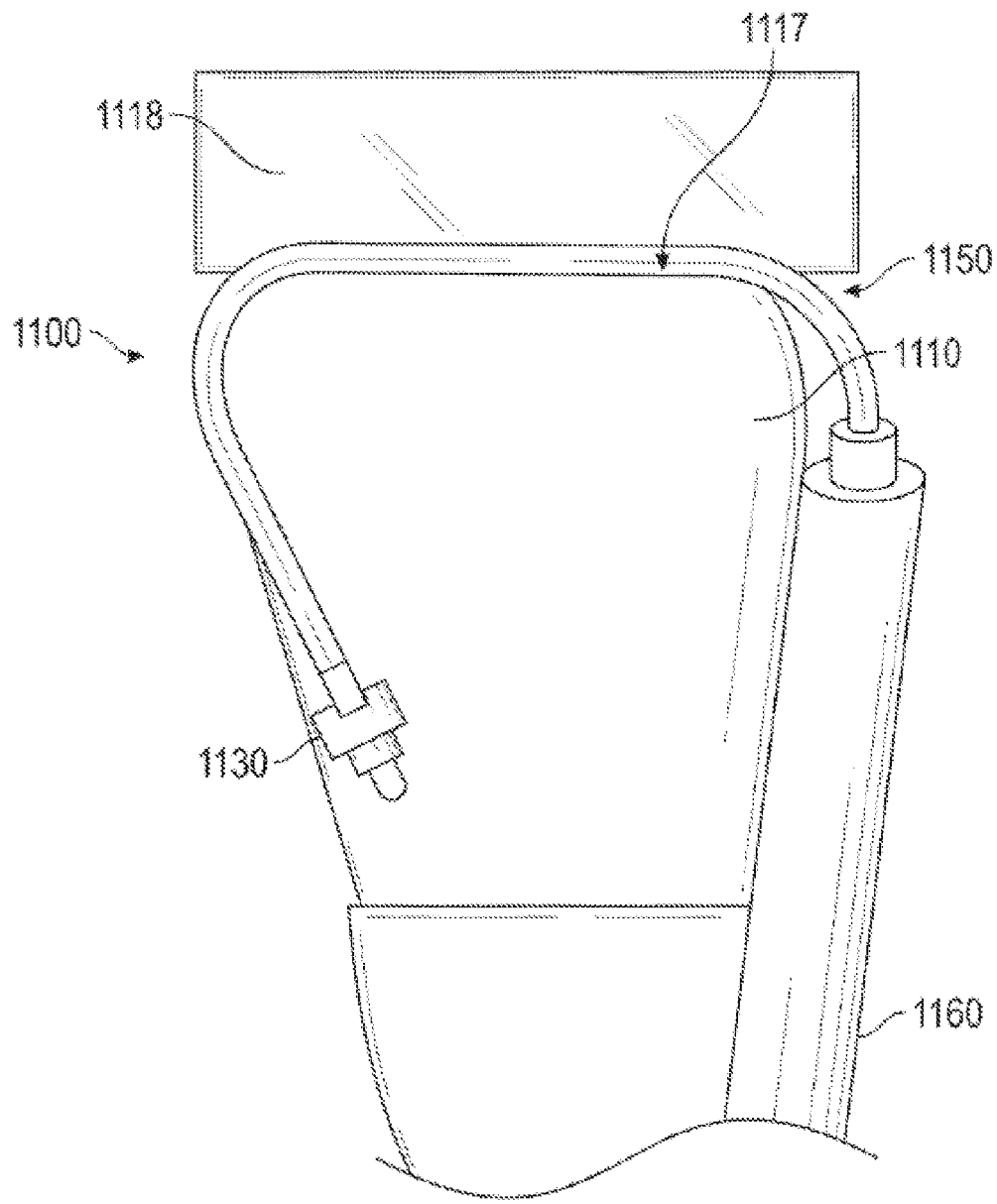
FIG. 11 illustrates a portion of an exemplary integrated and handheld intubation assembly.

FIG. 11 illustrates an additional example of a robotic handheld device or assembly adapted to facilitate delivery of a tracheal tube to a trachea (or other device to a different lumen depending on the procedure). Any other feature that can be suitably incorporated into or suitably modify the example in FIG. 11 may be included even if the text is silent on its inclusion. The device or assembly 1100 includes, among other components, a handheld housing 1110, cover or blade 1160 coupled thereto, and display 1118. In this example, handheld housing 1110 includes a universal docking station 1130, which may be disposed within the housing. An introducer delivered into a patient's trachea (or other lumen) may need to be within an outer diameter limit depending on the anatomy and/or use. For example, with pediatric patients the scope may need to be smaller than a introducer that can be used with adult patients. Depending on the use of the devices herein, it may be desirable to be able to releasably secure a plurality of introducers, flexible or rigid, to a common (e.g., universal) handheld housing, wherein these scopes may have different outer diameters ("OD") and sizes and/or possible different relative locations of the optical transmission lines within the introducer. One consideration is ensuring that the introducer, regardless of its OD and size, can be releasably secured to the handheld housing and will be in operation communication with the housing (e.g., robotically movable and optionally facilitating transmission of optical (e.g., image) data). It may thus be beneficial for the handheld device to include a universal docking station or other universal coupler (such as station 1130 in FIG. 11), which is adapted to be able to releasably secure a variety of flexible and rigid introducers with different OD and of different sizes to the handheld housing and ensure operable communication therewith. A universal docking station or universal coupler may be adapted such that it may be able to receive differently-sized introducers (e.g., having different circular outer cross-sectional dimensions, different introducer lengths, different locations of optional optical transmission elements, etc.). In some examples, the universal docking station may include a plurality of adaptors that are each sized and configured to interface correctly with the flexible/rigid introducer, regardless of its OD and size.

In the example in FIG. 11, robotically controllable introducer 1150 is shown having been already coupled to housing 1110 and to docking station 1130, which may be within the housing. Once coupled, the introducer 1150 can be moved in any of the manners described herein with actuators within the housing (e.g., distal-proximal, rotational, tip deflection in at least four different directions).

FIG. 11 also shows an exemplary scope or introducer guide 1117 that is associated with an outer or close to outer region of the housing (and may extend from an outer housing surface), compared to internal guide 217 in FIG. 2C, for example. FIG. 11 illustrates an introducer 1150 that is stably received within guide 1117, which in this example is disposed at the top region of the housing. This location may allow the introducer to be secured and movable relative to the top of the housing, yet still have the central introducer region extend through the tracheal tube ETT. Guide 1117 may have a tubular configuration through which the introducer is passed before being coupled to the coupler and universal docking station 11130. Alternative guide configurations may be used as well. For example, guide 1117 may not form a complete lumen, such as if the guide has a general "C" cross-sectional shape, as long as the introducer is movable relative to the guide and the guide prevents the introducer from being disassociated from the guide.

As is set forth above, in some embodiments when the introducer is directly or indirectly releasably coupled to the handheld housing (e.g., intubation procedures), the introducer may be robotically moved, including distal advancement toward a trachea. In some embodiments the assembly is optionally adapted to be able to robotically advance the introducer at least 10-12 cm (either with automatic and/or manual robotic navigation) past the tip of the ETT so that it may be advanced into secure position in the trachea and sufficiently deep into the patient's trachea.

In some embodiments the handheld assembly is configured to be able to robotically move the introducer from 5 cm to 40 cm, or 5 cm to 60 cm, distally once the introducer is operatively coupled (directly or indirectly) to the housing. For example only, the handheld housing may be adapted to move a robotic extension (and thus move the introducer) distally from 5 cm to 40 cm, and optionally not more than 40 cm. Alternatively, with reference to FIG. 11, the assembly may optionally be able to move the introducer from 5 cm to 40 cm distally, or 5 cm to 60 cm distally (if the assembly does not include an actuating member or robotic extension, for example). In this disclosure, the phrases actuating member, robotic extension, and introducer (or endoscope) extension may be used interchangeably.

The total length of the introducer may depend on the procedure. For example, in bronchoscopy procedures, the introducer may optionally have a length that is 50 cm-60 cm. Additionally, not all procedures that utilize the handheld systems and assemblies herein require the use of a cover and/or first imaging member (e.g., bronchoscopy), and when used in these procedures a first imaging member and cover may optionally be removed/detached from the handheld to remove unnecessary components and simplify the procedure.

Any of the devices herein may include an introducer distal movement limiter that is adapted to prevent the introducer (or robotic extension) from being moved distally beyond a certain distance relative to a starting axial position. This may occur due to the construction of the assembly, and certain feedback mechanisms to handheld from AI and software, which may inherently create a distal movement limiter when an introducer simply cannot be moved any further distally due to actuator and/or robotic extension construction relative to the handheld housing or assembly. The limiter may thus be considered a passive or an active movement limiter.

Figure 12:
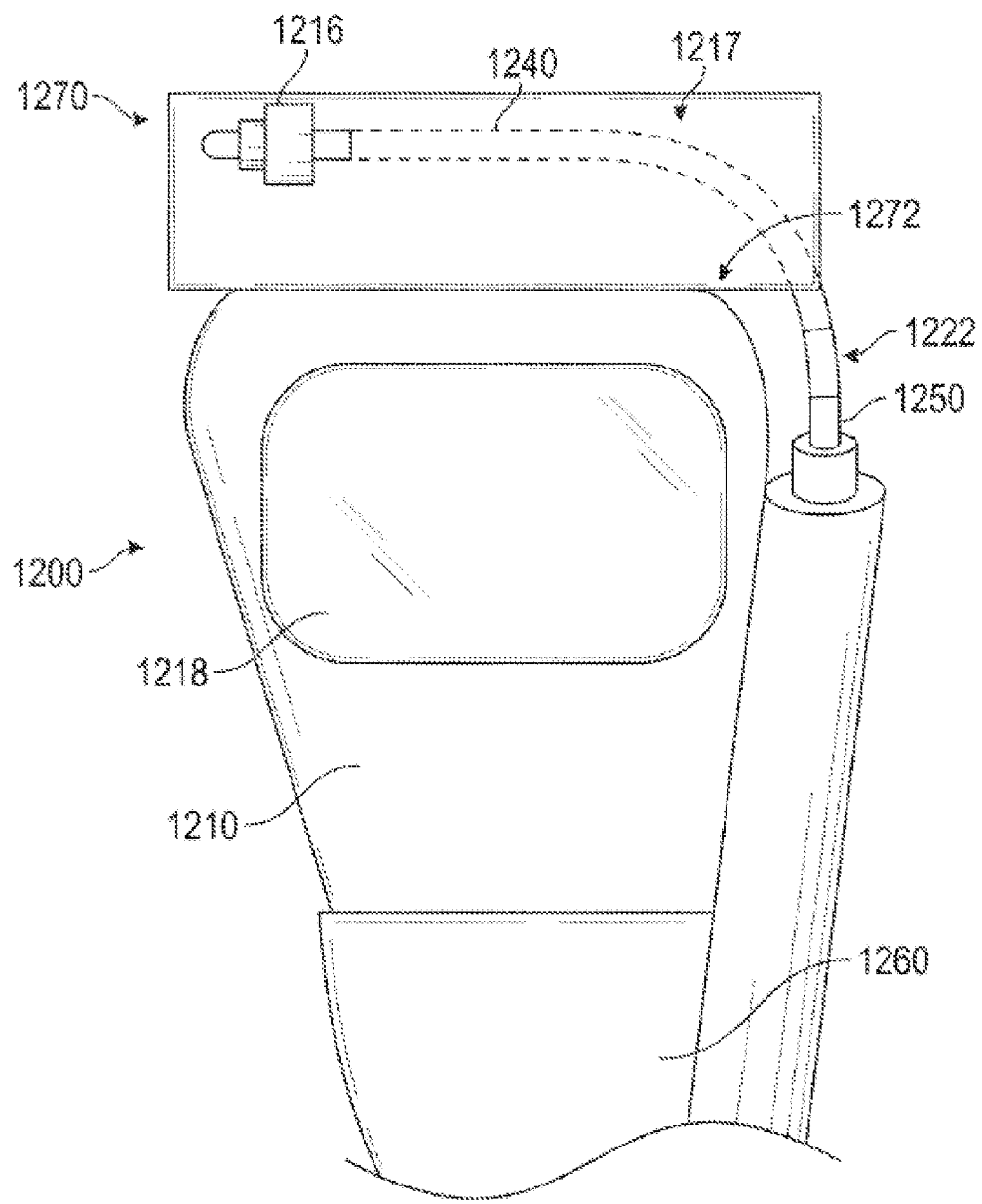
FIG. 12 illustrates a portion of an exemplary integrated and handheld intubation assembly.
Figure 13:
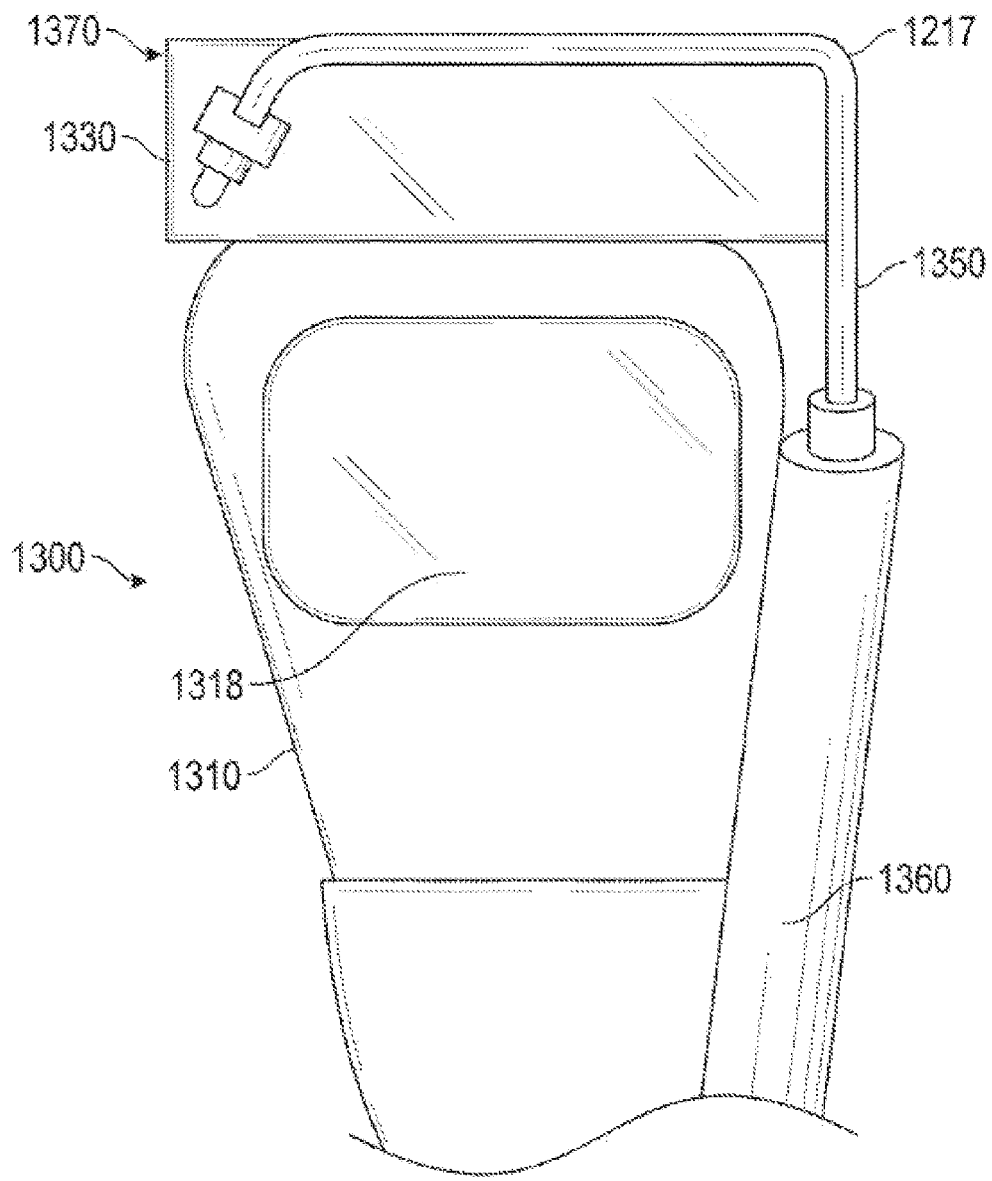
FIG. 13 illustrates a portion of an exemplary integrated and handheld intubation assembly.

In some robotic handheld devices and assemblies herein, at least some of the robotic functionality of the device may be incorporated into a component that is removable from the handheld housing, but which may be releasable secured thereto prior to the procedure. This may allow for some components to be reused more easily while others may be discarded after a procedure, for example. This may also allow some removable components to be able to be used with a variety of handheld devices, for example. This may also help and/or ease manufacturing of certain components. FIGS. 12 and 13 illustrate exemplary assemblies with a removable component that includes at least some robotic control functionality. FIG. 12 illustrates handheld housing 1200 and removable robotic block 1270 (also referred to herein as a removable introducer controller), which is shown releasably secured to the handheld housing 1200. Block as used in this context is not limiting to any particular structure or function, but refers generally to the removable functionality of the component. In this example, removable block 1270 includes introducer coupler 1222, robotic extension or actuating member 1240 at least partially within the housing of the block 1270, guide 1217 within block 1270 that may include any feature of any of the guides herein that allows for movement of the robotic extension 1240 but maintains the extension 1240 in the guide or associated with guide 1217. Actuator 1216 is also shown, which may include any of the functionality or features of any of the actuators herein (e.g., motor control to move extension 1240 and thereby move introducer 1250).

In this example, handheld housing 1210 may include a block coupler 1272, (which may also be referred to herein as an introducer controller coupler) that is sized and configured to be releasably secured to the removable block. The block 1270 may similarly include any type of suitable corresponding mating structure that is sized and configured to releasably but securely interface with the block coupler 1272 on the housing 1210. The block coupler 1272 may include a wide variety of coupling features that allow for the block to be releasably secured to housing 1210 (e.g., press fit, male/female, etc.). Once block 1270 is secured to housing 1210, and introducer 1250 is releasably secured to introducer coupler 1222, the device may be used in any other manner described herein (e.g., image processing/recognition, scope movement, light transmission, video capture, mechanical actuation, distal tip articulation, etc.). Any of the removable "blocks" herein may also be referred to herein as an introducer controller, introducer controller, or second imaging members that include an introducer.

FIG. 12 also shows removable cover 1260 (which may include any cover or blade features or functions described herein) with first and second channels that is releasably secured to housing 1210.

Handheld housing 1210 in this embodiment may include an integrated or built-in display (e.g., touchscreen) 1218, which may include any feature or functionality of any display herein, and may be used according to any method or step described herein (e g, manual anatomical landmark recognition). Alternatively, the system may have a display (integrated or removeable) situated on a side of housing 1210 rather than on its top surface as is shown in FIG. 12.

An aspect of the disclosure herein includes optionally utilizing pre-operative information about a patient during the intubation procedure, such as pre-operative imagery (e.g. CT, X-ray, MRI, PET scan and/or 3D-reconstructed images of the airway) or video that may help or be of assistance when navigating during the intubation procedure. For example only, it may be beneficial to utilize pre-operative endoscopic video exam for improved or enhanced navigation. Optionally, a patient characteristic or condition can be incorporated into the navigation procedure. For example, if the patient's disease and/or characteristic and/or condition (all of which may be generally referred to herein as a "condition") can be generally described, the operator may be able to select an appropriate condition from the plurality of selectable conditions that match that one(s) of the patient before the procedure (e.g. from software image library), and which the device (e.g., via AI and/or associated trained machine learning algorithms) will then take into account during the intubation procedure to further improve the visualization, navigation and ETT placement, further improving the speed, success rate, accuracy and safety of intubation. For example only, such an interface may include a pull-down application menu presented on any of the displays or screens herein, including a mobile phone or computer (or voice command to free up the use of a hand) that will allow a selection of a condition personalized to this particular patient's medical care. For example, conditions or information about the procedure may include "laryngeal cancer," "base of the tongue tumor", or "a nasal intubation", or "airway exchange through the intubating LMA." Combinations of procedures and conditions may also be presented or otherwise selectable such as "a nasal intubation for a patient with base of the tongue tumor." Image libraries may be retrieved for any of these conditions and/or procedures from the cloud or built-in device software, and optionally stored on the handheld and utilized as part of the navigation.

In some embodiments, existing patient images may be delivered and stored on the handheld device (e.g., wirelessly) and utilized during navigation (e.g., by AI). By way of example, these images may include one or more of preoperative videos, pictures of the patient's anatomy, or reconstructed images/videos from a CT/X-ray/MRI/PET scans and/or other imaging studies.

Any of the handheld devices or assemblies herein may further include a video recording button (or other type of actuator) on the device to allow for recording of video from one or both of a VG or scope.

Any information from any of the procedures (e.g., video and/or image data) may also be transmitted to a central location (e.g., to the cloud), either automatically or manually. The data may be used to train AI to enhance the navigation capabilities of the system and other systems.

Any information from any of the procedures (e.g., video and/or image data) may also be transmitted either automatically (e.g. wirelessly) or manually to patient's electronic medical record (EMR) to document the intubation procedure for enhanced record keeping, for billing and/or for teaching purposes.

In any of the examples herein, the tracheal tube (e.g., ETT) may also be utilized as an additional manipulating tool for the flexible introducer. Moving the tracheal tube may be beneficial to help navigate the scope and/or orient the scope that is coupled to ETT. Rotating the tracheal tube and/or moving it forward (distally) may be helpful to enhance proper introducer alignment, actuation and advancement, either when the introducer is automatically robotically navigated (e.g., FIG. 9A) or manually robotically navigated (e.g., FIG. 9B). For example, a tracheal tube may be moved forward and backward (distally-proximally) and/or axially rotated, optimizing visualization and/or navigation/movement of the introducer towards the target, improving the speed and first-pass success rate of intubation. In some uses, a tracheal tube may be moved (e.g., distally advanced and/or axially rotated) before initiating an automatic introducer navigation sequence. In some uses, a tracheal tube may be moved (e.g., distally advanced and/or axially rotated) during an automatic scope navigation sequence. In some examples, the assembly is adapted such that if the tracheal tube is manipulated during an automatic navigation sequence (e.g., FIG. 9A), the tracheal tube manipulation may automatically cause the robotic interface to stop.

One aspect of the disclosure herein is related to integrated dual-video systems that include an introducer guide or guide feature(s). As is set forth herein, the devices (either in a handheld or a removable block portion) may include an introducer guide that allows for introducer (or robotic extension) movement relative to the guide yet restricts the movement to a particular or known pathway (e.g., within the guide and preventing it from leaving the guide). As is partially described above, any of the guides herein may include a guiding rail for the proximal part of the introducer (or robotic introducer extension) within or outside of the device housing. Additionally, the guides may be sized and configured to prevent buckling of the proximal part of the introducer (including a robotic extension). Additionally, a proximal region of an introducer or a robotic extension may have a stiffness adapted to prevent scope buckling, wherein the stiffness may be greater than a stiffness of a scope shaft that is disposed outside of the housing. Additionally, any of the guides may direct the introducer at a favorable angle and/or favorable trajectory and/or pathway within or outside of the device housing. Additionally, as described above, introducer guidance can be enhanced by positioning a distal region of the introducer inside the tracheal tube to keep the scope taught due to the frictional engagement between the introducer and the tracheal tube.

One aspect of the disclosure is related to an introducer that is robotically movable distally, and optionally at least a certain distance once coupled to the handheld housing (either to a handheld or coupling via a removable block). In some merely exemplary uses, a total introducer length (with or without a robotic extension) may be about from 25 cm to 70 cm. In some exemplary uses, the device is configured to allow for at least 5 cm of robotic distal introducer advancement, and optionally from 10 cm to 40, such as 10 cm to 25 cm. This may be facilitated by the travel allowed in the handheld by a robotic extension, if the system includes a robotic extension.

In any of the embodiments herein, any of the introducer guides in the handheld housings may include a coating or other lubricious material (e.g., silicon) that facilitates scope movement relative to the guide and helps prevent buckling or binding.

In any of the embodiments herein, the introducer may include one or more sensors at a distal tip for avoiding excessive manipulation force during navigation (e.g., during tip deflection).

In any of the embodiments herein, deflection or steering of the distal scope tip may be facilitated without the use of pull wires or other elongate tensioning structures. For example—piezo, alloys (bimetal, nitinol).

In any of the embodiments herein, the introducer may have a stiffness that varies along its length. For example without limitation, the s introducers herein may comprises one or more polymeric materials (e.g., PEBAX) with varying stiffness (e.g., different durometers) along its length, and optionally providing for a distal tip that is more flexible or deflectable than proximal region of the scope. Concepts for varying polymeric elongate shaft stiffness are generally known, and any concepts related thereto may be incorporated into the embodiments herein. For example, a robotic extension may include a polymeric material with a higher durometer than an introducer material at a distal end of the introducer. Again, for example only, a proximal region of an introducer (such as a region of an introducer that interfaces with a guide on the outside of the handheld, such as shown in FIG. 11) may have a higher durometer than a distal region of the introducer to help prevent buckling during distal movement.

One aspect of the disclosure herein is that the described devices and systems may optionally yet advantageously be adapted and configured to be highly usable, handheld, portable, multi-functional dual-video airway management platforms that can be operated by a single hand of a single user. For example only, handheld housings herein may be adapted to be used in a variety of different airway management procedures and/or used with a variety of different introducers and/or a variety of different first image members (e.g., video laryngoscopes). In these embodiments, the handheld housings may be considered to be universal, or common, handheld housings to which a variety of different introducers and/or first imaging members may be interchangeably coupled and utilized. For example, it may be desirable to have a universal platform that can be coupled to introducers that are sized for pediatric patients as well as to introducers that sized for adult patients. Additionally or alternatively, it may be desirable to have a universal platform (e.g., handheld housings herein) that can be used with introducers having different lengths, such as those that are relatively longer and which may be used in a bronchoscopy and other airway management procedures described herein, as well as relatively shorter introducers that can be used in an intubation or intubation-related airway management procedure. The platform technology can also be adapted to be able to robotically control different introducers that may be coupled to the platform, regardless of the airway management procedure, medical, diagnostic or surgical. The handheld housings herein may be adapted such that one or more of an introducer, a cover or blade, or a first imaging member (e.g., video laryngoscope) may be releasably coupled to the handheld housing (directly or indirectly) to provide the multifunctionality. This disclosure thus includes devices and systems that may be adapted to provide multi-functionality and versatility not yet observed or provided in existing medical airway management approaches.

Additionally, the devices and systems herein may be adapted such that an introducer may be temporarily or permanently removed (or simply not coupled to the housing) if it is not needed for a particular airway management procedure or part of a procedure. For example, if the introducer is not needed for a procedure or part of a procedure, the introducer may not be used, and may optionally be temporarily or permanently uncoupled from the housing if it has been previously coupled to the housing. Additionally, if the first imaging member is not needed for a procedure or part of a procedure, the first imaging member may not be used, and may optionally be temporarily or permanently uncoupled from the housing if it has been previously coupled to the housing. Additionally, a blade may be temporarily or permanently removed or not used if it is not needed for a particular procedure or part of a procedure (e.g., a bronchoscopy).

The devices, assemblies, systems and methods herein thus can be adapted and configured to be multi-functional, universal, highly-usable, handheld, portable platforms that are adapted to be operated by a single user, to provide a great deal of functionality that is not observed and available with existing approaches, including being able to treat a variety of patient populations in a variety of clinical settings and locations, as well as being able to be used in a variety of airway management procedures, and optionally while robotically controlling (e.g., with AI, smart navigation, etc.) the movement of the introducer. Additionally, the devices herein can be quickly modified as needed (e.g., by temporarily or permanently removing and/or reattaching an introducer or first imaging member) based on the needs of the procedure.

While the disclosure herein describes some system and devices that may be used to generate and view two images (either simultaneously on the same screen or by toggling between views), the disclosure herein also includes the use of a handheld assembly when only one image source is used. For example only, the methods and devices herein may be used without the introducer (e.g., scope) and only with the first imaging member. For example, this may occur in a situation when the introducer module is either malfunctioning or ineffective, such as if blood and secretions interfere within the airway. The assembly may be adapted such that the operator can use the device as a regular video laryngoscope (or VG), while the introducer disconnected or at least not in use. The assemblies may have a separate mode that includes the use of the video from the first imaging member only (a VG).

Another exemplary scenario in which only one video or imaging device may be used includes the use of only the introducer video, while the first imaging member is disconnected or at least not in use. In some instances, in which the first imaging member may be removed from the housing, this may include disconnecting the first imaging member from the housing, or at least deactivating the first imaging member. One exemplary scenario of an airway management in which the introducer could be used without a first imaging member is in a nasal flexible endoscope intubation, including the option to couple the first imaging member at a later time to facilitate endoscope manipulation when it reaches the oral cavity through the nose. Another exemplary scenario of the airway management in which the scope could be used without a first imaging member is with use of the endoscope to facilitate intubation through the supraglottic airway devices ("SGAs"), which are small masks positioned inside the patient's mouth to provide ventilation/oxygenation of the lungs (when connected to the ventilator). The SGAs (e.g. the laryngeal mask airway, LMA, etc.) are frequently used to temporize a difficult airway situation when intubation is either deemed or encountered as difficult. Another exemplary scenario of the airway management in which the introducer can be used without a first imaging member is in a diagnostic upper airway endoscopy or bronchoscopy, in which the procedure may be performed through the indwelling tracheal tube or without it. Another exemplary scenario of an airway management in which the introducer can be used without a first imaging member is to confirm proper positioning of the indwelling ETT inside patient's trachea and/or optimize ETT positioning inside patient's trachea. Another exemplary scenario of an airway management in which the introducer can be used without a first imaging member is for facilitating placement and positioning of a double lumen tracheal tube—a special type of ETT used, for example, for thoracic surgery, and which placement is frequently difficult. Another exemplary scenario of an airway management in which the introducer can be used without a first imaging member is for facilitating the endoscope-assisted exchange of the existing (indwelling) ETTs in the patient, optionally in the operating room, ICU, emergency department or other location. Another exemplary scenario of an airway management in which the introducer can be used without a first imaging member is for facilitating the extubation trial. In any of these exemplary airway management procedures that may be used without the first imaging member, a cover may be detached from the handheld housing (if a blade is in fact already coupled to the handheld housing).

In some alternative uses, the devices or assemblies herein may be used in one or more ENT airway management procedures, such as the biopsies or injections (e.g. vocal cords injections). In some alternative uses, the devices herein may be used in one or more other medical and/or surgical endoscopic procedures.

Additionally, while the applications herein are related to medical procedures, it is possible the devices and methods herein may be used in non-medical procedures. For example, devices herein may be used for industrial applications where the introducers may need to be "snaked" into the orifices for evaluation of poorly accessible machinery, for example.

Any of the systems herein may be adapted such that it may optionally be used in a manner in which the first imaging member, such as a video laryngoscope (which may be referred to herein as VL or VG) is used, and the system may not be coupled to an introducer, or the introducer is not used as part of the procedure.

Any of the systems herein may be used in a manner in which the introducer is used without using a first imaging member (e.g., video laryngoscope), or a first imaging member may be detached from a handheld housing and not used in the procedure, or a first imaging member may be reattached to a handheld housing at a later time during the procedure.

Any of the systems herein may be adapted to be coupled to a plurality of covers, each of which may be at least one dimension that is different from a dimension of at least one other cover, which may allow for different sized covers for pediatrics and adults, for example.

Any of the systems herein may be adapted to be coupled to a plurality of introducers, which may have different sizes and/or lengths, which may allow the handhelds herein to be used with adults and pediatrics, for example.

Any of the systems herein may be adapted to be coupled to a plurality of deflectable introducers, which may be flexible or rigid, or partially flexible and partially rigid, and which may have different lengths and diameters.

Some exemplary systems or assemblies herein include introducers (e.g., mechanical guides, flexible endoscopes, rigid endoscopes, etc.) that may be releasably secured to a handheld housing, whereby when the introducers are secured to the housing, the handheld housing is in operable communication with the introducer such that the handheld housing is adapted to provide controlled movement of the introducer, and the introducer is adapted to receive and respond to such control. One aspect of the disclosure herein is related to optionally disposable, or one-time use, introducers that are sized and configured to be releasably secured to the handheld housing. After being releasably secured (directly or indirectly) to the handheld housing, the movement of the introducer can be controlled using the handheld housing. After a procedure is over, or at time decided by the operator, the introducer may be released from the handheld housing, and optionally may be discarded. The handheld housing may be used again, either with the same patient or after clearing and/or sterilization.

After the intubation system has been exposed to a patient, it generally must be cleaned and sterilized to be used again on a different patient. With some systems herein, it may be challenging to clean and/or sterilize one or more components that facilitate the axial movement of the introducer. As such, in some uses it may be desirable to have a disposable or one-time use introducer that can be removed after use, so that the handheld housing can be cleaned and sterilized and used with a new introducer in subsequent uses. It may thus be desirable to utilize introducers that are disposable yet affordable. Any of the introducers herein (e.g., flexible or rigid endoscopes, etc.) may be disposable and/or may be incorporated into a disposable introducer housing assembly, any of which may be sized and configured to be releasably secured to a handheld housing. The introducer housing assemblies herein may be referred to as second imaging members generally.

FIGS. 14A-14D illustrate an example of an intubation system that includes an exemplary handheld housing and an exemplary introducer housing assembly (also referred to as a second imaging member), wherein the handheld housing and the introducer housing assembly are sized and configured such that the introducer housing assembly can be releasably secured to the handheld housing to create operable communication between the handheld housing and the introducer housing assembly. Introducer housing assemblies in this context may also be referred to simply as introducer assemblies or second imaging members. The introducer housing assemblies herein may be disposable, and can be easily released from the handheld housing following the procedure or as desired by the operator, such as in the case of introducer assembly failure. When the introducer housing assembly is releasably secured to the handheld housing, the two components together may also be referred to together as a handheld device or assembly.

In this example, intubation system or assembly 1400 includes handheld housing 1410, which may include any other suitable feature described herein with respect to any other handheld housing, such as a display (screen), one or more internal actuators (e.g., one or more motors), electronics, one or more computer executable methods, firmware, a microprocessor, a blade coupler, a laryngoscope or laryngoscope coupler, etc. In some examples, housing 1400 may include an integrated first imaging member (e.g., laryngoscope), and in some examples the housing 1400 includes a laryngoscope coupler that is adapted to be releasably secured to a laryngoscope. In some examples, the housing 1400 is coupled to or comprises a video device that is not necessarily considered a laryngoscope but is adapted to provide video images. In some examples, the handheld housings herein do not include and are not adapted to be coupled to a laryngoscope.

In this example, system 1400 optionally includes a detachable cover 1460, which in this example include a first imaging member channel 1462 defining a lumen and a tracheal tube channel 1461. Any other suitable cover feature or description herein (including in any claim) may be incorporated into assembly 1400 in FIGS. 14A-14D.

Assembly 1400 includes an introducer assembly 1499 (which may be referred to herein as a second imaging member), which includes an introducer housing 1490 secured to moveable introducer 1450, wherein the introducer housing 1490 is sized and configured to be releasably secured to handheld housing 1410, and wherein the introducer assembly 1499 may be disposable.

In this example, handheld housing 1410 includes a plurality of electrical connections (FIG. 14B) that are adapted to be placed into electrical communication with corresponding electrical connections 1495 of the introducer housing (FIGS. 14C and 14D), which may facilitate at least one type of controlled movement of the introducer, which is described below. The handheld housing 1410 electrical connections are in communication with an on-board handheld housing controller that may be adapted to cause movement of the introducer by facilitation sending electrical signals to the electrical connections. For example, as described elsewhere herein, an on-board controller may include one or more processors and/or computer executable methods that facilitate the automated movement (e.g., via AI) of the introducer based on automatic or manual image recognition methods. Any of the suitable features of any other handheld housing herein that facilitates controlled movement of an introducer may be incorporated into the handheld housing 1410.

In this example, handheld housing 1410 includes one or more motors therein, wherein a motor is in rotational communication with or considered part of motor coupling 1413, which may comprise a motor shaft that is rotated when the motor rotates. In this example, the motor is adapted to, when activated, cause axial movement of the introducer, which is described below.

Figure 14A:
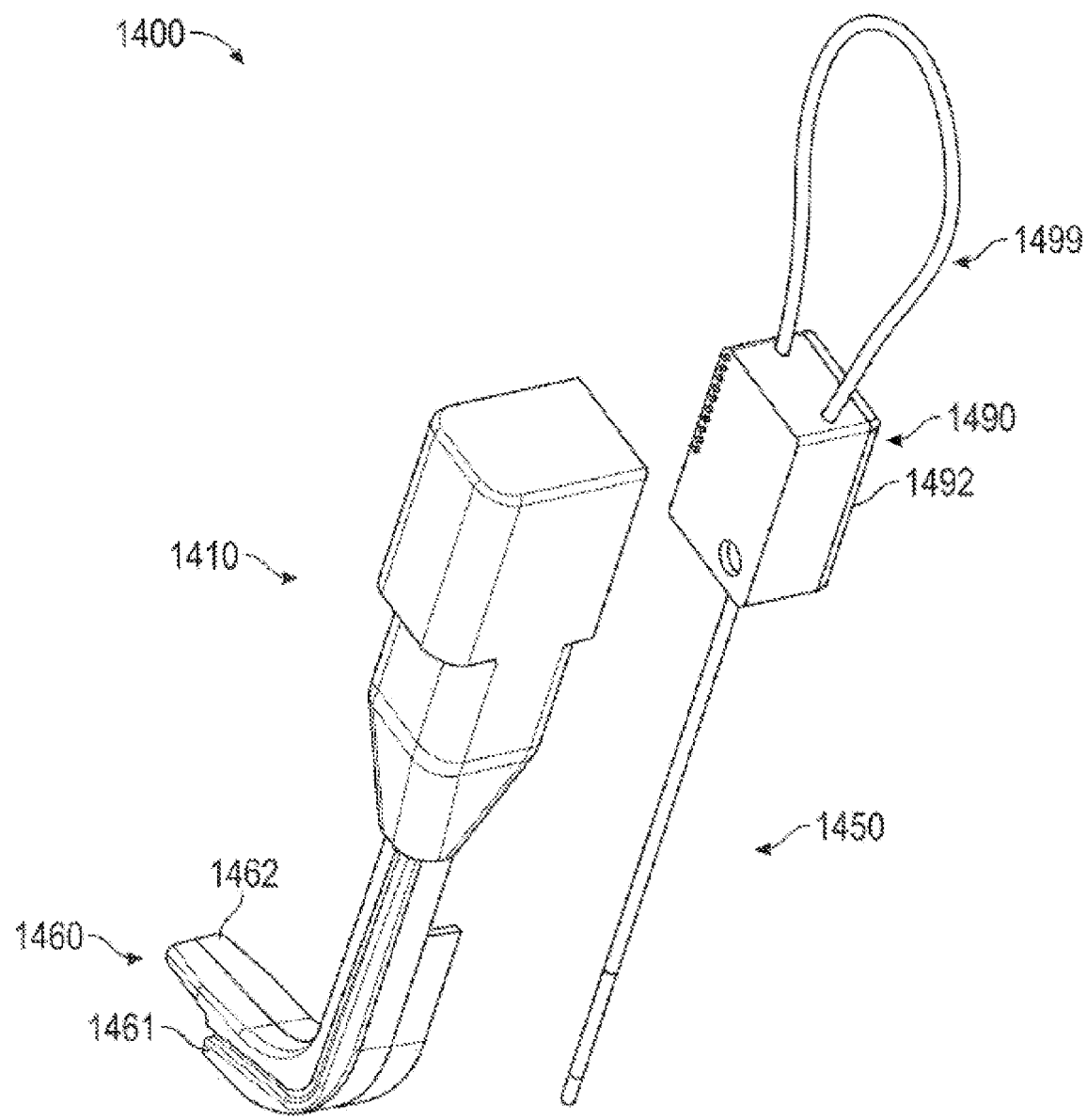
FIG. 14A illustrates an exemplary integrated and handheld dual-video tracheal intubation assembly.
Figure 14B:
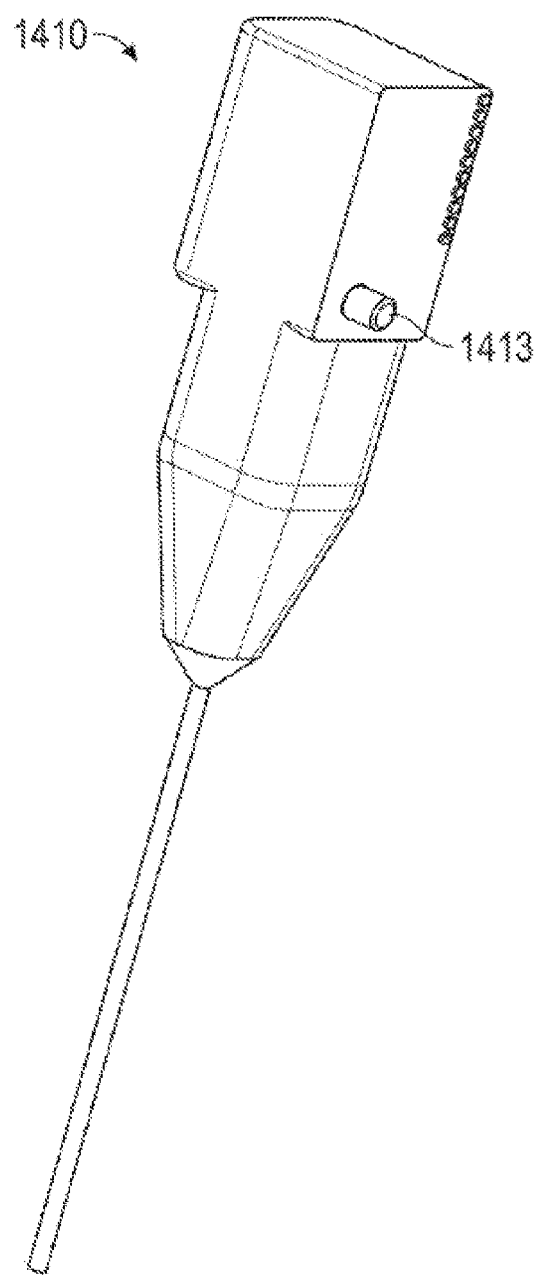
FIG. 14B illustrates an exemplary housing and first imaging member.
Figure 14C:
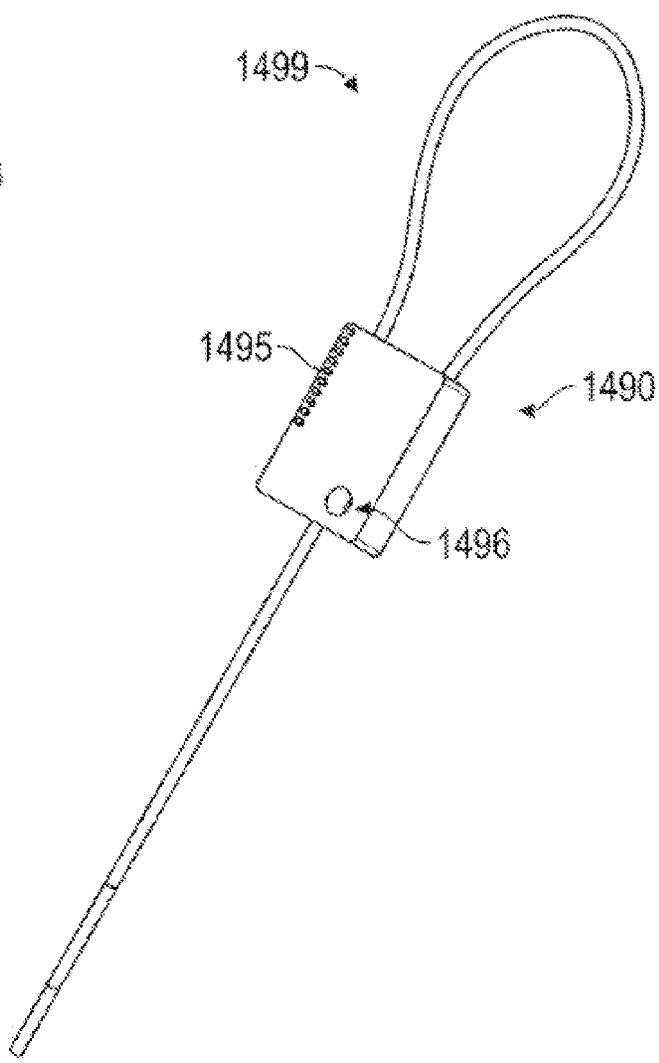
FIG. 14C illustrates an exemplary second imaging member.
Figure 14D:
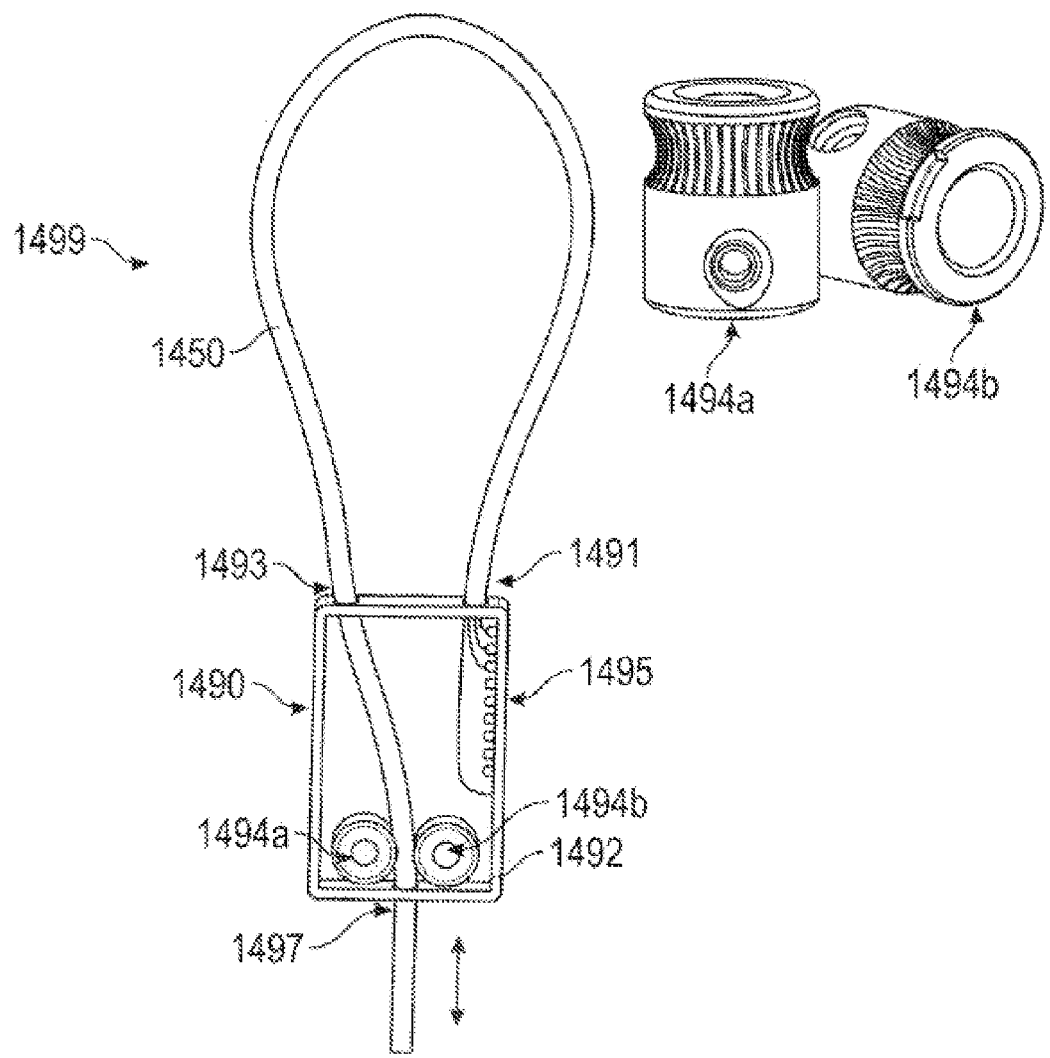
FIG. 14D illustrates a portion of an exemplary second imaging member.

FIGS. 14C and 14D illustrate exemplary features of introducer housing 1490 and introducer 1450. In this embodiment, introducer housing 1490 includes an electrical coupling 1495 comprising a plurality of electrical connects as shown that are adapted and positioned to create electrical communication with the electrical connections of the handheld housing (FIG. 14B) when the introducer assembly 1499 is releasable secured to the handheld housing 1410. The electrical coupling between the handheld housing and the introducer housing may provide for one or more types of controlled movement of the introducer. It is of note that the electrical coupling is optional, and in alternative designs the electrical connections may be replaced with one or more motors in the handheld housing. Electrical coupling 1495 may also comprise a connection to communicate image data from the introducer to the handheld housing.

The introducer housing 1490 is adapted to releasably couple to the handheld housing, wherein the coupling creates operable communication between one or more controllers in the handheld housing and the introducer. In this example, the coupling creates both electrical communication and mechanical communication, but in other examples it may be solely mechanical or solely electrical. In this example, a mechanical coupling is adapted to control axial movement of the introducer, and electrical coupling is adapted to cause one or more types of deflection of the articulating section of the introducer shown in FIG. 14C, which may facilitate 360 degrees of deflection.

In this example, a motor coupling includes a motor in the handheld that is rotationally coupled to a shaft, as shown in FIG. 14B. The motor shaft is sized and configured to be disposed within motor coupling 1496 is the introducer housing, which is shown in FIG. 14C. The motor shaft may be sized and configured to interface with an inner surface of one of the rollers 1494a or 1494b, shown in FIG. 14D. Motor activation thus drives the rotation of one of the rollers 1494a or 1494B, both of which are adapted to rotate about an axis in this example. One end region of the introducer 1450 (optionally an end of a flexible introducer shaft) is fixed relative to the housing 1490 at location 1491, while the introducer and housing are adapted such that the introducer can move axially relative to the housing 1490 at regions distal to location 1491. Introducer 1450 is shown disposed through an aperture 1493 in housing body 1492 and through an aperture 1497 in housing body 1492.

The handheld housings may be able to be used with introducers of different sizes. The motor shaft may, for example, be a common or universal driving element that may be sized and configured to fit within rollers of varying size, depending on the dimensions of the rollers and/or the introducer. This is an example of how a universal handheld may be able to be releasable secured to different introducers, which may have at least one difference is size/dimension (e.g., diameter). This may allow the handheld housing to be used in pediatrics as well as with adults.

As used herein, an introducer housing may or may not completely surround or enclose the introducer. For example, an introducer housing may have one side that is open to the ambient environment and still be considered an introducer housing herein.

Introducer 1450 is disposed between rollers or wheels 1494a and 1494b, as shown, such that rotation of the rollers in opposite directions towards the introducer causes axial movement of the introducer, as indicated by the arrow in FIG. 14D. Rotation of the rollers in a first manner may cause distal movement, and rotation in the opposite manner may cause proximal movement. Any other disclosure herein related to controlled axial movement (e.g., such as axial distances, e.g., 10-40 cm) may be incorporated into the disclosure of FIGS. 14A-14D. One or both of the rollers may have a groove or other frictional interface, similar to that shown in top right in FIG. 14D, while in alternatives one or more rollers may have less pronounced teeth or grooves. In alternatives, one or more of the one or more rollers may be made out of a polymeric, plastic so as to reduce the likelihood of or avoid damage to the introducer shaft. The rollers may have a smooth interfacing surface or they may have non-smooth interfacing surfaces.

The introducer housings herein may include a body (such as housing body 1492), wherein the housing body may comprise one or more components, optionally two or more components that secured together (e.g., with adhesive, welding, etc.) to at least partially define the housing body.

The introducer housing assemblies herein may include a plurality of electrical couplings 1495 (e.g., comprising pins and/or vias) that may each be coupled to a wire (three exemplary wires shown in FIG. 14D), wherein the individual wires may each extend through the introducer shaft or be in electrical communication with a wire that extends through the introducer shaft. For example, any of the wires (e.g., four-nine) may communicate a video signal from a camera at a distal end region of the introducer (e.g., FIG. 14C), or the wire may facilitate deflection control of the articulating section of the introducer, such as with shape memory material (e.g., nitinol) or bi-metal wires (e.g., 5-8 wires), for example. A general concept of communicating an electrical signal through a wire comprising shape memory material to cause a shaft to deflect has been described, and the basic concept may be used to incorporate one or more of such wires to cause deflection of the introducer articulating sections herein. For example, electrical signals may be communicated to one or more introducer wires to cause distal sections thereof to transition between shape memory states, which can be used to control the deflection of the introducer in one or more directions. Any of the wires herein may also comprise bi-metal wires, which may also be used to cause deflection of the introducer by communicating signals to and through the one or more wires. An additional electrical signal can be transmitted to the wire to cause a distal region of the wire to change shape back to an original, or non-deflected, or straightened shape. Electrical signals may be communicated to any combination of wires to create and cause any desired deflection or configuration of the articulating section, which may be controlled automatically by AI, for example. For example, deflection can be caused by changing the shape of any combination of the wires in the introducer, which can be used to create a variety of shapes and configuration of the deflectable section of the introducer.

FIGS. 14A-14D illustrate an example of a system that uses mechanical coupling to control axial movement of the introducer, and electrical coupling to cause tip distal end region deflection of an articulating section of the introducer, an example of which is shown in FIG. 14C.

Any of the disclosure herein related to automatic and/or manual introducer control may be incorporated in system 1400. For example, the deflection of the distal region of the introducer using one or more of shape memory material (e.g., nitinol) or bi-metals can be used to control the deflection of the introducer in one or more of any of the automatic modes and/or manual modes herein, including partial automatic and partial manual.

As can be seen in FIG. 14D, the axial motion of the introducer is controlled (e.g., force applied) at a location that is distal to the proximal end of introducer shaft (which in this example is coupled to the introducer housing at location 1491). The forces applied to the shaft that cause the axial motion are applied where the introducer shaft interfaces with the rotatable rollers. While not shown in FIG. 14A, the introducer 1450 is generally adapted to guide the advancement of a tracheal tube, for which any relevant disclosure herein may be incorporated into this example. By controlling the axial motion of the introducer (e.g., force applied) at a location that is closer to the tracheal tube, as in this example, axial movement of the introducer is less likely to cause buckling of the introducer. Applying force to the introducer at a location further from the tracheal tube may increase the likelihood of introducer shaft buckling, for example. An additional exemplary advantage of controlling the axial introducer movement at one or more particular locations that are relatively close to a tracheal tube is that better force feedback may be provided if desired or required.

Any of the handheld housings herein (e.g., 1410) may comprise an encoder on a motor to control the axial distance that the introducer is moved. Additionally or alternatively, any of the introducers herein may include a plurality of visual markings thereon (e.g., axially spaced lines) that may be used to control the axial travel of the introducer. Additionally or alternatively, any of the blades herein may include a RFID tag (or EEPROM) that may be used to control initial introducer advancement and/or to communicate to the system a blade type, since blade type can affect first visuals.

Any of the components that may include an introducer housing (e.g., 1490) that can be releasably secured to a handheld housing may include a RFID tag (or EEPROM), which may be adapted to notify to the system or control what type of introducer is being used, such as information related to introducer diameter, introducer length, video resolution, and/or being adapted to enable and disable certain features, such as reuse.

In any of the examples herein, an introducer housing (e.g., 1490) may be adapted to be releasably secured to a back surface or a side surface of the handheld housing (e.g., 1410).

In the embodiment in FIG. 14C, the section of the introducer referred to as extra loop in the figure is shown not encased in a housing (until a portion of the introducer is fed through housing 1490). In alternative designs, this region of the introducer may be at least partially contained or disposed in a housing, which may provide protection to the introducer and possibly reduce the likelihood of objects being caught in or snagged by the loop region of the introducer. Such a housing may be fixed relative to housing 1490 or be a part of housing 1490 such that the introducer may move relative to the additional loop housing. For example, this loop region of the introducer may be disposed in a cylindrical housing that is in a fixed relationship relative to housing 1490. Alternatively, the loop region of the introducer may be disposed within a helical housing or container that is secured to housing 1490, wherein the introducer can be movable relative to the helical housing to facilitate axial movement.

In the example in FIGS. 14A-14D, deflection is caused by wires in the introducer that are adapted to change shape in response to signals communicated thereto. In alternatives, deflection of the introducer may instead be driven by additional motor couplings between the handheld housing and the introducer housing. In these alternatives, the system may include mechanical couplings for axial movement of the introducer as well as deflection of the introducer. In these alternatives, wires in the introducer can be in communication with one or more motors, wherein the motors can be used to tension the wires and cause deflection of the steerable section of the introducer. For example, the system may include two or four additional motors to facilitate deflection of the deflectable section. For example, the system may include four motors for tensioning pull wires (or other elongate tensioning elements) to cause deflection and/or transitioning back towards a straightened configuration. Including four additional motors may help maintain tension in pull wires when a pull wire at a different circumferential location is tensioned to deflect the housing, which can help with backlash by reducing slack in the other pull wires that were not tensioned for deflection. Having four motors, for example, may help maintain tension on all pullwires that aren't being tensioned to deflect in that particular location. Alternatively, the system may include two additional motors, wherein the additional motors may be adapted to deflect the deflectable section of the introducer.

Any of the introducer housings herein may also include or house therein a lumen that me be adapted as a working lumen. The housing may include one or more ports in communication with one or more lumens to allow for the delivery of one or more substances and/or devices into the working lumen, for example. A schematic illustration of a port and lumen are shown in FIG. 14D. For example, housing 1490 may be adapted to couple to and receive a syringe to facilitate delivery of one or more substances, such as one or more therapeutics. It may be beneficial to have an agent delivery port and lumen in the housing, which may be disposable and may not need to be cleaned. Additionally, a port and lumen may allow for the delivery of one or more other devices, such as one or more diagnostic (e.g., ultrasound imaging) and/or therapeutic devices, or other medical tools. One or more delivery ports may be on a side or region of the housing other than that shown in FIG. 14D, such as through a lower side or top side. Additionally, the general location 1491 where the introducer is fixed (other fixation locations 1491 may be used) may include a port into which a substance or device may be delivered. The fixed location may provide more functionality and options at that location since the introducer does not move relative to the housing at that location. Additionally, any of the introducers herein may thus also include a working channel or working lumen through which any device and/or substance may be delivered or retrieved.

As discussed above, an exemplary benefit of some embodiments herein is that a distal end of an introducer and a distal end of a first imaging member may be initially positioned in a patient as a coupled unit (e.g., both coupled to a handheld housing). This initial positioning of the introducer may allow the system to advance the introducer immediately sufficiently distally inside the patient's airway and in a such a manner that a substantially shorter distance would be required for the introducer to navigate to the desired location (e.g. laryngeal inlet). This would be opposite to the standard situation when the introducer were not coupled to the handheld and had to be advanced distally from the starting point located further away from the desired location. For example, in some uses, the introducer may only be about 2-7 cm from a desired location when inserted into its initial position when coupled to the first imaging member and the assembly in general. The introducer may then optionally be guided to the desired location while utilizing imaging and the resultant robotic control from the first imaging member only, because the first imaging member is able to provide the reliable and stable anatomic landmarks by viewing a larger anatomical region, even in a difficult airway situation. One of the exemplary benefits with these examples is that the introducer and first imaging member may be coupled to a common assembly in a manner such that fields of view of the introducer and first imaging member are at least partially overlapping.

An exemplary benefit of some of the embodiments herein that incorporate a common handheld housing to which an introducer and a first imaging member are coupled is that the overall footprint or envelope occupied by the structural devices when placed in the patient may be smaller or at least more reliably controlled, which in the case of tracheal intubation may further improve the first pass success rate, shorten intubation time and lower the risk of injury to the patient.

Any of the image processing herein may take place inside or outside of the handheld housing. For example, image processing may at least partially take place in a device that is external to the handheld housing, such as a computer with a graphics processing unit, smartphone, etc. The handheld may be in communication (wired or wireless) with the external device, and optionally wherein information related to acquired optical information is communicated from the handheld to the external device for processing. The external device may also be adapted to communicate information to the handheld housing to facilitate control of the introducer, which is described in more detail herein.

Figure 17A:
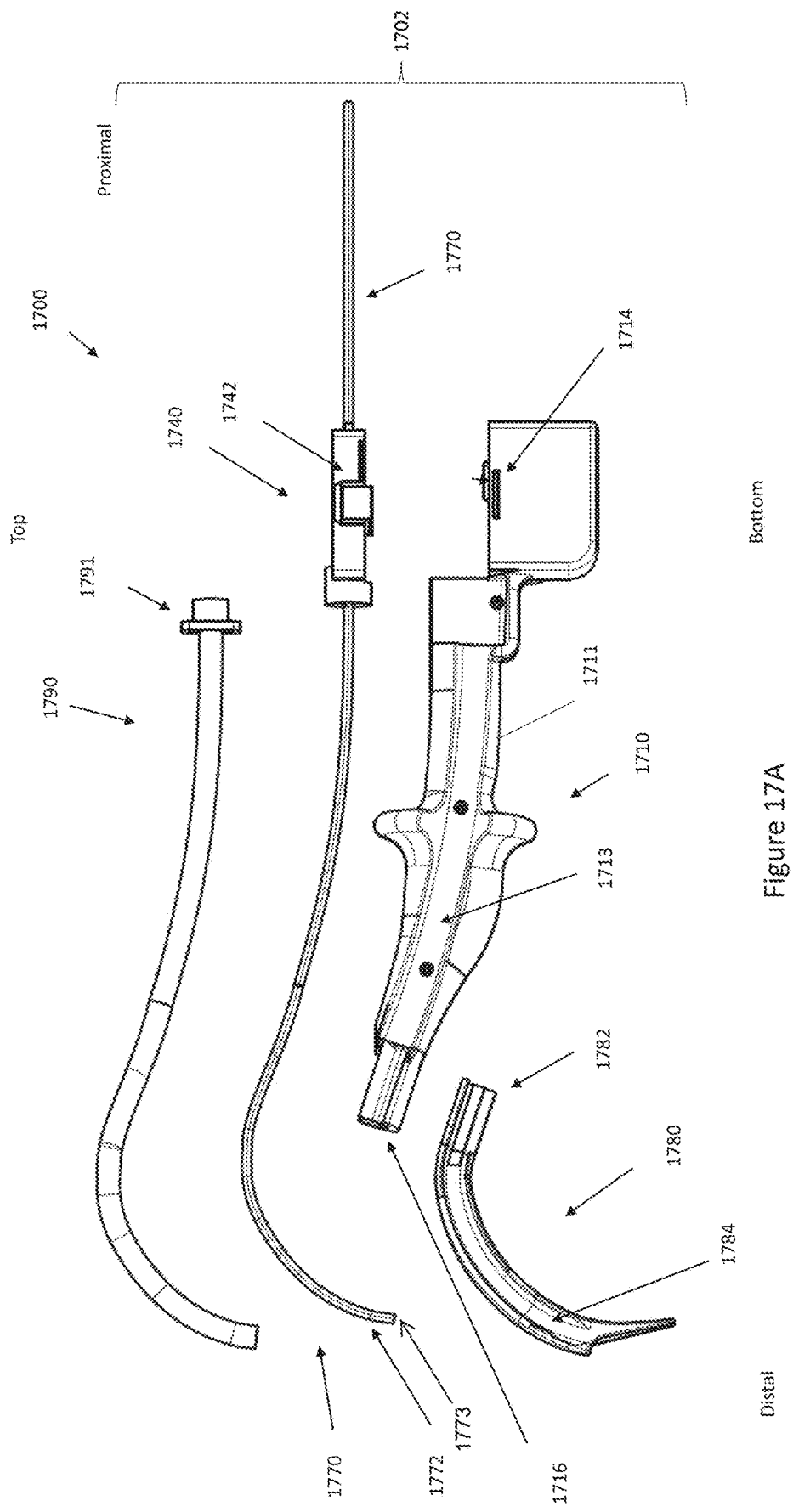
FIGS. 17A and 17B illustrate side and top views, respectively, of an exemplary integrated and handheld dual-video tracheal intubation assembly (first imaging member not shown), shown unassembled.
Figure 17B:
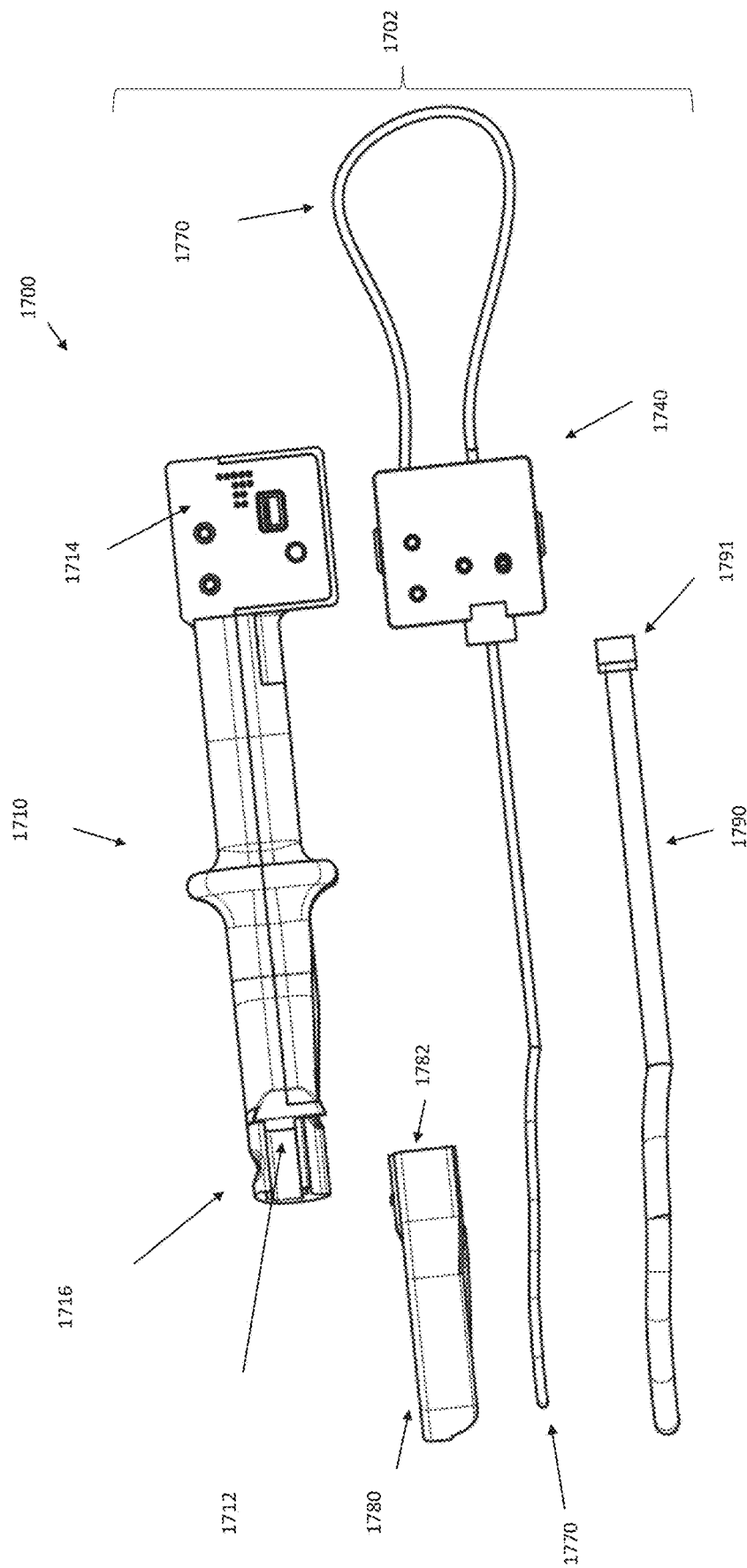
Figure 17C:
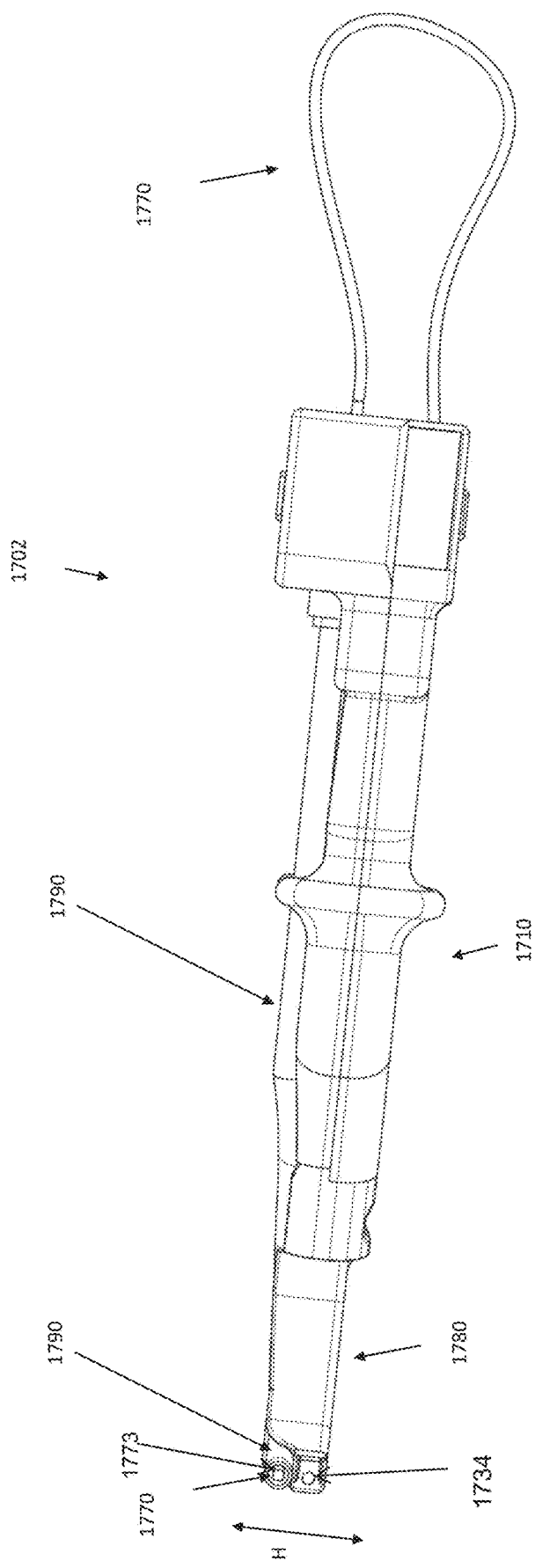
FIG. 17C illustrates a bottom view of an exemplary integrated and handheld dual-video tracheal intubation assembly, shown assembled.
Figure 17D:
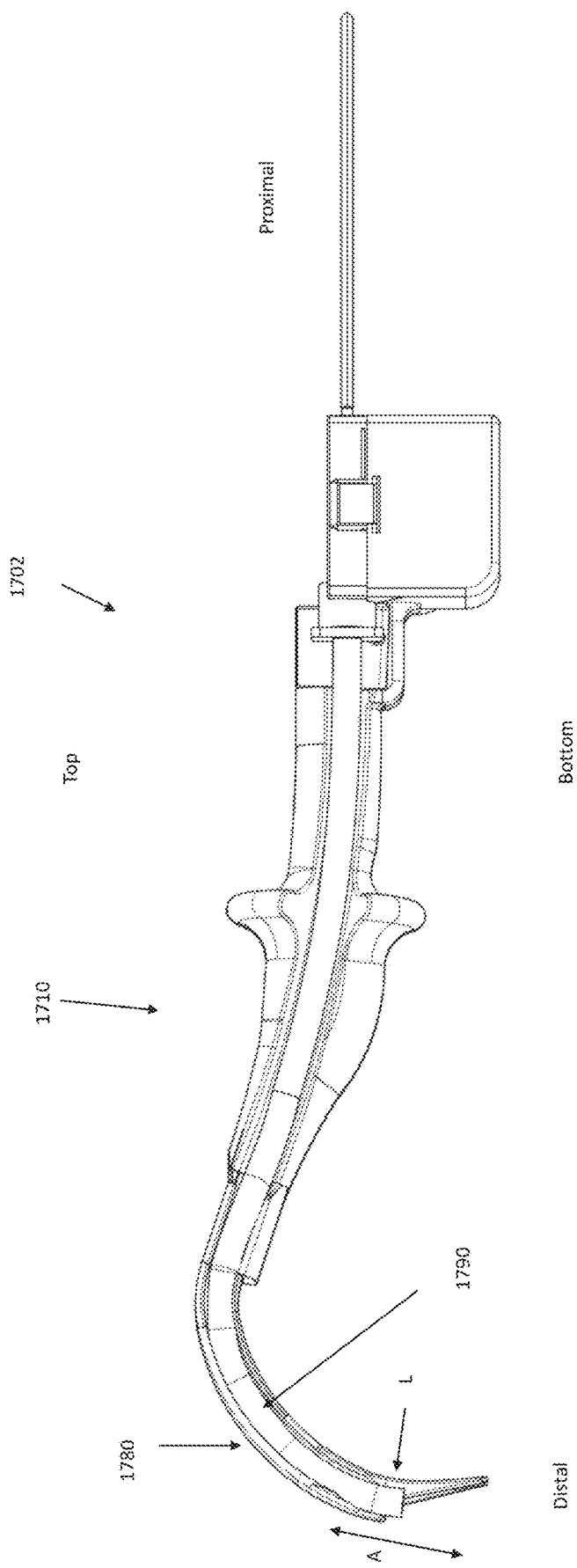
FIG. 17D illustrates a side view of an exemplary integrated and handheld dual-video tracheal intubation assembly, shown assembled.
Figure 17E:
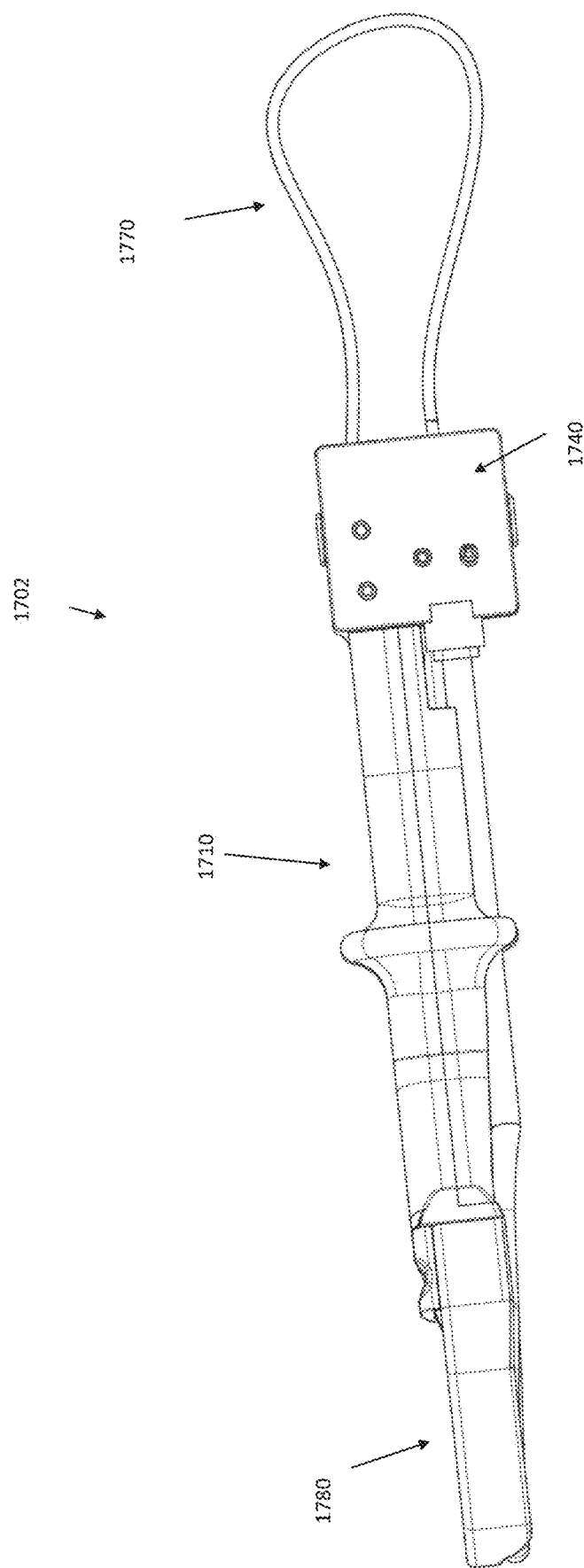
FIG. 17E illustrates a top view of an exemplary integrated and handheld dual-video tracheal intubation assembly, shown assembled.
Figure 17F:
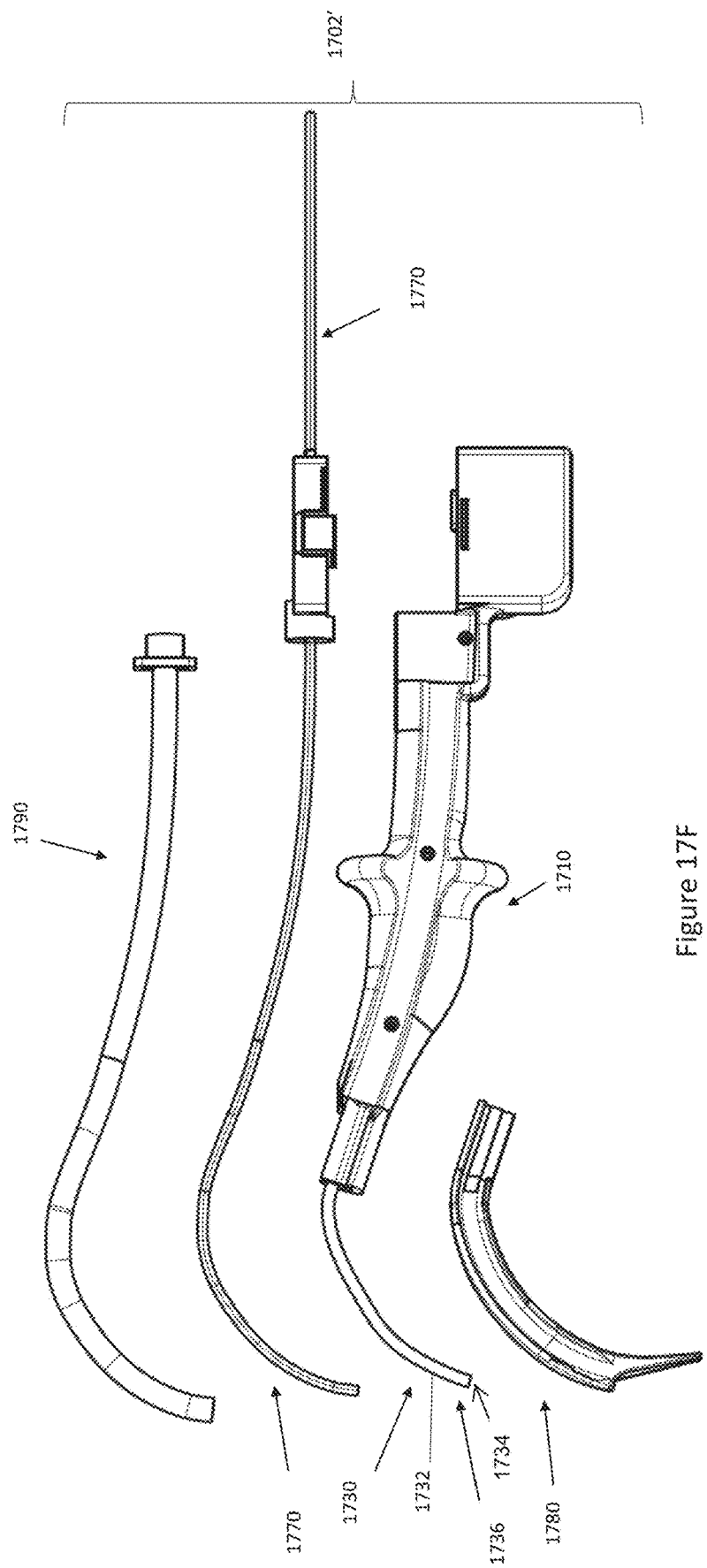
FIG. 17F illustrates a side view of an exemplary integrated and handheld dual-video tracheal intubation assembly, shown unassembled.

FIGS. 17A-17G illustrate at least a portion of exemplary intubation system 1700, wherein FIGS. 17A and 17B are unassembled views of exemplary integrated and handheld dual-video tracheal intubation assembly 1702, wherein this and other integrated assemblies herein may simply be referred to as an assembly. Any of the individual components of any of the assemblies herein may be assembled together prior to the procedure and thereby assemble and create the assembly. FIGS. 17C-E illustrate the assembled assembly 1702. Assembly 1702 includes housing 1710, which includes a first imaging member coupler 1712, a second imaging member coupler 1714, and a cover coupler 1716. Housing 1702 is configured to be releasably coupled to cover 1780, first elongate imaging member 1730 (an example of which is shown in FIGS. 17F and 17G)), and an optionally disposable second elongate imaging member 1740. Assembly 1702' (which may include any suitable feature of assembly 1702, and vice versa) includes first elongate imaging member 1730 with a first coupling region that is sized and configured to be releasably coupled to first imaging member coupler 1712, as shown in FIGS. 17F and 17G. First elongate imaging member 1730 includes elongate flexible body 1732 and a first image sensor 1734 (e.g., a video camera) disposed at a distal region 1736 of elongate body 1732.

Assembly 1702 also includes second elongate imaging member 1740, which includes second coupling region 1742 that is sized and configured to be releasably coupled to second imaging member coupler 1714 of housing 1710. Second elongate imaging member 1740 includes a flexible and navigable elongate endotracheal tube introducer 1770 ("introducer"), at least a portion of which is deflectable. Introducer 1770 is sized to be disposed within an endotracheal tube 1790 and to allow endotracheal tube 1790 to be moved axially over introducer 1770. Second imaging member 1740 includes second image sensor 1773 (e.g., a video camera) disposed at a distal region 1772 of introducer 1770. As is described in more detail below, introducer includes a first end or first end region secured to a housing of second imaging member and a movable portion that is movable relative to the housing of the second imaging member.

Assembly 1702 also includes cover 1780 with a cover coupling region 1782 that is sized and configured to be releasably coupled to the cover coupler 1716 of housing 1710. Cover includes an elongate channel defining an elongate lumen, the elongate channel sized and dimensions such that at least a portion of elongate body 1732 of first imaging member 1730 is disposed within the elongate lumen when the first coupling region of the first imaging member 1730 is releasably coupled to first imaging member coupler 1712 and when the cover coupling region 1782 is releasably coupled to cover coupler 1716.

Cover 1780 further includes endotracheal tube channel 1784 disposed on a side of cover 1780 as shown, the endotracheal tube channel 1784 sized and dimensioned to interface with endotracheal tube 1790 and restrict movement of endotracheal tube 1790 relative to cover 1780 in at least one direction. Endotracheal tube channel 1784 is further configured to allow endotracheal tube 1790 to be laterally moved relative to endotracheal tube channel 1784. In this example channel 1784 includes a depression or trough formed in a side of cover 1780 that is dimensioned and configured to interface with a portion of the outer wall of endotracheal tube 1790, and in some embodiments channel 1784 may have a cross sectional configuration that includes a surface forming a partial circle to interface with a circular outer surface of endotracheal tube 1790.

Endotracheal tube 1790 includes a lumen that is sized to movably receive introducer 1770 therein, as shown in FIG. 17C.

Assembly 1720 further includes one or more actuators disposed within housing 1710 and configured and positioned such that when second coupling region 1742 of the disposable second elongate imaging member 1740 is releasably coupled to second imaging member coupler 1714 of housing 1710, the actuator is configured to facilitate the controlled robotic movement of introducer 1770 and second images sensor 1772 (e.g., a video camera) relative to first image sensor 1734 (e.g., a video camera).

System 1700 may also include one or more processors, which may be part of the assembly or which may not be part of the assembly. The one or more processors may be configured to receive as input information indicative of a signal received from the first image sensor (e.g., video camera) when the first image sensor is disposed in an upper airway of a patient, and cause communication to an actuator within the housing (e.g., housing 1710) to control the robotic movement of the introducer and the second image sensor (e.g., video camera) relative to the first image sensor and toward one or more upper airway anatomical landmarks. Details about exemplary methods of use are described in more detail elsewhere herein.

As is described elsewhere herein, an exemplary advantage of assemblies herein is that, once assembled, they are sized and configured such that they can be held and moved as an assembly with a single hand of an operator. Assembly 1702 is an example of an assembly that is sized and configured such that when the first coupling region of first imaging member 1730 is releasably coupled to first imaging member coupler 1712, when second coupling region 1742 is coupled to second imaging member coupler 1714, when cover coupling region 1782 is releasably coupled to cover coupler 1716, and when endotracheal tube 1790 is releasably coupled to endotracheal tube channel 1784, the assembly, including the first image sensor and the second image sensor, is movable as an integrated unit with the single hand of the operator.

FIG. 17C illustrates an assembled view of assembly 1702, referred to a bottom view in which the first and second image sensors can be seen. Horizontal distance between images sensors is measured in the direction "H" as labeled in FIG. 17C.

FIG. 17D illustrates a side assembled view of assembly 1702. Relative axial distance between image sensors when the assembly is assembled as is described herein is measured in the axial direction "A" as shown in FIG. 17D. It is understood that the axial direction "A" depends on the orientation of the assembled assembly. For example, if the assembly in FIG. 17D were rotated counterclockwise 90 degrees, axial direction "A" would similarly be rotated 90 degrees.

As is set forth herein, an exemplary advantage of some assemblies herein is that they are dimensioned and configured to be held and moved by a single hand of an operator. When assembled, the relative couplings between the housing, cover, first elongate imaging member, and endotracheal tube maintains the first image sensor at a distance from the second image sensor prior to actuation of the actuator, examples of which are shown in FIGS. 17C-17E. In some uses it may be preferable that the first and second image sensors are axially aligned or as close to axially aligned as possible when the assembly is assembled. In some instances, the image sensors are axially aligned. In some instances they are substantially axially aligned. In some instances, the first and second image sensors are maintained to be axially "A" within 3 cm of each when the assembly is assembled. In any these instances, the horizontal distance H between first and second image sensors may be no greater than 2 cm when the assembly is assembled. The maintained proximity of the images sensors when assembled may help provide the overall smaller profile or footprint of the assembly, which helps make it easier and safer for a single operator to hold a dual-video intubation assembly in a single hand.

FIG. 17E shows a top view of assembled assembly 1702 in which second imaging member 1740 is coupled to housing 1710, as shown. The first and second image sensors are facing down or into the page in this top view.

FIGS. 17F and 17G illustrate assembly 1702' that may be include any of the disclosure from assembly 1702. FIGS. 17F and 17G show first imaging member 1730, which includes elongate flexible body 1732 and a first image sensor (e.g., video camera) disposed at a distal region 1736 of flexible body 1732. First imaging member 1730 may, in some embodiments, be integrated into and considered part of the cover, wherein the first imaging member and cover are releasably coupled to housing 1710 as a subassembly. In some examples, first imaging member 1730 may be releasably coupled to the housing before use separately from the cover. In some examples, the housing (e.g., housing 1710) and first imaging member (e.g., imaging member 1730) may be an integrated unit and don't need to be coupled by an operator prior to the medical procedure. It may be advantageous to be able to remove the first imaging member from the housing and reuse the housing, such as if a differently sized first imaging member is needed for a subsequent procedure (e.g., between different patients or pediatric patient versus adult patient), advantages of which are described elsewhere herein. It is thus understood that any of the assemblies herein may include a housing and first imaging member that are integrated, a cover and first imaging member that are integrated and coupled to the housing as a unit, or a cover and a first imaging member that are separately releasably coupled to the housing. Any component in system 1702' that is not labeled or described is understood to be the same as the corresponding component or subassembly in assembly 1702.

FIGS. 18A-18J illustrate exemplary housing 1710. It is understood that any of housing features described with respect to housing 1710 may be incorporated into any of the housings herein, which may be part of any of the assemblies herein. Any of the labels to housing 1710 from FIGS. 17A-17G may be included in FIGS. 18A-18J even if not labeled in the figures.

Housing 1710 includes communication region 1720 that is adapted to communicate with optionally disposable second imaging member 1740. Communication region 1720 may be configured to be in one or more of electrical, mechanical, optical and/or video communications with second imaging member 1740 when second imaging member 1740 is releasably coupled to housing 1710 (see FIGS. 17C-17E). In this example, communication region 1720 includes mechanical interface 1721 and mechanical interface 1722 that are adapted to mechanical interface with second imaging member 1740, described in more detail below. In this example, mechanical interfaces 1721 and 1722 are positioned and configured to mechanically interface with corresponding features on second imaging member 1740 and cause deflection of the introducer via one or more pull wire or other tensioning elements, as described below. Mechanical interfaces 1721 and 1722 may be actuated by one or motors, or example, that may be disposed in housing 1710. Motors in this context may be considered part of the robotic control mechanism that is adapted to robotically control the movement of the introducer, optionally in response to the image processing described elsewhere herein. Motors in this type of design may be considered to be actuators as that term is used herein, or one or more motors may be considered to be part of an actuator, wherein actuator may refer to one or more separate components operating together as a mechanical and/or electrical system, for example (e.g., motor and drive shaft, etc.).

The assemblies herein include one or more actuators 1761 (see FIG. 20) that facilitate (directly or indirectly) the robotic controlled movement of the introducer. Motors within the housing 1710 as described in this example are an example of actuators 1761 within the assembly. The pullwires that are in this exemplary embodiment are also considered to be actuators, and in this example they are disposed in exemplary second imaging member 1740.

Communication region 1720 may also further include mechanical interface 1723 that is positioned to mechanically interface with the second imaging member and cause or facilitate axial movement of the introducer, which is described in more detail below. One or more motors in the housing may cause the mechanical movement of mechanical interface.

Communication region 1720 of the housing optionally includes optical sensor 1724 that is adapted to optically track the axial movement and/or axial position of the introducer as is moved axially relative to the optical sensor, and is described in more detail elsewhere below. Other sensors may be used to track the axial movement and/or position of the introducer.

Communication region 1720 also optionally includes a plurality of electrical connectors 1725 (e.g., a plurality of electrical connects), which can be adapted to interface with a plurality of corresponding connectors on the second imaging member 1740 to receive data communicated from the second image sensor (e.g., video camera signal) to the housing where it may be processed or communicated to an external device and/or display of the device for processing. Exemplary image processing and robotic control (automatic and/or manual robotic control) utilizing the second image sensor data is described elsewhere herein.

Figure 18C:
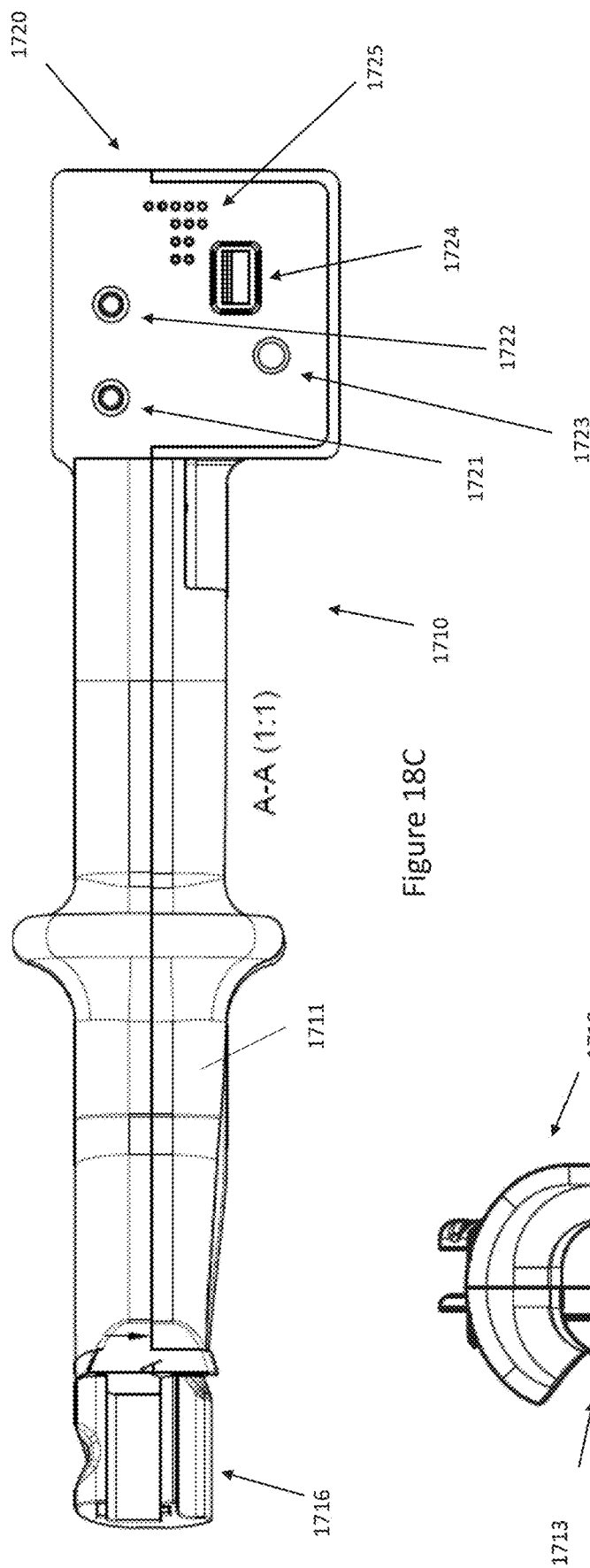
FIG. 18C shows a top view of the exemplary housing from FIG. 18A.
Figure 18D:
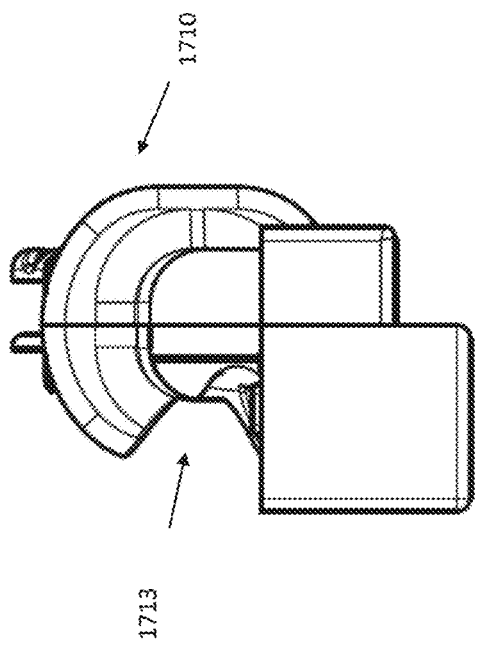
FIG. 18D shows a front, end view of the exemplary housing from FIG. 18A.
Figure 18F:
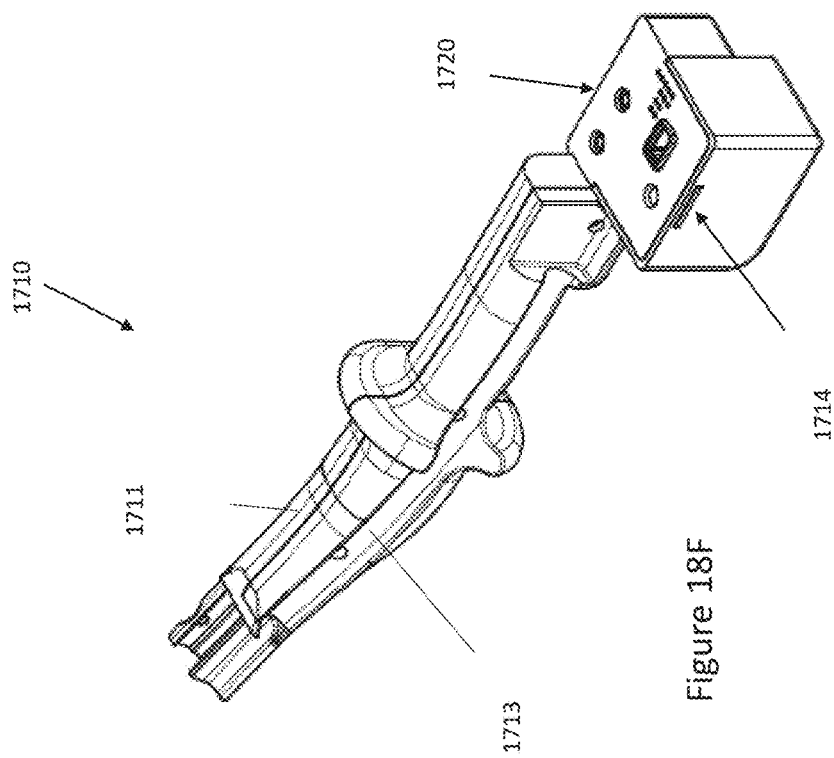
FIGS. 18E and 18F show perspective top views of the exemplary housing from FIG. 18A.
Figure 18E:
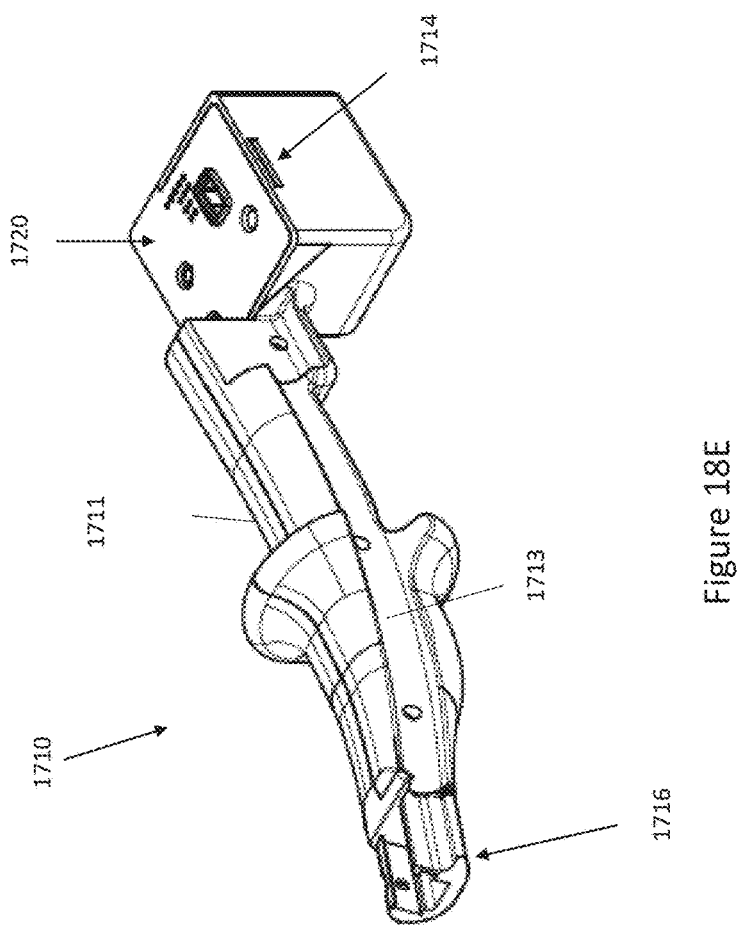
Figure 18G:
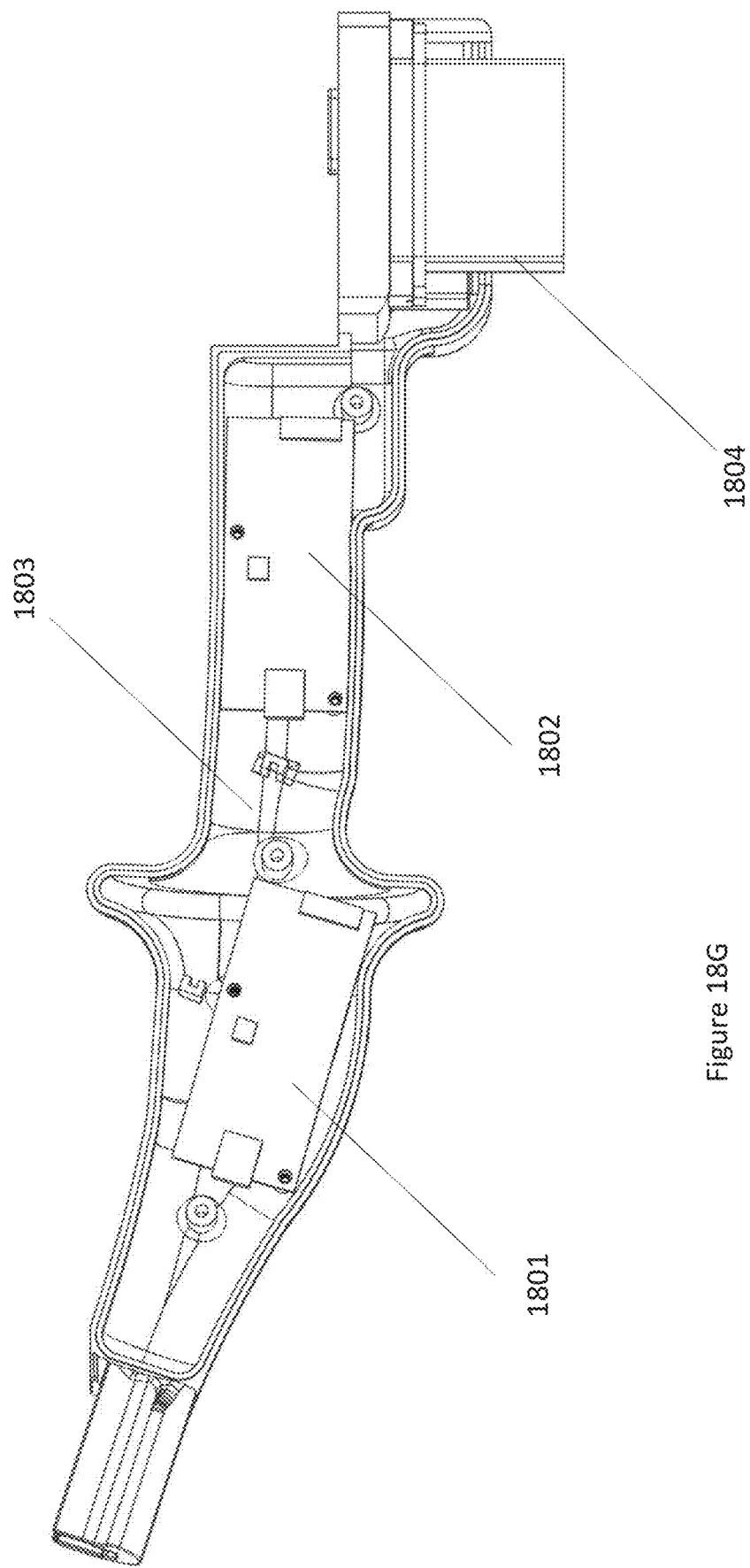
FIGS. 18G, 18H, 18I and 18J illustrate an exemplary housing and optional internal components.
Figure 18H:
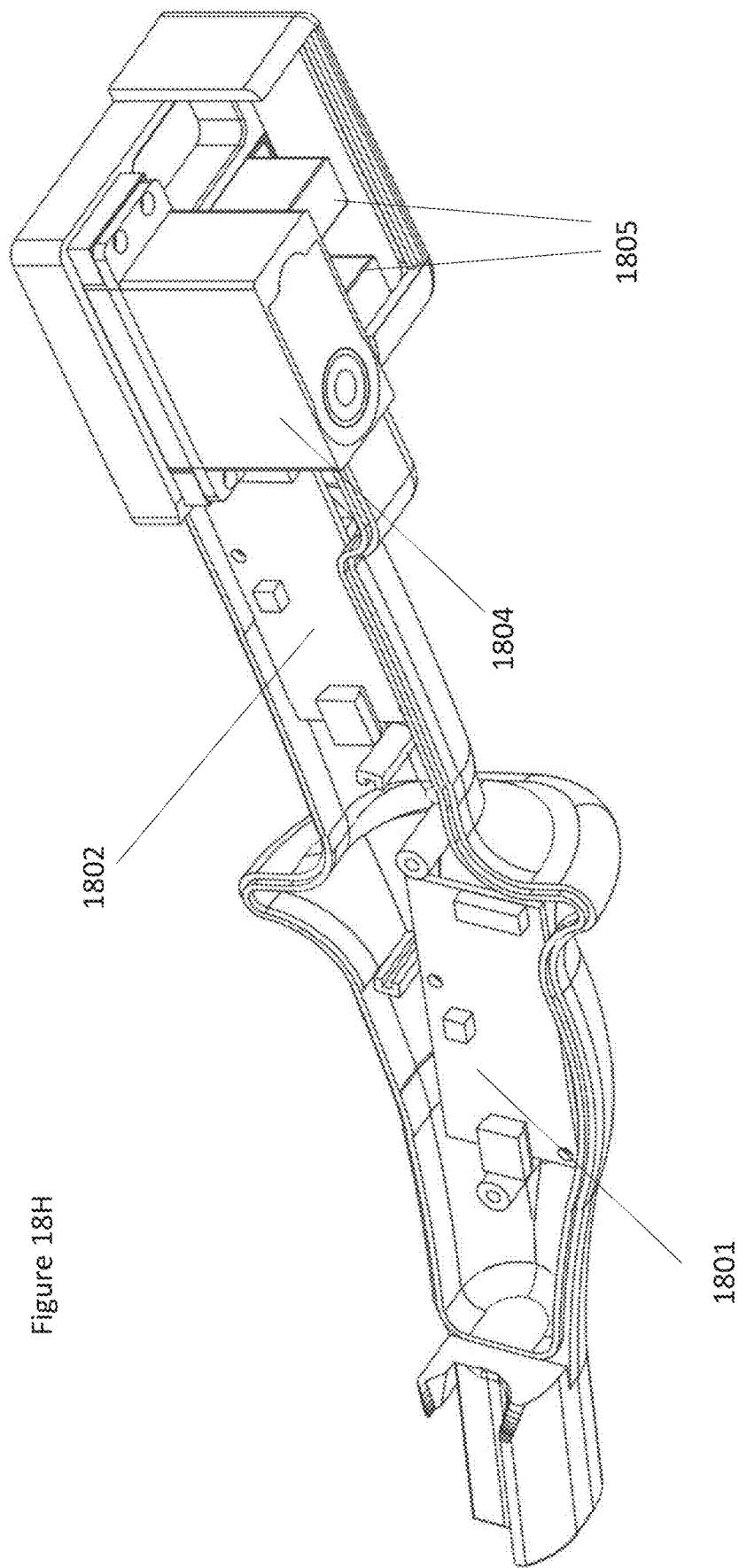
Figure 18I:
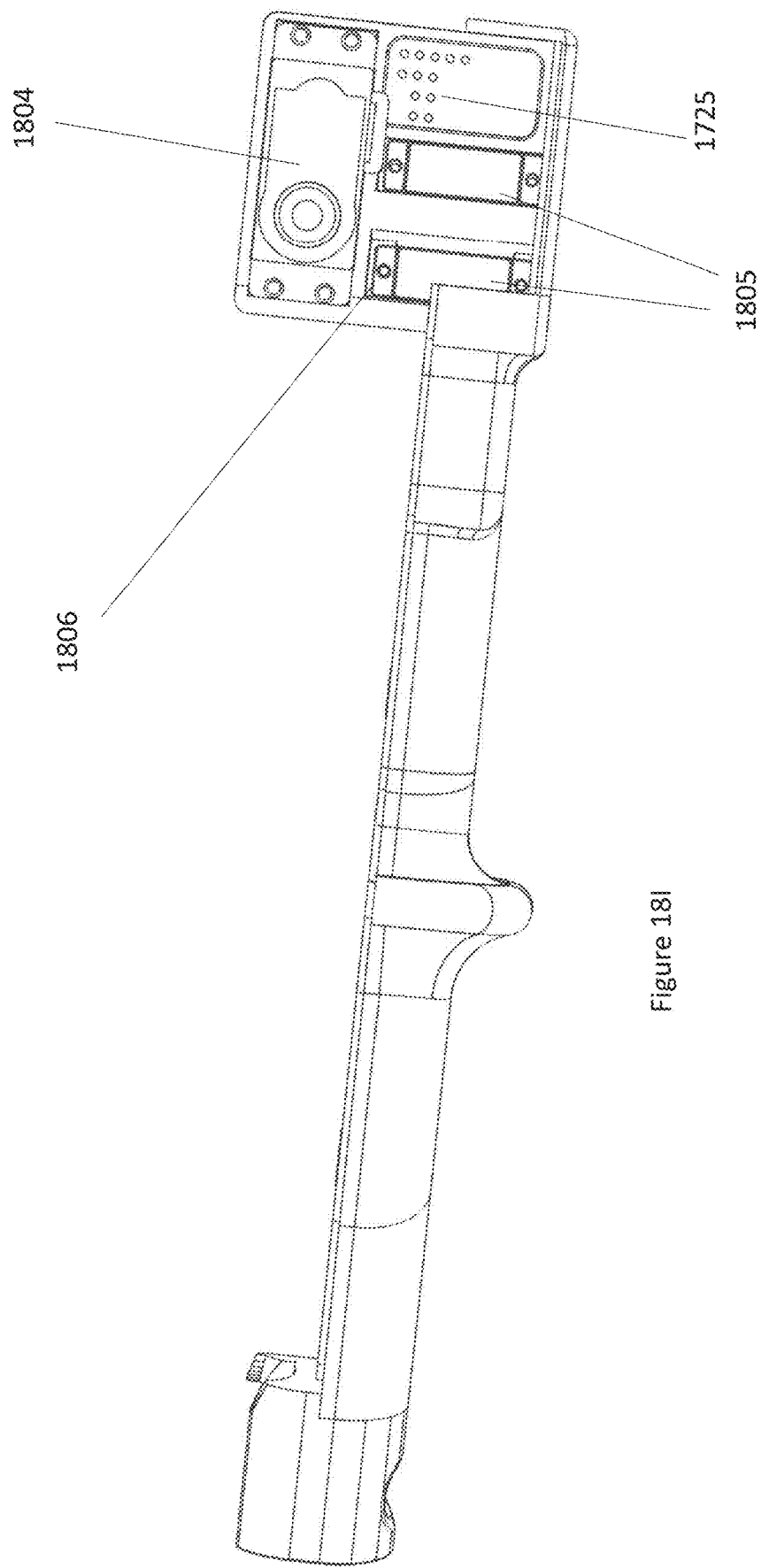
Figure 18J:
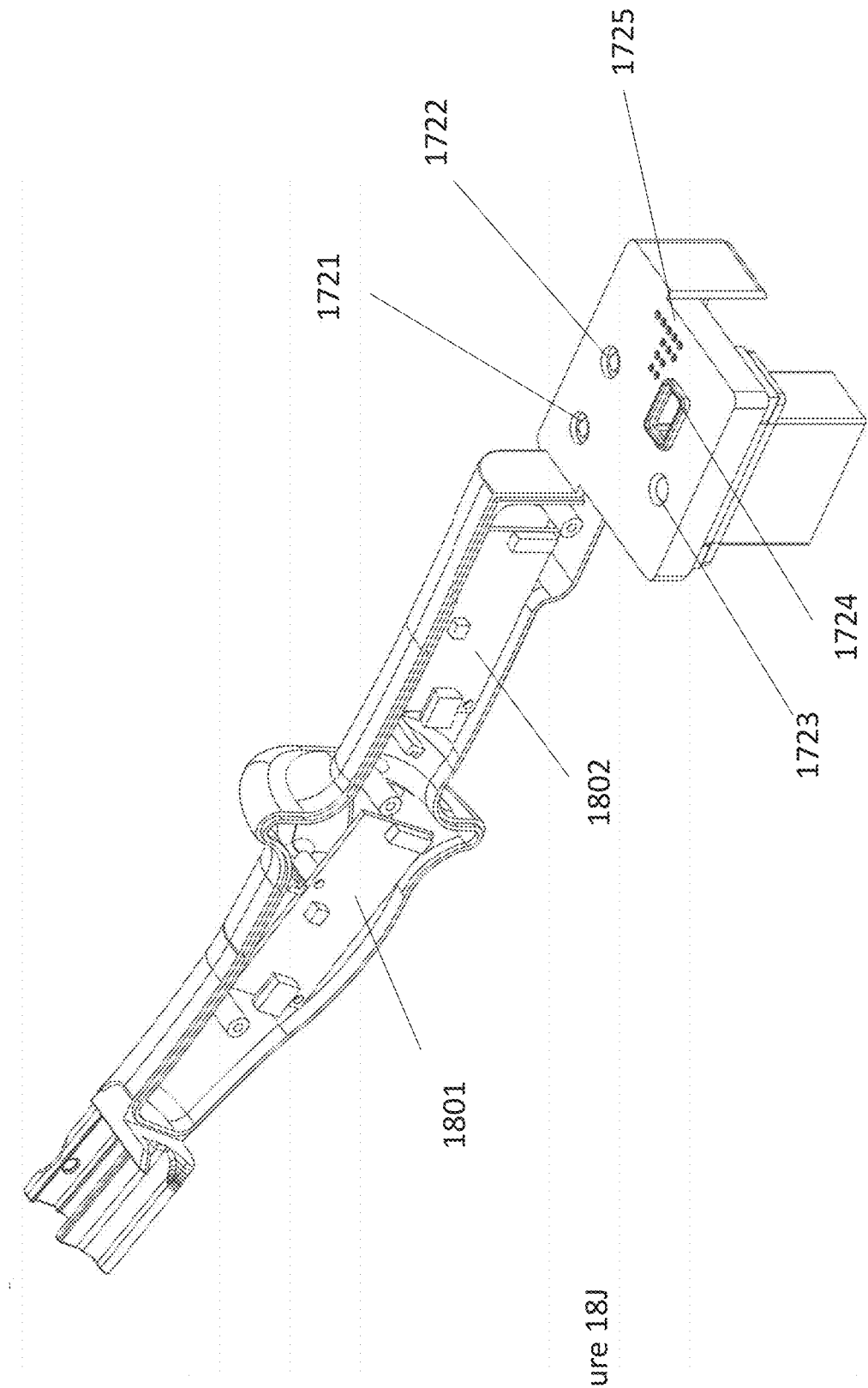

FIGS. 18G-18J illustrate housing 1710, with at least one housing body component removed (e.g., half of a shell, for example) to illustrate exemplary internal housing components that may be disposed in any of the housings herein. FIG. 18G is a side view of housing 1710. 18H is a bottom perspective view of housing 1710. FIG. 18I is a bottom view of housing 1710. FIG. 18J is a top perspective view of housing 1710. In this example, housing includes camera control unit 1801, which may be a camera control unit for any of the first image sensors herein, and which may be adapted to translate a raw camera signal from the first image sensor into USB, for example. Housing 1710 further includes second camera control unit 1802, which may be a camera control unit for any of the second image sensors herein, and which may be adapted to translate a raw camera signal from the second image sensor into USB, for example. Location 1803 presents an exemplary location for an exemplary USB hub.

FIG. 18G also illustrates exemplary axial drive motor 1804 (which may be referred to herein as an axial actuation mechanism), which may comprise an axial drive servo, and which may be adapted to facilitate axial motion of the introducers herein, which is described in more detail elsewhere herein. For example, axial drive motor 1804 may cause rotation of mechanical interface 1723, which is described in more detail herein and shown in FIG. 18J. Axial drive motor 1804 is an example of an actuator as that term is used herein (and in this example is an example of an actuator that is disposed in the housing). FIG. 18H illustrates merely exemplary first and second deflection (or articulation) drive motors 1805 (which may be referred to herein as actuation mechanisms), which may comprise deflection servos, and which may be adapted to facilitate deflection of the introducer, which is described in more detail elsewhere herein (e.g., which may cause pullwires to be tensioned). For example, first and second deflection drive motors 1805 may cause rotation of mechanical interfaces 1721 and 1722, respectively, which are described in more detail herein and shown in FIG. 18J. First and second deflection (or articulation) drive motors 1805 are examples of actuators as that term is used herein (and in this example are an example of actuators that are disposed in the housing). FIG. 18I illustrate an exemplary location for a microcontroller.

FIGS. 19A-19K illustrate exemplary second elongate imaging members and exemplary features thereof. FIGS. 19A-19K are shown and described in the context of second imaging member 1740, but any suitable aspect of the second imaging member in FIGS. 19A-19K may be incorporated with any other second elongate imaging member herein, and vice versa. For example, FIG. 14A herein illustrates an exemplary system 1400, which may also be considered to be an integrated assembly as that term is used herein. System 1400 (or assembly 1400) in FIG. 14A includes an introducer assembly 1499 (which may also be considered to be any of the second imaging members herein), which includes an introducer housing 1490 (which may be considered to be any of the second imaging member housings herein) secured to moveable introducer 1450, wherein introducer housing 1490 is sized and configured to be releasably secured to handheld housing 1410 (which may be considered to be any of the housings herein), and wherein the introducer assembly 1499 may be disposable.

Figure 19A:
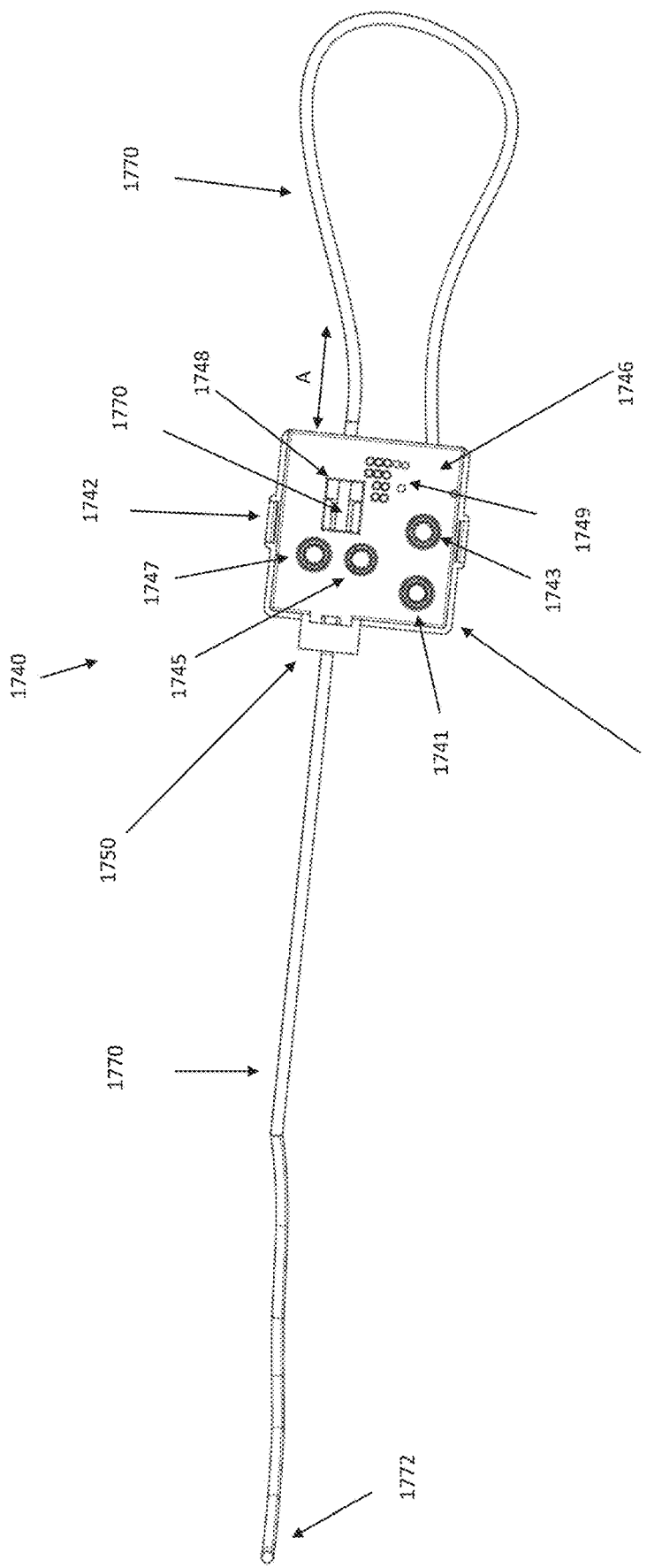
FIG. 19A illustrates a bottom view of an exemplary second imaging member, including an optional image sensor at a distal end region.

FIG. 19A is view of the bottom of second imaging member 1740, which includes housing 1744 and introducer 1770. In this example, introducer 1770 is secured to housing 1744 at an end (or an end region) of introducer 1770, and movable relative to housing 1744 along at section of the introducer 1770 distal to where it is secured to housing 1744. This is similar to introducer 1450 shown in FIGS. 14A-14D herein. Housing 1744 including a communication region 1746 that includes one or more communication elements that are adapted to communicate with the handle when the second imaging member is releasable coupled to the housing. The communication elements may optionally be positioned and configured to communicate mechanically, electrically, video and/or optically with the handle. The communication elements may be configured to communicate information (e.g., image data) and/or operably communicate with the handle to cause movement of the introducer in one or more directions, as is described in more detail herein.

In this exemplary embodiment, communication region 1746 of second imaging member 1740 includes mechanical interfaces 1741 and 1743 that are disposed relative to housing 1744 and configured to mechanically interface with mechanical interfaces 1721 and 1722 in the communication region 1720 of housing 1710 (see FIG. 18C). The mechanical interfaces may include, as an example only, a geared interaction with teeth, wherein rotation of mechanical interfaces 1721 and 1722 of the housing 1710 (e.g., in response to activation of a housing motor) causes rotation of mechanical interfaces 1741 and 1743, respectively. As described in more detail below, one or more tensioning elements (e.g., one or more pullwires) may be operatively coupled to mechanical interfaces 1741 and 1743 such that rotation of the interfaces 1741 and 1743 causes tensioning of one or more pullwires, which may cause deflection of the introducer.

In this example, communication region 1746 of second imaging member 1740 also includes mechanical interfaces 1747 that is disposed relative to housing 1744 and configured to mechanically interface with mechanical interface 1723 in the communication region 1720 of housing 1710 (see FIG. 18C). The mechanical interface may include, as an example only, a geared interaction with teeth, wherein rotation of mechanical interface 1723 of the housing 1710 (e.g., in response to activation of a housing motor) causes rotation of mechanical interface 1747. In this example, interface 1745 is configured to have a geared interaction with interface 1747 such that rotation of interface 1747 causes rotation of 1745 as well (see FIG. 19F). Introducer passes through housing 1744 and is disposed between rotatable mechanical interfaces 1747 and 1745 such that their rotation causes axial translation (distal or proximal) of introducer 1770, wherein FIG. 19A illustrates axial direction "A," which represents the axial movement of introducer 1770 relative to housing 1744. Additional details of communication region 1746 are described below.

Figure 19B:
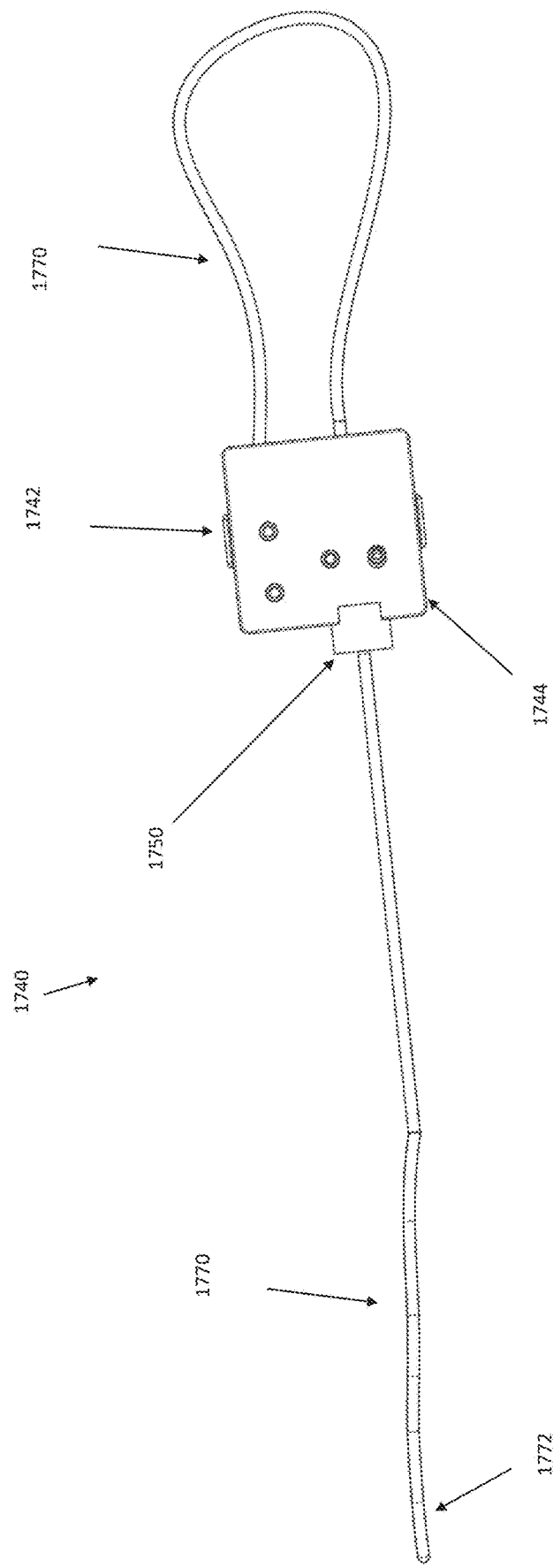
FIG. 19B illustrates a top view of an exemplary second imaging member.
Figure 19C:
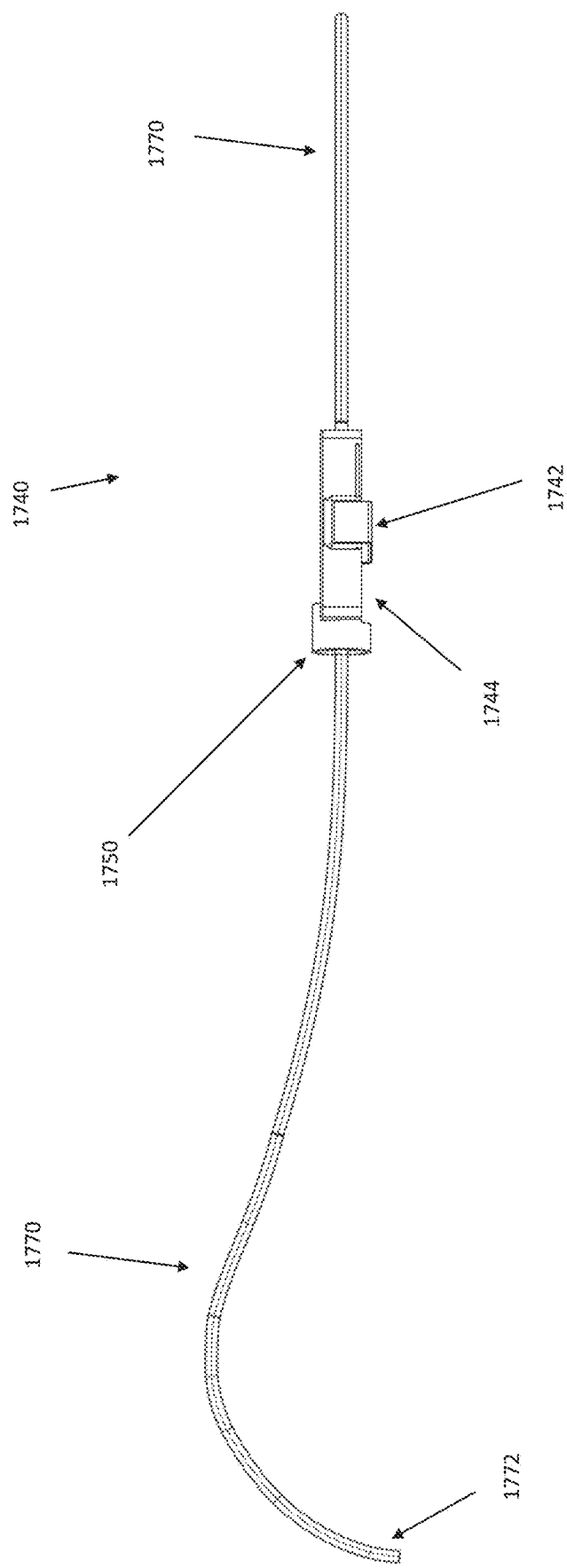
FIG. 19C illustrates a side view of an exemplary second imaging member.

FIG. 19B illustrates a top of the second imaging member 1740, including endotracheal tube coupler 1750. FIG. 19C illustrates a side of view of second imaging member 1740. FIG. 19C illustrates an introducer with a curved configuration. When one or more system or assembly components are descried herein as having a length, the length generally refers to the length along the component (e.g., from a first end or a first location of the component to a second end or a second location). For example, the introducer in FIG. 19C may have a length that extends from a first end secured to housing 1742 and a distal most end of the introducer, wherein the length of the introducer in this example can be measured from the first secured end to the second end along the length of the introducer itself, even if there is one or more curved regions.

Figure 19E:
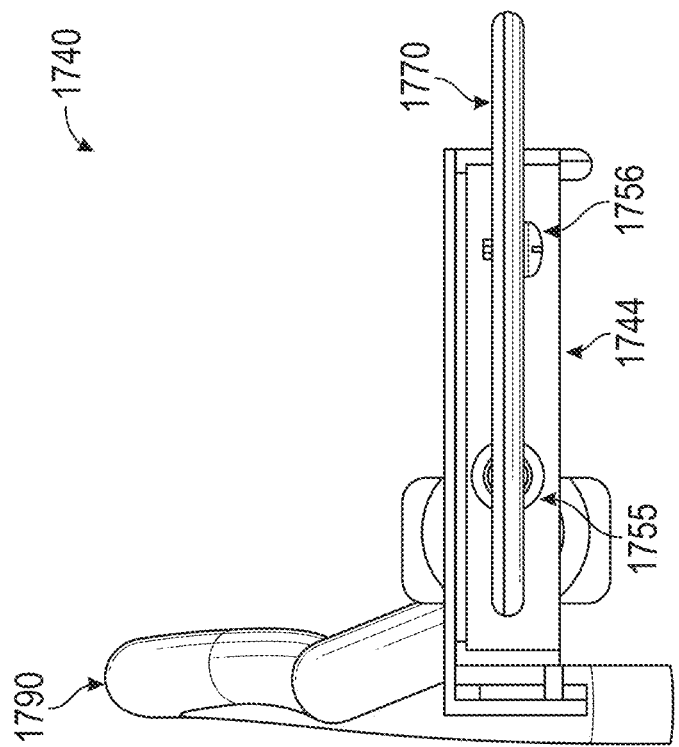
FIG. 19E illustrates a front, end view of a second imaging member coupled to an intubation tube.
Figure 19D:
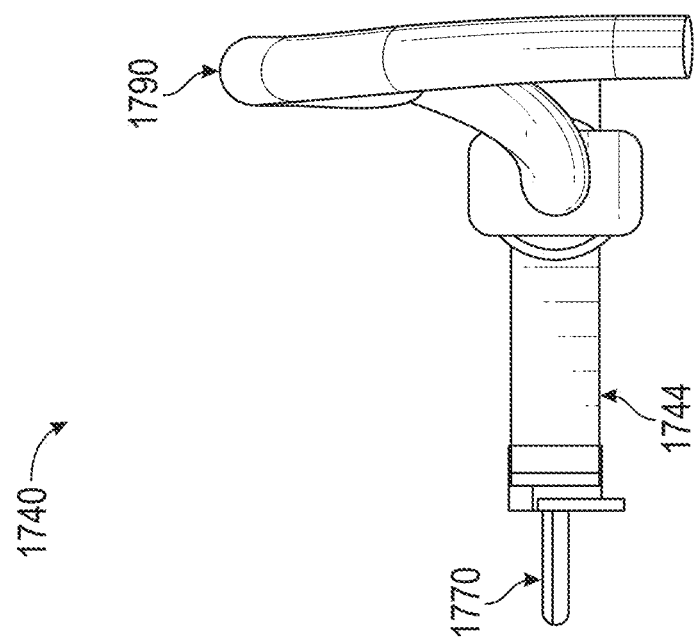
FIG. 19D illustrates a back, end view of a second imaging member coupled to an intubation tube.

FIGS. 19D and 19E illustrate end views of second imaging member 1740.

Figure 19F:
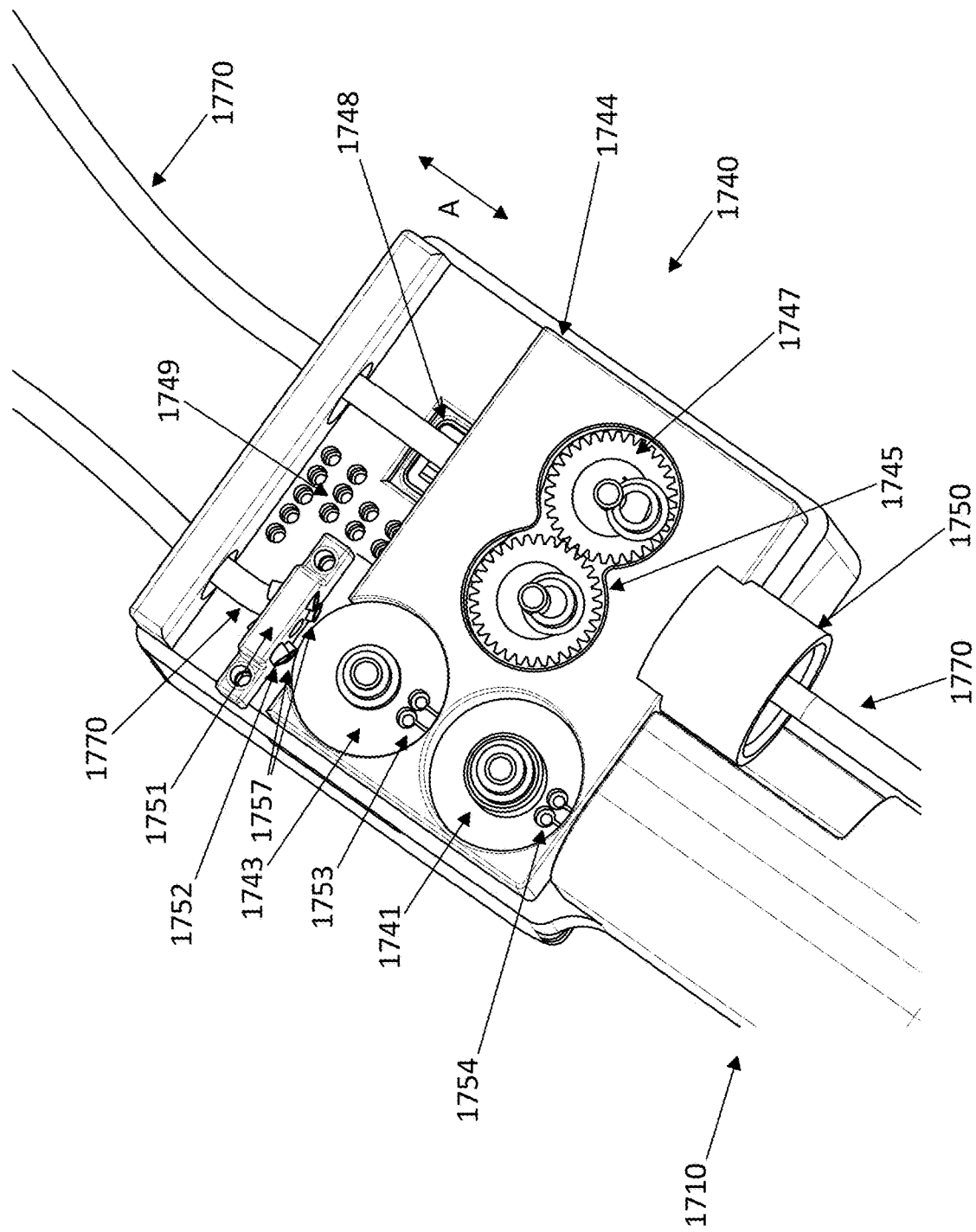
FIG. 19F illustrates a top view of an exemplary second imaging member with a top face removed to show internal components.

FIG. 19F illustrate a view of the top of exemplary second imaging member 1740 with a top surface of layer of the housing removed to show exemplary internal components in the communication region 1746 of housing 1744. The view in FIG. 19F is the same view as in FIG. 19B, but with a portion of the housing removed to illustrate components internal to housing 1744. FIG. 19A illustrates a view of the bottom of second imaging member 1740. FIG. 19F illustrates an exemplary geared interface between rotatable interfaces 1745 and 1747, which are described above. Mechanical interface 1747 may be in interfaced with rotating interface 1723 in the handle such that rotation of rotating interface 1723 (e.g., driven by a motor) causes rotation of mechanical interface 1747. The geared interface between interfaces 1745 and 1747 causes interface 1745 to rotate in the opposite direction to the rotation of interface 1747, which axially moves introducer 1770 that is disposed between interfaces 1745 and 1747. The geared relationship between interfaces 1745 and 1747 may amplify forces on the introducer and help prevent slipping during axial movement of the introducer.

In some embodiments, an added gear, similar to an idler gear, may be added to the handle, for example, in communication with rotating interface 1723 (driven by the motor) to actively drive both rotatable interfaces 1745 and 1747.

FIG. 19F also illustrates a plurality of electrical connectors 1749, which are arranged and configured in the housing to interface with electrical connectors 1725 in the handle, and which may communicate image data from the image sensor at the distal end of the introducer to the housing 1710, which is described in more detail herein.

FIG. 19F also illustrates window or opening 1748 aligned with and adjacent to a section of introducer 1770, as shown. The window 1748 is positioned to align with sensor 1724 (e.g., an optical sensor) in the housing such that the housing sensor can track the movement or position of the introducer as it moves axially "A." The introducer may have one or more markers on an outer surface thereof to facilitate position tracking or sensing by the housing sensor 1724. The housing sensor 1724 may communicate the sensed information to the processor (directly or indirectly) to track the axial movement and/or position of the introducer.

FIG. 19F also illustrates mechanical interfaces 1741 and 1743, which are positioned and configured to interact with mechanical interfaces 1721 and 1722 in housing 1710. In this example, mechanical interfaces 1741 and 1743 rotate in response to rotation of mechanical interfaces 1721 and 1722 in housing 1710, which in this example is used to cause deflection of a distal region or distal tip of the introducer in a plurality of directions (e.g., one or more of up, down, left, right, or a combination thereof). FIG. 19F illustrates a mere example of using first and second motors within housing 1710 to cause rotation of interface 1741 and 1743, respectively. In this example, interfaces 1741 and 1743 are each coupled to first and second pullwires, such that when they are rotated in a first direction, one of the pullwires is tensioned to cause deflection of the introducer distal tip, and when rotated in the opposite direction, a second pullwire may be tensioned to cause deflection in a different direction (e.g., 180 degrees relative to the first direction). In an example, rotation of interface 1741 can cause deflection of the introducer in a first plane (each direction 180 degrees relative to the other direction, for example, left and right), and rotation of interface 1743 can cause deflection of the introducer in a second plane transverse to the first plane (each direction 180 degrees relative to the other direction, for example, up and down). The interfaces 1741 and 1743 may be controlled separately, such as with different motors in the housing, both in response to robotic control of the introducer movement (either automatic or manual robotic control).

In the example of FIG. 19F, pull wires (e.g., exemplary and illustrative first and second pull wires 1757 are shown for clarity) may be attached to interfaces 1741 and 1743 at locations 1754 and 1753 respectively, using any of a variety of securing techniques or mechanisms. The pullwires extend from interfaces 1741 and 1743 through pull wire channels generally labeled 1752, and then extend into introducer 1770. The pull wires may extend through the introducer using existing pull wire routing techniques and approaches, and are secured in a distal region of the introducer to cause the defection of the distal tip of the introducer.

In any alternative, a housing motor may be in operable communication with only one pull wire. For example, in a variation to that shown in FIGS. 19F, the housing 1710 may include four motors therein, each causing an individual pull wire to be tensioned.

FIGS. 19G-19K illustrate exemplary second imaging member housings, and it is understood that any second imaging member housing herein may include any of the exemplary features of the exemplary housing 1744 shown in FIGS. 19G-19K, and vice versa. FIG. 19G is a perspective view of the bottom of housing 1744. FIG. 19H is a bottom view of housing 1744. FIG. 19I is a top perspective view of housing 1744. FIG. 19J is a front end of housing 1744, illustrating first and second windows 1755 and 1756 through which introducer 1770 extends. FIG. 19K illustrates a back end view of housing 1744, including endotracheal tube coupler 1750. As set forth herein, a first end of end region of the introducer may be secured within housing 1710, and in FIG. 19F a first end of introducer 1770 is secured to element 1751 within housing 1751. From element 1751, introducer 1770 extends through housing opening or window 1756 (see FIG. 19J) and out of housing. Introducer 1770 then forms a loop configuration as shown (e.g., FIGS. 17B, 17C, 17E, 17G, 19A, 19B, 19E), and then extends back into the housing through housing opening or window 1755 (see FIG. 19J). Introducer then extend through optional endotracheal coupler 1750 of housing 1744, as can be seen in FIG. 19F.

As shown, housing 1744, in this example, has a general rectangular configuration (and in this example it has a generally square configuration), with width and height that are both greater than a thickness measured in the top-to-bottom direction. The corresponding mating region of housing 1710 has a similar rectangular configuration, as shown in the unassembled view of FIG. 17B.

Second imaging member 1740 includes endotracheal tube coupler 1750 which in this example has a circular cross section and has a cylindrical configuration. As shown in FIG. 17A, endotracheal tube has a first end with a coupler region 1791 as shown that is dimensioned and sized to interface with endotracheal tube coupler 1750 on the housing 1744 of the second imaging member 1740. Endotracheal tube 1790 also has lumen that is sized to receive the introducer therein when the coupler region 1791 is interfaced with endotracheal tube coupler 1750 of housing 1744, such as is shown in FIG. 17C.

As shown in FIG. 17A, body 1711 of housing 1710 also includes a side endotracheal tube channel 1713 that is positioned and configured such that when cover 1780 is releasably secured to housing 1710, channel 1713 of housing 1710 and the channel 1784 in the cover form a continuous channel for the endotracheal tube, as shown in FIG. 17D. The term continuous in this context includes some minimal axial gap (e.g., 0.01 cm-2 cm) between the two channels when cover 1780 is coupled to housing 1710, as long as endotracheal tube 1790 can be interfaced with housing channel 1713 and cover channel 1784. Both channels 1713 and 1784 are open on one side to allow the endotracheal tube to be removed from the channels by laterally or horizontally removing them therefrom.

The housings (e.g., housing 1710) or integrated handheld assemblies herein may include one or more image processors, while is some embodiments data may be communicated to a component not integrated into the assembly where image processing occurs, such as an external computer and/or display of the system, for example. Any type of connection may be used for data transfer, such as a USB interface.

Any of the assemblies may also include one or more microcontrollers, which may optionally be disposed in the housing (e.g., housing 1710). Any of the assemblies may also include one or more motor interfaces (e.g., part of the robotic control of the introducer movement), which may optionally be disposed in the housing (e.g., housing 1710). Any of the assemblies herein may also include an electronics control board, which may provide power to the one or more motors optionally disposed in the housing during the robotically movement of the introducer.

As shown in FIG. 17D (in combination with FIG. 17C), the first and second image sensors (e.g., video cameras) are maintained an axial distance relative to one another when the assembly is assembled. In FIG. 17D the axial locations of the first and second image sensors is labeled L, and in this embodiment the images sensors are within 3 cm from each other axially, and may optionally be axially aligned. The image sensors are also at a horizontal distance "H" (see FIG. 17C) not greater than 2 cm from other. When assembled, the first and second image sensors are thus maintained at a relatively close distance (both axially and horizontally) to each other, the advantages of which are described herein. Assembly 1702 is thus an example of an integrated and handheld dual-video tracheal intubation assembly, wherein the assembly is configured such that when the first imaging member is coupled to the housing, when the second imaging member is coupled to the housing, when the cover is releasably coupled to the housing, and when the endotracheal tube is releasably coupled to assembly, the assembly maintains the first image sensor at a distance from the second image sensor prior to actuation of the actuator, an example of which is shown in FIGS. 17C and 17D. In this example, the lengths and configurations of all of the endotracheal tube, the introducer, the cover, the flexible body 1732 of the first imaging member 1730, and the body 1711 of housing 1710 (together and individually) allow and cause the first and second image sensors to be at the maintained distance from one another, as well as contribute to the overall small profile and footprint of the assembly, which allows the assemblies to be held and moved and operated by a single hand of an operator.

Assembly 1702 is an example of an assembly that can be used in a tracheal intubation. One of the advantages is that the first and second image sensors, when the assembly is assembled, are maintained at a relatively close axial distance (e.g., not greater than 3 cm, and optionally axially aligned). When in use, the introducer generally needs to be able to be robotically axially moved approximately at 3-5 cm to move it to or towards the glottic opening. The assembly is also adapted to be able to axially move the introducer through the glottic opening and in the trachea. The assemblies herein are thus able to robotically cause axially movement of the introducer and second image sensor that is at least 3 cm relative to the first image sensor, which is maintained in the upper airway when in use for tracheal intubation.

The assemblies herein may include a distal movement limiter that is configured to limit distal movement of the introducer relative to an initial position and relative to a first image sensor. For example, assembly 1720 includes a distal movement limiter that is configured to limit distal movement of introducer 1770 relative to an initial position (e.g., as shown in FIGS. 17C and 17D) and relative to a first image sensor of the first imaging member 1730. In this example, a first end of introducer is secured to housing 1744, as shown in FIG. 19F, while the introducer is allowed to be robotically moved axially with the axial movement mechanism inside housing 1744 (e.g., including mechanical interfaces 1745 and 1747). By securing a first end of introducer 1770, there is a limit on how far introducer 1770 may be advanced distally in this example. The length of the introducer outside of housing 1744 between openings 1755 and 1756 in housing 1744 can also influence how far distally the introducer may be advanced, and may thus be considered part of or influence the distal movement limiter. For example, if the length of introducer 1770 that is outside housing 1744 and between openings 1755 and 1756 is very short, the distal movement limiter will prevent much distal travel of the introducer relative to housing 1744.

Figure 20:
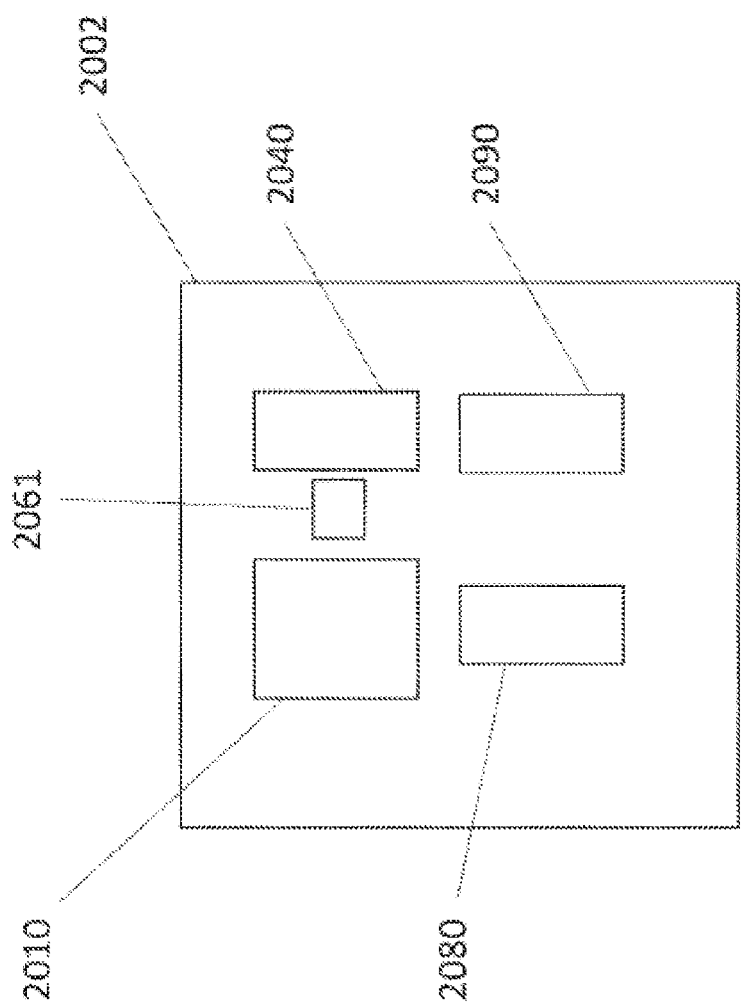
FIG. 20 schematically shows an exemplary integrated and handheld dual-video assembly.

FIG. 20 illustrates schematically an exemplary integrated and handheld dual-video assembly 2002, which may incorporate any and all aspects of assembly 1702 and assembly 1702'. Assembly 2002 includes housing 2010, which may incorporate any and all aspects of any of the housings herein (e.g., housing 1710). Assembly 2002 includes cover 2080, which may incorporate any and all aspects of any of the covers herein (e.g., cover 1780). Assembly 2002 includes optionally disposable second imaging member 2040, which may incorporate any and all aspects of any second imaging member herein (e.g. second imaging member 1740). Assembly 2002 includes endotracheal tube 2090, which may incorporate any and all aspects of any of the ETT's herein (e.g., endotracheal tube 1790). Assembly 2002 includes one or more actuators 2061, which may incorporate any and all aspects of any one of the actuators herein (e.g., one or more actuators 1761 (actuators may be within housing 2010 and/or within second imaging member 2040, for example)).

Any of the assemblies herein (e.g., 1702, 1702') may be generalized as shown in the schematic of FIG. 20.

It is understood that any description including features or methods of use related to assembly 1702 may be integrated with assembly 1702', and vice versa.

Figure 21:
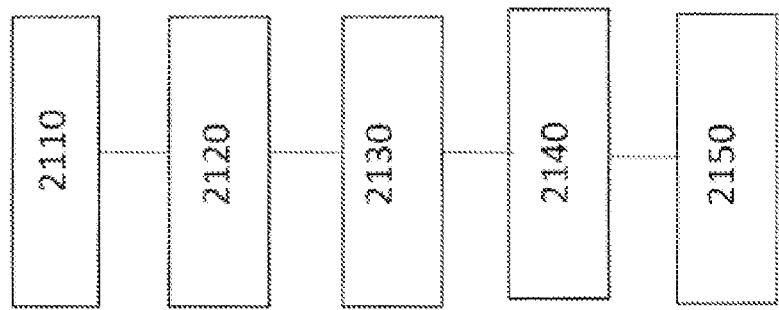
FIG. 21 illustrates an exemplary method of using any of the integrated handheld assemblies. herein.

FIG. 21 illustrates an exemplary method of using any of the assemblies herein. In the method shown, an assembled assembly (e.g., assembly 1702) is positioned within an upper airway of a patient (e.g., such as shown in FIG. 15) at step 2110. The method may include causing a processor of a system to receive a signal indicative of image data from a first image sensor (e.g., a video camera) of the assembly at step 2120. The method may include, at step, 2130, processing the signal indicative of the data from the first image sensor. The method may include, at step 2140, initiating automated or manual robotically controlled movement of an introducer of the assembly away from a first image source of the assembly and towards at least one upper airway anatomical landmark in response to the processing step while maintaining the first image sensor in the upper airway. The method may also include, at step 2150, causing the introducer to be moved within the endotracheal tube and advanced through and past the glottic opening and into a trachea while at least a portion of a cover of the assembly and the first image sensor remain in the upper airway and while the first image sensor receives video data from the first image sensor during automated movement of the introducer. Any additional method steps may be incorporated into the exemplary method shown in FIG. 21.

Any of the second elongate imaging members (e.g., 1740) may also be referred to herein as a cartridge, in that the cartridge may be releasably secured to the housing (e.g., housing 1710).

In variations to some embodiments herein, the systems are adapted such that a remote operator can remotely control the robotically controlled movement of the introducers herein. For example, a first operator would be with the patient and places the assembly into the patient's upper airway, for example. The first operator activate operation of the first and/or second image sensors. The image data can be communicated (e.g., wireless communication) to the remote location, where a second operator can control the introducer remotely (e.g. using a workstation). The second operator can have a display that shows video data from the first and/or second image sensors. This type of remote control arrangement can provide the advantages of the integrated dual-video intubation assemblies herein, with the exception that the first operator in these examples would be directly handling the assembly.

Any of the processors herein may have stored thereon any number of computer executable methods (e.g., software, algorithms) that may be adapted, alone or in combination, to receive one or more inputs that may be indicative of image or video data from one or more image sensors herein, and determine or contribute to determining a pathway in any number of directions for an introducer, which may include causing the movement of the introducer such that it is moved to or towards one or more anatomical landmarks. This type of determining or planning may be referred to herein as navigating or part of a navigation process.

It is understood that any feature, component, or method step described herein in one example may be incorporated into any other suitable example herein unless the description indicates to the contrary. For example, any feature or method of use in any embodiment or aspect herein may be included with or incorporated into any other suitable embodiment or aspect herein.

The foregoing description, for purposes of explanation, used specific nomenclature to provide a thorough understanding of the inventions herein. However, it will be apparent to one skilled in the art that specific details may not be required in order to practice one or more of the inventions herein. Thus, the foregoing descriptions of specific embodiments of the inventions herein are presented for purposes of illustration and description.

Even if not specifically indicated, one or more techniques or methods described in this disclosure may optionally be implemented, at least in part, in hardware, software, firmware or any combination thereof. For example, various aspects of the techniques or components may be implemented within one or more processors, including one or more microprocessors, digital signal processors (DSPs), application specific integrated circuits (ASICs), field programmable gate arrays (FPGAs), programmable logic circuitry, or the like, either alone or in any suitable combination. The term "processor" or "processing circuitry" may generally refer to any of the foregoing circuitry, alone or in combination with other circuitry, or any other equivalent circuitry. Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. When implemented in software, the functionality ascribed to the systems, devices and techniques described this disclosure may optionally be embodied as instructions on a computer-readable medium such as random access memory (RAM), read only memory (ROM), non-volatile RAM (NVRAM), electrically erasable programmable ROM (EEPROM), Flash memory, and the like, for example. The instructions (e.g., methods) may be executed by a processor to support one or more aspects of the functionality described in this disclosure.

ADDITIONAL EXAMPLES

A first additional example is an integrated device for robotically assisting with airway management (e.g., intubation) of a patient, comprising: a handheld housing; a laryngoscope coupled to the housing and comprising a first image sensor; an actuating member movable within the housing; an endoscope extending from the actuating member, wherein the endoscope comprises a second image sensor and is configured to removably couple to an intubation tube; and at least one actuator in the housing configured to automatically guide the endoscope via the actuating member, based at least in part on one or more images from at least one of the first image sensor and the second image sensor.

In this example, the device may further comprise a cover coupled to the housing, wherein the cover comprises a first channel configured to receive the laryngoscope and a second channel configured to receive at least a portion of the endoscope. The cover may comprise a first portion comprising the first channel and a second portion comprising the second channel, wherein the first and second portions are removably coupled. The cover may comprise a displacement member configured to retract a tongue of a patient during an intubation procedure. A displacement member may be angled or curved. A cover may be configured to be advanced over a tongue of the patient both in or near the vallecular of the patient, and under an epiglottis of the patient. A distal end of the first channel and a distal end of the second channel may be adjacent and substantially parallel. A cover may be removably coupled to the housing.

In this example, at least one of the first image sensor and the second image sensor may provide a viewing angle of at least 40 degrees in both axial and horizontal planes. A viewing angle may be between about 40 degrees and about 180 degrees in both axial and horizontal planes. A viewing angle may be between about 40 degrees and about 360 degrees in both axial and horizontal planes.

This example may further comprise a video monitor configured to display at least one image from the first image sensor, the second image sensor, or both. A video monitor may be configured to display images from the first image sensor and the second image sensor in a split-screen or picture-in-picture arrangement.

In this example, an actuating member may be axially extendable. An actuating member may comprise one or more interlocking rings or one or more spiral elements.

In this example, an actuating member may be movable within a guide. At least a portion of a guide may be in the housing. At least a portion of the guide may be in a video monitor coupled to the housing. At least a portion of the guide may be curved. The guide may be straight. The at least one actuator may be configured to automatically guide the actuating member within the guide. The actuating member may be manually movable within the guide. This example may further comprise a user input device aligned with the guide, the user input device coupled to the actuating member so as to enable manual control of movement of the actuating member within the guide. The actuating member may be longitudinally translatable within the guide, to thereby longitudinally advance and retreat the endoscope. The at least one actuator is configured to automatically articulate a distal end of the endoscope. The at least one actuator may be configured to articulate a distal end of the endoscope in a first plane.

This example may further comprise at least one processor configured to process images acquired by at least one of the first image sensor or second image sensor. The at least one processor may be configured to process the one or more images by identifying at least one recognizable anatomical feature. The at least one processor may be configured to identify the at least one anatomical feature by applying a trained machine learning algorithm to the one or more images. The at least one processor may be configured to control the at least one actuator to automatically guide the endoscope towards the at least one anatomical feature. The at least one processor may be configured to initiate the control of the at least one actuator based on one or more images from a laryngoscope. The at least one processor may be configured to automatically guide the endoscope towards the at least one anatomical feature based on one or more images from the laryngoscope, one or more images from the endoscope, or both. The at least one processor may be configured to initiate the control of the at least one actuator based on one or more images from the endoscope.

In this example, the endoscope may be removably coupled to the actuating member.

In this example, the actuating member may be reusable and the endoscope may be disposable.

In this example, the endoscope may be integrally formed with the actuating member.

In this example, a distal end of the actuating member may be axially aligned with a proximal end of the endoscope.

In this example, the endoscope comprises a flexible member, but the endoscope may comprise a rigid stylet having a deflectable distal end.

In this example, the device is operable by a single user.

In this example, the actuating member may be between about 10 cm and about 40 cm long.

In this example, the endoscope may be between about 20 cm and about 30 cm long.

In this example, the endoscope may be between about 20 cm and about 60 cm long.

In this example, the device may be configured for use with an adult patient or a pediatric patient.

In this example, the intubation tube may be an endotracheal tube.

In this example, the device may be configured for assisting orotracheal intubation, or the device may configured for assisting nasotracheal intubation.

A second additional example is an integrated robotic device adapted for airway management, comprising: a handheld housing; a laryngoscope coupled to the housing and comprising a first image sensor; an actuating member movable within the housing and coupleable to an introducer comprising a second image sensor; and at least one actuator in the housing configured to automatically move the actuating member, based at least in part on one or more images from at least one of the first image sensor and the second image sensor.

A third additional example is an integrated robotic device adapted for airway management, comprising: a handheld housing; an actuating member movable within the housing and coupleable to an introducer comprising an image sensor; and at least one actuator in the housing configured to automatically move the actuating member, based at least in part on one or more images from the image sensor.

In some embodiments, the navigation of the introducer scope (second imaging member) may be aided by the visualization through the laryngoscope (first image sensor) for navigation of the introducer scope either manually, or automatically by a processor. For example, the outer shaft of the introducer scope may include one or more markings or indicators, wherein the one or more markings or indicators on the outer shaft of the introducer scope may be visible to the laryngoscope first image sensor during the procedure. These indicators may indicate the distance from the distal tip of the introducer scope, and therefore indicate how far into the anatomy (or beyond the laryngoscope) the introducer scope has advanced. This may be useful to prevent the introducer scope from being advanced too far, or not far enough, and may prevent misplacement of the introducer scope and ultimately the ETT.

In some embodiments, the indicators on the introducer scope may indicate the flexible or deflectable zone of the introducer scope (e.g., the one or more indicators may be disposed on the shaft and may be indicative of the location and/or position of the flexible or deflectable zone of the introducer scope).

In some embodiments, the one or more indicators may include one or more of bands, or dots, or markings, which may be black or may be of color. Different colors, thicknesses, symbols, numbers may be incorporated into the indicators to help distinguish different segments or areas along the length of the introducer scope. The one or more indicators herein may include a combination of different types of indicators on the introducer scope shaft, such as (for example without limitation) one or more of the indicators being colors, while one or more other indicators may be symbols.

In some embodiments, lights may be used as indicators.

The indicators may span 360 degrees around the introducer scope shaft, or may span only a portion of the circumference. For example only, an indicator may span or extend 360 degrees around the introducer scope shaft, while in other examples an indicator may span or extend 180 degrees, or 90 degrees, around the introducer scope shaft.

The outer shaft of the introducer scope may additionally or alternatively be bright, or reflective, to help its visualization during a procedure. For example only, an introducer scope shaft may comprise one or more reflective materials that help reflect light to at least some extent during a procedure.

Figure 34:
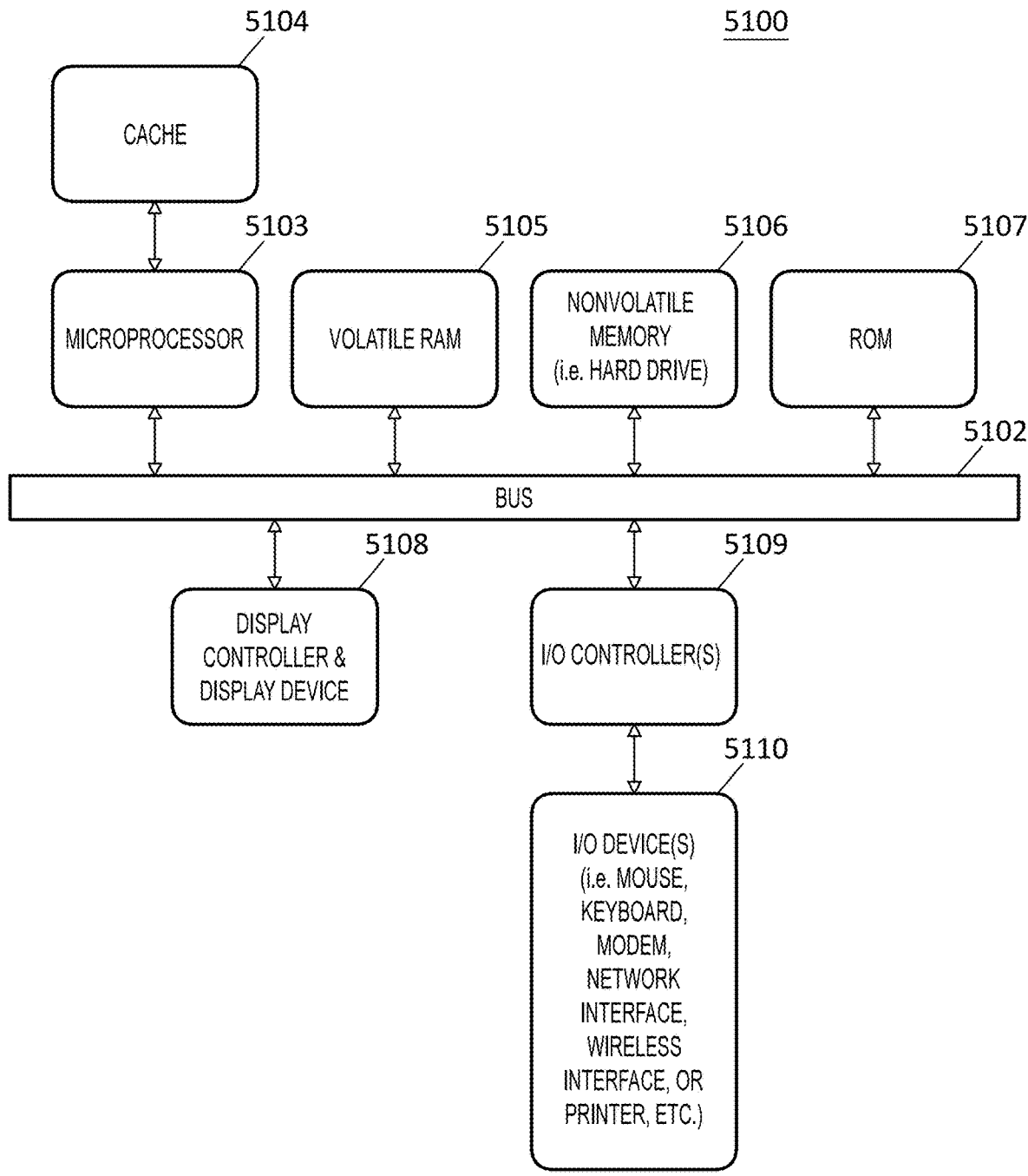
FIG. 34 is a block diagram of an exemplary data processing system.

FIG. 34 is a block diagram of an exemplary data processing system, which may be used with any embodiments of any of the inventions or embodiments set forth herein. Note that while FIG. 34 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 34, exemplary computer system 5100, which is a form of a data processing system, includes a bus or interconnect 5102 which is coupled to one or more microprocessors 5103 and a ROM 5107, a volatile RAM 5105, and a non-volatile memory 5106. The microprocessor 5103 is coupled to cache memory 5104. The bus 5102 interconnects these various components together and also interconnects these components 5103, 5107, 5105, and 5106 to a display controller and display device 5108, as well as to input/output (I/O) devices 5110, which may be mice, keyboards, modems, network interfaces, printers, and other devices which are well-known in the art.

Typically, the input/output devices 5110 are coupled to the system through input/output controllers 5109. The volatile RAM 5105 is typically implemented as dynamic RAM (DRAM) which requires power continuously in order to refresh or maintain the data in the memory. The non-volatile memory 5106 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 34 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 5102 may include one or more buses connected to each other through various bridges, controllers, and/or adapters, as is well-known in the art. In one embodiment, the I/O controller 5109 includes a USB (Universal Serial Bus) adapter for controlling USB peripherals. Alternatively, I/O controller 5109 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology. Wireless communication protocols may include Wi-Fi, Bluetooth, ZigBee, near-field, cellular and other protocols.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures herein can be implemented using code (e.g., computer executable methods, algorithms) and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Figure 22:
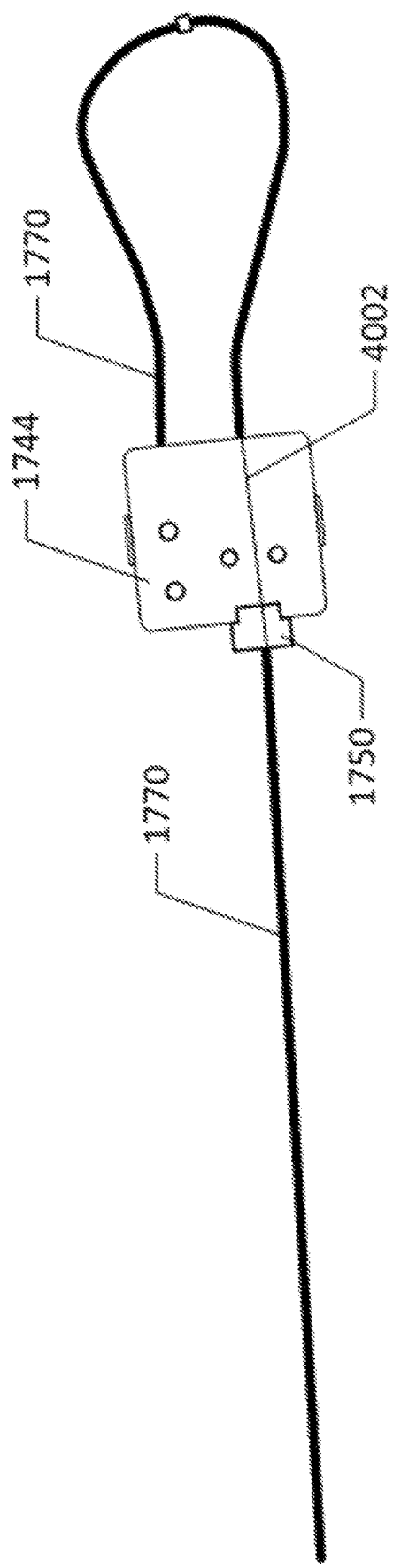
FIG. 22 shows an embodiment that is "resposable", meaning it can be sterilized and reused for a limited number of cases.

FIG. 22 shows an embodiment that is "resposable", meaning it can be sterilized and reused for a limited number of cases. In this embodiment, introducer scope 1770 may be fully or partially removed from housing 1744. For example, housing 1744 may have an opening, such as door opening 4002. This opening may be opened to expose introducer scope 1770 so that the introducer scope may be removed and either cleaned and/or sterilized or replaced with a sterile introducer scope, and the interior of housing 1744 may be cleaned and/or sterilized. The door, or opening 4002, may be only in housing 1744 or may be in the housing and coupler 1750. Alternatively, coupler 1750 may be removable and able to be cleaned/sterilized or replaced for the next use.

In some embodiments, the interior of housing 1744 may include a disposable sheath, which separates the introducer scope from the mechanical interfaces, such as mechanical interfaces 1745 and 1747 disclosed herein.

Some embodiments include a cleaning tool which can be used to clean and/or sterilize the inside interfaces of housing 1744. This tool may comprise an elongated cleaning tool which is drawn through the housing using the interior motors driving the mechanical interfaces, or drawn through the housing manually or otherwise.

In some embodiments, the mechanical interfaces, or gears, are disposable, and replaceable with sterile components. Any other components in contact with the scope may also be disposable. Alternatively, these components, including mechanical interfaces 1745 and 1747 may be able to be cleaned and/or sterilized.

One aspect of this disclosure is related to medical devices and systems that include a robotically controllable medical device (e.g., controllable endoscope, medical tool, surgical tool, articulatable catheter, etc.) and a user actuatable disposable controller that is adapted to be attached/detached or coupled/uncoupled from the robotically controllable medical device (directly or indirectly), and wherein the user actuatable controller may be adapted to be disposable (non-reusable) while one or more portions of the robotically controllable medical device may be reusable. An exemplary and non-limiting benefit of such systems is that more expensive components of a system can be reused, optionally without re-sterilization, while less expensive components that a user interacts with (e.g. physically contacts) to control the more expensive robotically controllable medical device component(s) can be discarded (not reused) after the medical procedure, and replaced with new sterile user-controllable components.

It is understood that the re-usable "controllable" part(s) of systems as described herein are not limited to controllable parts that move mechanically (e.g., articulating shafts, movable working distal ends of tools, etc.). For example, a reusable controllable medical device may refer to reusable electronics, such as in the example shown in FIG. 33.

A non-limiting exemplary implementation of this aspect is in the field of tracheal intubation, wherein a robotically controllable ETT introducer and/or introducer actuators (e.g., motor(s)) can be reused with a replaceable user actuatable controller, examples of which are provided herein. In some embodiments, the replaceable user actuatable controller includes an integrated intubation blade. Any and all of the disclosure above (including in the figures) may be optionally incorporated by reference into the embodiments herein that include disposable user actuatable controllers and reusable robotically controllable medical devices and/or medical device actuators.

In some intubation embodiments, one or more user interface devices, or control members (i.e. joystick, wheel, slider, button, voice-activated controller, or other similarly actuatable member), which the user controls (which may include physical contact, or non-contact such as a voice-activated controller (e.g., microphone)) and actuates to control the articulation and/or the advancement/retraction of the introducer (scope) may be part of a reusable controller that is fully or partially disposable or non-reusable. For example only, the control member(s) may be incorporated into a disposable blade of an intubation system. The one or more control members may be incorporated into an extension, either rigid or flexible, of the blade (e.g., wherein the blade and extension are integrated, and may optionally be unitary (unitary meaning formed of the same material such that they are not two coupled and integrated together)), such that the blade extension covers or surrounds at least a portion of a reusable body or housing (which may be referred to herein as an "introducer assembly") of the system when the reusable housing is disposed at least partially within the disposable blade. The extension of the blade is generally sized and configured to be handheld, which is described in more detail elsewhere herein. The introducer assembly of the system may be re-usable and include one or more introducer actuators such as motor(s) and/or other controls to cause and control the robotic articulation and/or the advancement/retraction of the introducer (which is considered part of the introducer assembly, even if the introducer can be uncoupled from the reusable housing). Exemplary introducer actuators (e.g., motors, etc.) are described elsewhere herein.

Figure 26:
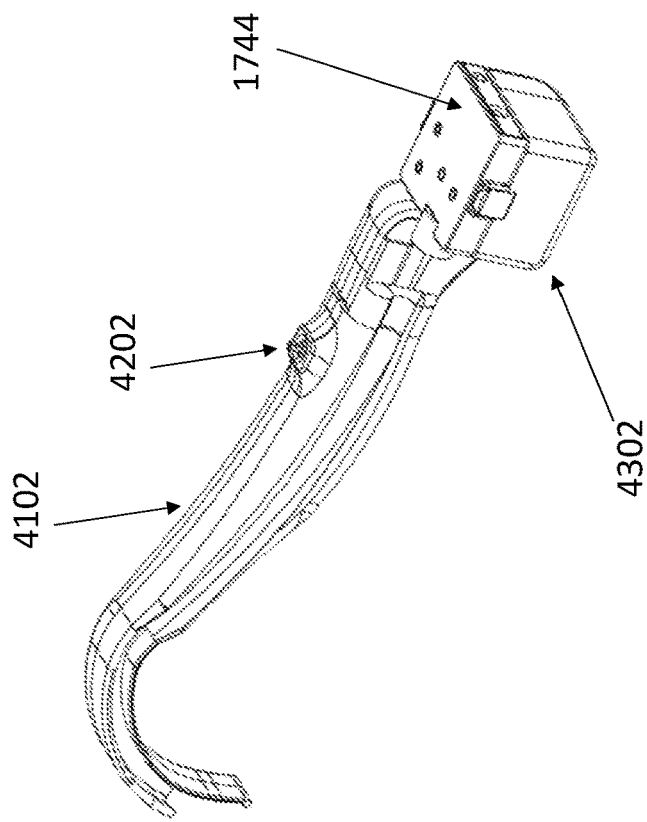
FIG. 26 shows the blade of FIG. 24 in place over the reusable introducer assembly housing of FIG. 25, and also illustrates an exemplary introducer housing coupled to the reusable housing in FIG. 25 (introducer not shown for clarity).
Figure 25:
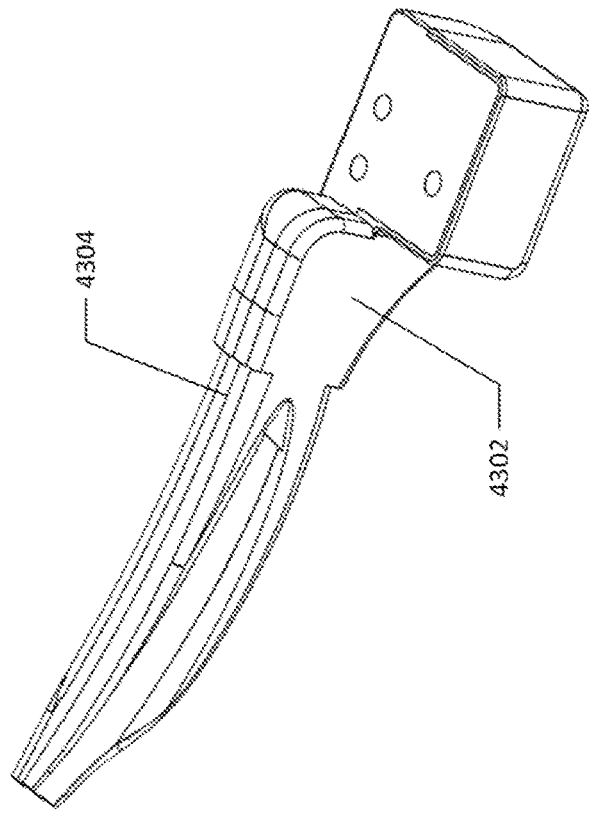
FIG. 25 shows an exemplary housing (optionally part of an introducer assembly) that may be re-usable.

Disposable blades herein may include a portion that includes one or more control members (such as a joystick) that control motor(s) and/or other introducer actuators within the reusable housing or body via a control member interface with one or more control member interface elements that are part of the reusable housing or body. The control member interface may be disposable and sterile on the outside, which the user contacts, and may be in in operational communication with the control member interface element in the re-usable housing on the inside. The user control member can be sealed off from the inner housing via a sterile barrier. In this way, the control member interface element remains sterile during use (not contaminated), and the reusable housing, which may include a motor(s) and/or other introducer controllers can be re-usable, without a need to be sterilized. It is understood that in this context, the reusable housing may include or be similar to any of the "housings" herein (such as housing 1710) and any of the "second imaging members" herein, such as second elongate imaging member 1740. It is thus understood that the reusable introducer assemblies in this context may include an introducer (such as introducer 1770 that is part of second imaging member 1740) that is detachable from a reusable housing, examples of which are described in more detail herein. For example, FIG. 26 illustrates a portion of a secondary imaging member (introducer shaft not shown for clarity), such as housing 1744, that is releasably coupled to the reusable housing that is shown in FIG. 25. It is thus understood that FIGS. 25 and 26 may both be considered to illustrate an "introducer assembly" herein, even when a detachable introducer is not secured to the housing that includes one or more actuators inside (e.g., motor). It is also understood that FIG. 25 illustrates an exemplary "reusable housing," which optionally includes one or more control member interface elements and at least one EET introducer actuator (e.g., motor).

Figure 23:
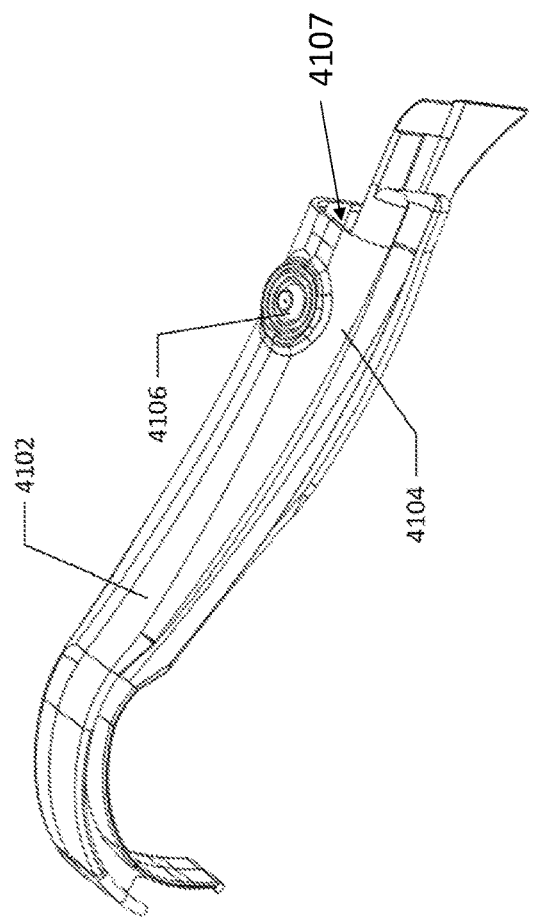
FIG. 23 shows an embodiment of an exemplary disposable controller (in this example a disposable blade), which includes an extension that comprises a control member, such as a magnet.

FIG. 23 shows an exemplary embodiment of a disposable controller, which in this example includes a disposable blade, and which includes an extended area, or extension, which incorporates at least one control member, in this example a magnet, which is sensed by a hall sensor that is in the reusable introducer assembly. In any of the embodiments herein, a blade and an extension can be integrated, as shown, and are optionally unitarily formed, or formed from the same material (not two components coupled together). The disposable controller shown in FIG. 23 includes disposable blade 4102, which includes a distal region (which may have a curved configuration as shown) sized and configured to be positioned in a mouth of the subject, blade extension 4104 that extends away from the distal region, wherein the disposable controller further include a control member 4106 that in this example includes a magnet, whose movement (when actuated by a user) is adapted to be sensed by a hall sensor in a reusable introducer assembly or reusable housing. The hall sensor (or other type of sensor) is also in operational communication with one or more introducer actuators (e.g., a motor(s)), which thus facilitates the robotic control of the introducer in response to user actuation of the disposable control member. In this example, the control member 4106 is integrated into extension 4104, and includes a hall sensor magnet that is incorporated within a flexible and moveable member, which may comprise a flexible material such as silicone (or other appropriate material), which allows the user to move the magnet by moving the flexible material. Movement of the magnet is sensed by a hall sensor in the introducer assembly housing, which is in proximity to and below the magnet. While this example includes a hall sensor, the sensor/mechanism (between the disposable control member and the reusable control member interface element) may be any type of suitable sensor that is adapted to sense motion, proximity, positioning, speed, acceleration, current, etc.

In any of the examples herein related to an intubation controller, the extension or body may be sized and configured to be held in a hand of an operator, and the controller may be disposed to be manually controllable by one or more fingers while the extension is grasped or gripped by a hand.

Blade 4102 also includes a cavity 4107 therein, which is sized and configured to receive therein at least a portion of an introducer assembly, such as a distal region of housing 4302 shown in FIG. 25. In this example, cavity 4107 is generally elongate and extends along at least a portion of the length of the extension 4104.

Figure 24:
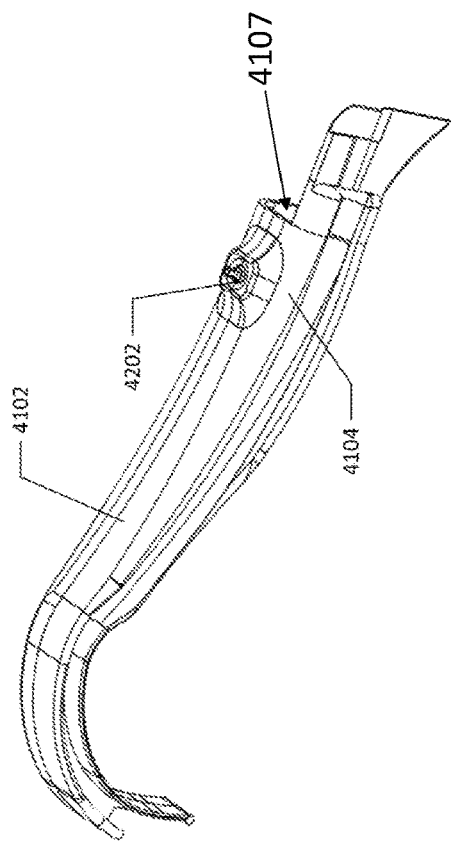
FIG. 24 shows an embodiment of a disposable blade that includes an extension comprising a control member that includes a joystick.

FIG. 24 shows another example of a disposable controller adapted for use with a robotically controllable medical device, which includes a disposable blade 4102 in this example, and which is similar to the blade in FIG. 23. Any relevant disclosure from FIG. 23 is incorporated by reference into the disclosure of FIG. 24. Blade 4102 includes a curved distal region that is adapted to be placed into the mouth, an extension 4104 that extends away from the curved distal region. Extension 4104 comprises control member 4202, which in this example includes a movable joystick, as shown. The joystick is incorporated or integrated within control member 4202, which is adapted to allow a user to move the joystick. Control member 4202 may further include a flexible material such as silicone. The joystick may be embedded in a sterile barrier or be completely below a flexible sterile barrier, additional details of which are described herein. Blade 4102 in FIG. 24 also includes a cavity 4107 therein, which is sized and configured to receive therein at least a portion of an introducer assembly housing or body, such as a distal region of housing 4302 that is shown in FIG. 25.

FIG. 25 shows at least a portion of a reusable housing (or body) of an exemplary introducer assembly, which is adapted to interface with a disposable controller, such as disposable blades herein. Reusable housing 4302 of the introducer assembly includes at least one control member interface element 4304 (shown generally) that is positioned and adapted in/on housing 4302 to be disposed in cavity 4107 of the disposable blade, and positioned relative to the at least control member to be in operable communication with the at least one control member in the blade, and responsive to the manual movement of the at least one control member when at least a portion of the housing is disposed in cavity 4107. Housing 4302 may include one or more actuators, such as motor(s) and/or other controllers to cause and control the robotic movement of the introducer, additional details of which are described herein. Housing or body 4302 further comprises control member interface element 4304, which includes one or more mechanisms that are adapted to interface with and be responsive to the control member of the blade, which may include a magnet or a joystick, for example only as shown in FIGS. 23 and 24. For example only, control member interface element 4304 may comprise a hall sensor responsive to movement of a magnet in the disposable blade. In the case of a blade joystick, control member interface element 4304 may comprise a plurality of metal contact area(s), such as a copper segment that can electrically communicate with housing components to initiate the activation of a motor, for example. Control member interface element 4304 is also adapted to communicate with a motor(s) and/or other actuators within the reusable housing to facilitate the robotic movement of the introducer (or other controllable medical device). In this manner, the control member on the disposable blade (or other disposable controller) controls the actuators (e.g., motor) within the re-usable housing.

FIG. 26 shows the disposable blade of FIG. 24 in place over the reusable housing of FIG. 25. Alternatively stated, a distal region of housing 4302 of the introducer assembly from FIG. 25 has been placed within cavity 4107 of blade 4102 in FIG. 24. All disclosure from FIGS. 23, 24 and 25 is incorporated by reference into the disclosure of FIG. 26. In this position, joystick 4202 is in operational (in this case electrical) communication with control member interface element 4304 of the housing 4302 (not visible) and indirectly and ultimately with the motor(s) and/or other controller mechanisms that are adapted to cause the robotic control the introducer/scope. The blade in FIG. 23 (or any other disposable blade herein) may also be used and positioned as shown in FIG. 26. In that example, the operational communication between the control member interface element and the control member on the blade is a hall sensor or magnetic communication, rather than an electrical communication. But as set forth herein, other types of sensors may be used to create the operable communication between the disposable controller and the reusable housing or body. FIG. 26 also illustrates introducer housing 1744 (which is descried in more detail herein) reliably coupled to housing 4302. While not shown, an introducer may be coupled to housing 1744. Coupling housing 1744 (and the introducer) to housing 4302 creates operable and controllable communication between the one or more actuators in 4302 (e.g., motor) and the introducer, which allows for the robotic controllable movement of the introducer upon user actuation of the control member(s) of the disposable blade.

Figure 27:
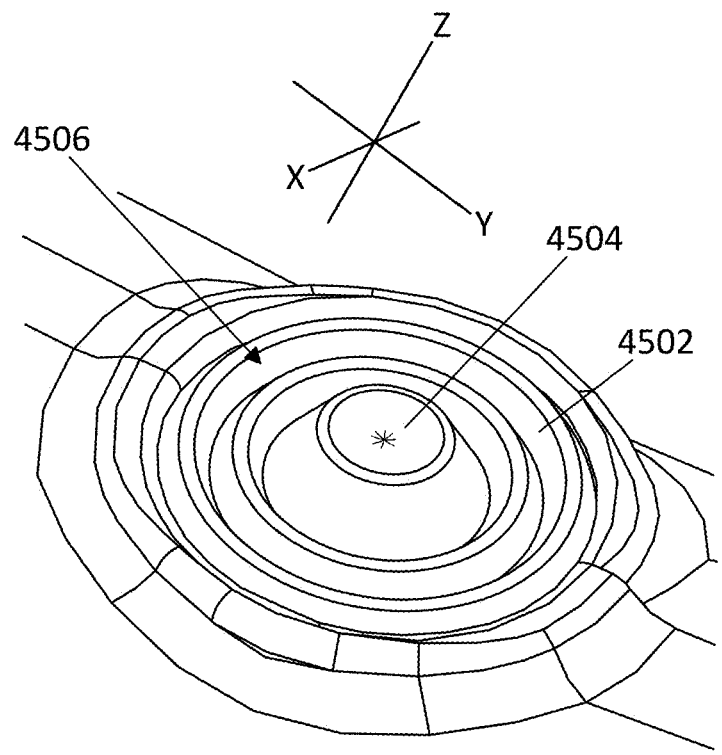
FIGS. 27, 28 and 29 show detail of an exemplary hall sensor magnet interface.
Figure 28:
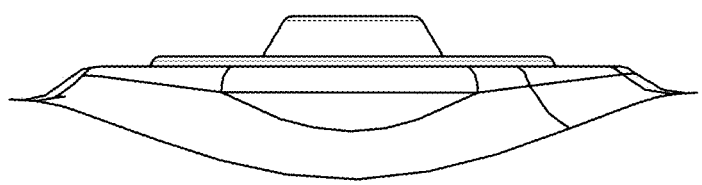
Figure 29:
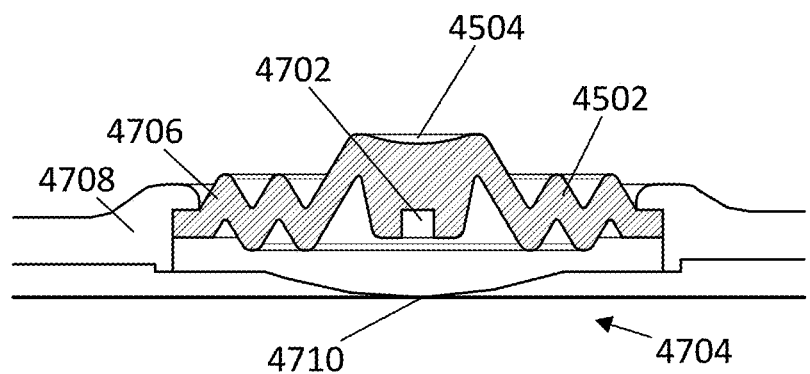

FIGS. 27, 28 and 29 show details of a merely exemplary interface between a disposable control member that includes a magnet and a reusable control member interface element that includes a hall sensor. This may be referred to herein as a hall sensor magnet interface. FIG. 27 illustrates only a portion of disposable controller (e.g., blade) shown in FIG. 23, including a control member that includes a flexible member 4506, which in this example includes ridges 4502 formed therein. Flexible member 4506 may include a flexible material such as silicone (or other flexible sterilizable material). Ridges 4502 or other means allow the user to move contact 4504 in any direction. A magnet 4702 is embedded in or coupled to the flexible member 4506, or under centerpiece 4504, and the movement of the magnet by the user is sensed by the hall sensor on the reusable introducer assembly housing, which then controls the actuators that control the robotic movement of the introducer. The contact 4504 may be moved in any direction laterally (in the x and/or y directions) as well as optionally in the z direction. For example, the x and y directions may control introducer scope articulation while the z direction may control the introducer scope distal advancement/proximal retraction.

FIG. 28 shows a side view of the control member (of the disposable controller) that is shown in the perspective view of FIG. 27.

FIG. 29 shows a cross sectional view of the hall sensor-magnet interface after the introducer assembly housing has been positioned within the cavity of the disposable blade. The interface includes flexible member 4706 (with ridges 4502), contact 4504 as well as magnet 4702. The magnet is moved by the user, which facilitates robotic control of the introducer. As the magnet moves, its movement/position is sensed by a hall sensor within housing 4704, the output of which controls the one or more introducer actuators (e.g., motor(s). Flexible member 4706 interfaces with blade extension 4708 to form a sterile barrier. Control member interface 4710 is the interface (which may be a contact or non-contact interface) between the disposable blade portion control member and the re-usable handle portion control member interface element.

Figure 30:
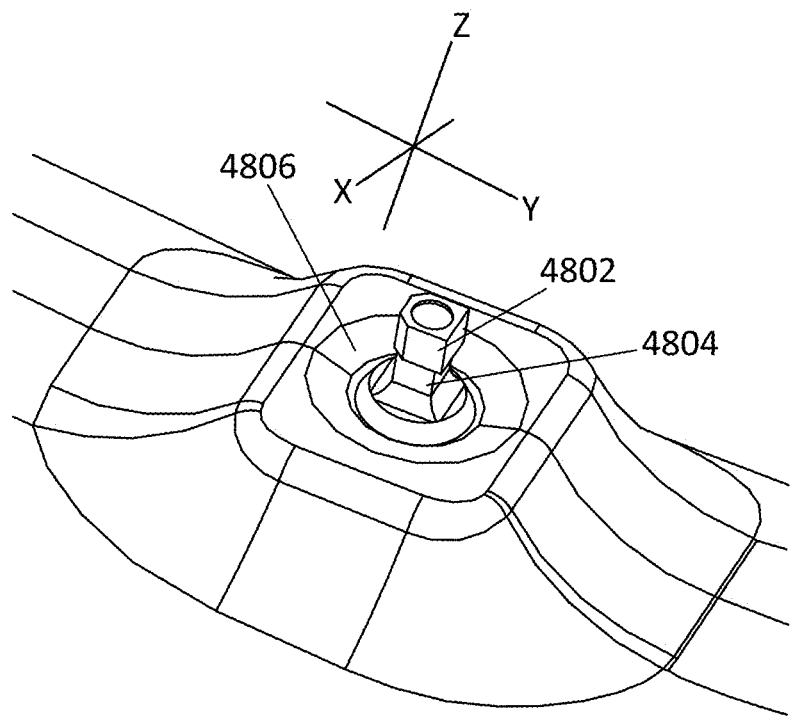
FIGS. 30, 31 and 32 show details of an exemplary joystick, which may be part of a disposable blade or other disposable controller.
Figure 31:
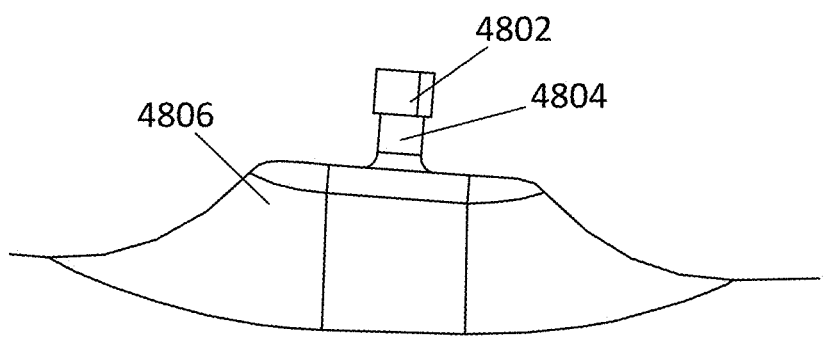
Figure 32:
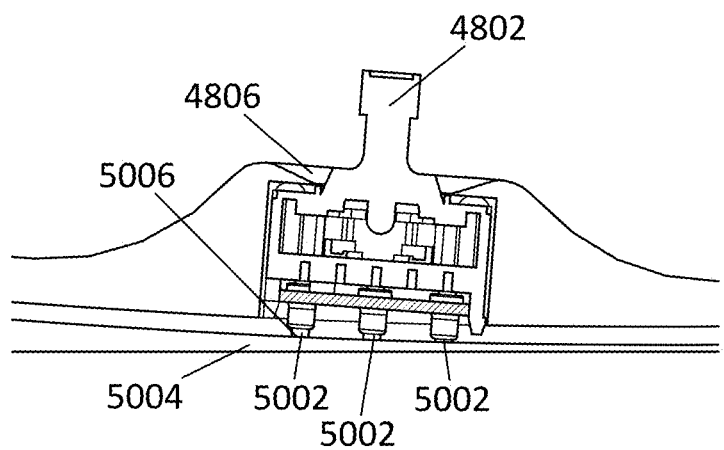

FIGS. 30, 31 and 32 show details of exemplary control member and interface that includes joystick 4202. Any relevant disclosure from any other example herein may be incorporated by reference into the disclosure of FIGS. 30-32.

FIG. 30 illustrates a merely exemplary control member that includes joystick 4802, including joystick shaft 4804. Also shown is joystick enclosure 4806. Joystick enclosure allows the user to move the joystick 4802 in any direction. Electrical contacts, such as pogo pins, are under joystick 4802, and the movement of the joystick by the user is communicated to one or more metal components on the reusable housing, which then communicate and control the introducer actuator(s) that controls the robotic movement of the introducer (or other controllable medical device). The joystick may be moved in any direction laterally (in the x and/or y directions) as well as optionally in the z direction. For example, the x and y directions may control introducer scope articulation while the z direction may control the introducer scope advancement/retraction.

FIG. 31 shows a side view of the control member (including a joystick) that is shown in the perspective view of FIG. 30.

FIG. 32 shows a cross sectional view of an interface, including the joystick shown in FIGS. 30 and 31. FIG. 32 illustrates joystick 4802, as well as electrical connectors 5002. The electrical connectors contact one or more metal (such as copper) components in reusable housing 5004. The joystick is actuated (in this case moved) by the user to robotically control the movement of the introducer scope. As the joystick is moved, electrical signals are transmitted to the reusable introducer assembly housing through the metal components. These signals are communicated (directly or indirectly) to the motor(s) and/or other actuators in the reusable housing to cause and control the movement of the introducer in one or directions (e.g., x, y, and/or z). Joystick enclosure 4806 interfaces with blade extension area 4708 to form a sterile barrier. Control member interface 5006 is the interface between the disposable portion (in this case a disposable blade) and the re-usable portion. In some embodiments, the joystick may be completely below a flexible sterile barrier.

In any of the embodiments herein, the at least one control member may be adapted to have at least first and second control modes, which may optionally be used to switch between x/y movement control, and a second mode that is adapted only for z movement control (forward/backward). For example only, a joystick may comprise a top button that is adapted to, if in an "up" state, be depressed once and stay depressed (in a down state), or if in a down/depressed state, can be pushed to cause it to return to the up state. Depending on the state of the button (or other actuator), the control member movement (e.g., joystick) will cause either x/y movement or z movement. For example only, if the button is in a first state (e.g., up), it will cause x/y movement, and if the button is in a second state (e.g., down), it will cause z movement (or vice versa). A joystick is used as an example only, and other control members can be adapted to have different states that cause different types of movement.

In some embodiments, the one or more control members of the disposable controller is incorporated or integrated into a rigid disposable blade. In some embodiments, the sterile barrier comprises both a rigid portion, for example the integrated blade and the blade extension (which are optionally at least partially unitary (the same component)), and a flexible portion, for example an area of flexible material (e.g., silicone or other flexible material) immediately surrounding the control member. In some embodiments, the control member interface is on the handheld system, not remote to the system. In some embodiments, the sterile barrier is primarily rigid, so that the user may operate the control member directly on the sterile barrier to control the introducer scope, with minimal or no substantial movement of the control member area with respect to the handle. In some embodiments, the blade, including the blade extension incorporating the control member, is adapted to snaps into place (mechanical integration) with the introducer assembly housing. This connection/coupling may be rigid, without significant play or movement between the two components. The user may control the system by placing their hand(s) directly on the system, in some instances, within the sterile field. In other words, the control member that controls the articulation/advancement/retraction of the introducer scope, is on the device that is rigidly connected to the introducer scope. This may allow the system to be operable with a single hand, which is described in more detail herein.

In alternative examples, the re-usable portion (e.g., any of the reusable introducer assemblies herein) optionally includes a screen or display, and the disposable controller (e.g., any of the disposable blades with controller(s) herein) may optionally be sized and configured to cover at least a portion of the screen. The interface facilitates a user actuating the disposable controller (rather than the screen directly) so the screen need not be cleaned in between patients/uses. In these alternative examples, the interface can be configured with capacitive or resistive touch capabilities.

Although some examples herein describe and show a disposable control member that is part of a laryngoscope blade (alternatively stated—a disposable blade that includes at least one control member), similar or other disposable controllers can be incorporated and used with other devices/systems, such as, for example without limitation, colonoscopes, bronchoscopes, esophageal scopes, articulating laparoscopes, other endoscopes, articulating surgical tools, feeding tube systems, articulating catheters, laparoscopic devices, bone surgery devices, any handheld controllable device, any controllable device, other devices that may be used in such procedures, etc. Existing systems and devices may need to be modified to be controllable via a disposable controller. The system and devices may be rigid or flexible, or partially rigid and partially flexible. For example only, any device/method of use that includes an articulating camera (e.g., colonoscopy, esophageal scope, uretero scope, intra-uterine or similar scope, hysteroscopy, etc.).

The disposable controller concepts herein may optionally be utilized in the field of single port laproscopy, which it typically performed either with a large robot (e.g., da Vinci systems) or small hand tools, which may be uncomfortable to use. The disposable controller concepts herein can be incorporated and used with hand-held robots or a set of handheld robotic tools such as graspers, scissors, etc. There are many robotic tools that can benefit from being partially disposable and partially reusable.

Figure 33:
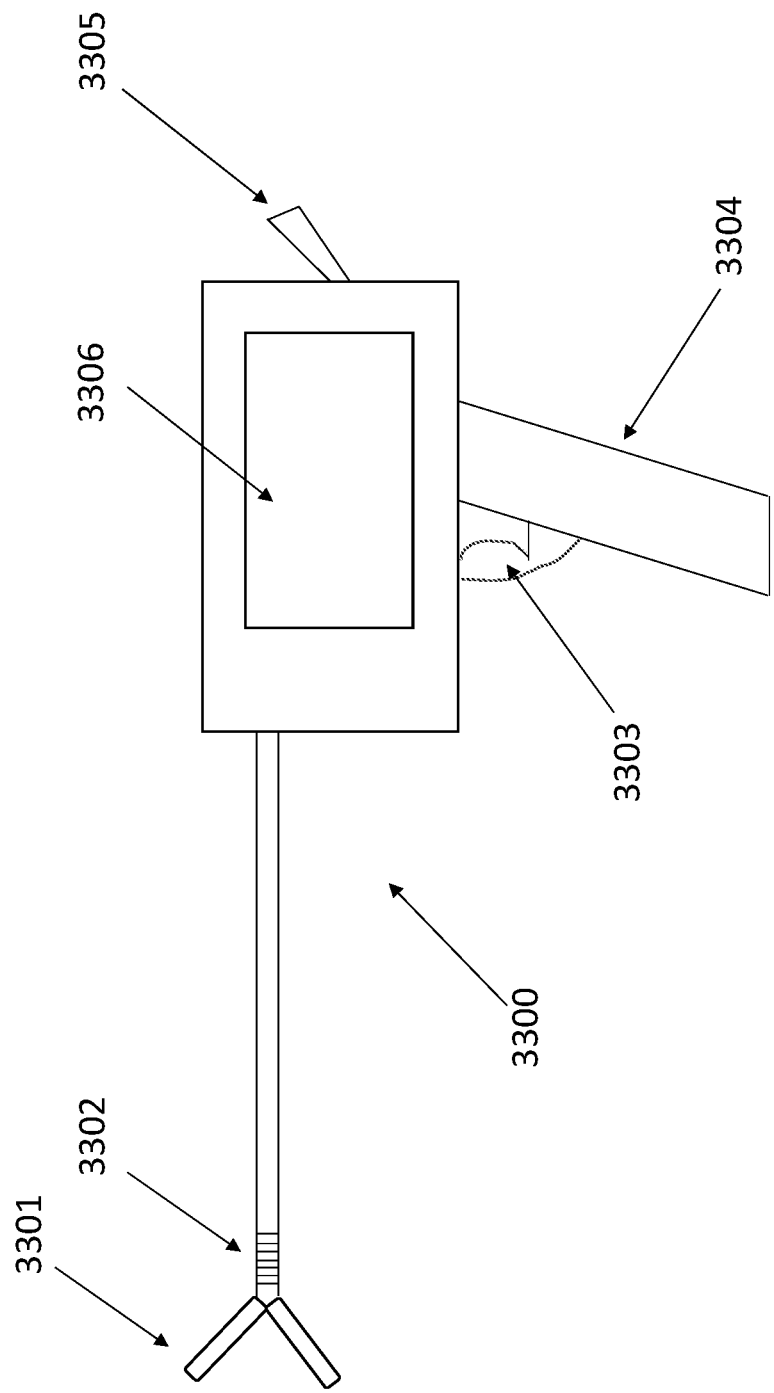
FIG. 33 illustrates an exemplary medical system that includes a reusable portion and a disposable portion including one or more control members.

FIG. 33 illustrates a merely exemplary laproscopy handheld robotic system 3300 that includes a portion that is reusable and a portion intended to be disposable. In this example, the system 3300 includes a tool end 3301, which may include, for example only, one or more of graspers, scissors, camera, etc. System 3300 also includes an optional articulating shaft section 3302, handle 3304, optional control member 3303, which in this examples is a trigger and/or button controls, optional control member 3305, which in this example is a joystick and/or additional controls, and reusable electronics 3306. All but electronics 3306 may be adapted to be disposed, while the more expensive electronics are re-usable. Alternatively, one or more parts of the shaft are optionally also re-usable. System 3300 can be adapted so the electronics 3306 can be uncoupled from the disposable parts to facilitate their re-use. The optional trigger, joystick, button(s) and/or other actuatable control members may be in operative communication with the tool section and/or the articulating section 3302 of the shaft.

In any of the embodiments herein, the interface between the at least one control member and the control member interface element may comprise a mechanical interface or communication. For example only, the disposable controller may comprise a button, that when user-actuated pushes against a button on the reusable portion, causing and controlling at least part of the reusable portion, which may include a robotically controllable medical device, to be actuated.

In any of the embodiments herein, the interface between the at least one control member and the control member interface element may comprise an optical interface or communication. For example only, any of the control members are optionally configured as or similar to a track-ball, wherein optical sensors sense the position/movement of the control member.

As a variant on the concepts herein, with any of the systems that include a disposable controller, the disposable controller may instead be re-usable. In these variants, the portion with the controller is adapted to be sterilizable, especially by harsh methods like autoclave. This approach can keep the electronics/optics safe, while the patient contacting part(s) can get cleaned. An exemplary precedent for this is battery packs for orthopedic drills and saws.

In some embodiments, a portion of the control member is disposable, and a portion is re-usable. For example, a portion of the control member may be on the disposable blade, and a portion of the control member may be on the re-usable handle. The control member is the user interface which controls the motor(s) and/or mechanisms in the introducer assembly housing, which in turn control the introducer scope articulations and/or advancement/retraction. In some embodiments, the entire control member is disposable.

The invention claimed is:

1. An intubation system, comprising:
a disposable blade that includes
a distal region sized and configured to be positioned in a mouth,
an extension that extends from the distal region, and which is configured and sized to be handheld,
the extension comprising at least one control member that is adapted to be manually actuated by an operator, and a cavity;
a reusable introducer assembly ("assembly"), at least a portion of which is sized and configured to be disposed in the cavity, the assembly including
at least one control member interface element that is adapted to be disposed in the cavity, positioned to be in operable communication with the at least one control member and responsive to the manual actuation of the at least one control member when at least a portion of the assembly is disposed in the cavity,
an ETT introducer ("introducer"), and
at least one introducer actuator in operable communication with the at least one control member interface element and in operable communication with the introducer to cause controlled robotic motion of the introducer in at least one direction of motion in response to user actuation of the at least one control member.

2. The system of claim 1, wherein the at least one control member interface element is adapted and positioned to sense one or more of motion, proximity, positioning, velocity, acceleration, or current.

3. The system of claim 1, wherein the at least one control member comprises a magnet and the at least one control member interface element comprises a Hall sensor.

4. The system of claim 1, wherein the at least one control member includes a joystick, and the at least one control member interface element comprises one or more metal contact surfaces.

5. The system of claim 1, wherein the at least one control member and the at least one control member interface element are in at least one of electrical, magnetic, mechanical or optical operable communication.

6. The system of claim 1, wherein the at least one control member comprises a flexible material.

7. The system of claim 1, wherein the extension comprises a rigid material.

8. The system of claim 1, wherein the at least one control member comprises a rigid, movable material.

9. The system of claim 8, wherein the at least one control member comprises a movable joystick.

10. The system of claim 1, wherein the at least one control member comprises one or more pogo pins.

11. The system of claim 1, wherein the assembly includes a housing that comprises the at least one control member interface element and the at least one introducer actuator, and
wherein the introducer is adapted to be releasably coupled to the housing to facilitate operable communication between the at least one introducer actuator and the introducer when the introducer is releasably coupled to the housing.

12. The system of claim 1, wherein the disposable blade comprises an endotracheal tube side channel separate and spaced from the cavity.

13. The system of claim 1, wherein the at least one introducer actuator comprises a motor.

14. The system of claim 1, wherein the at least one control member is operable in a first mode and a second mode, wherein when in the first mode, actuation of the control member causes a first type of motion of the introducer, and when in the second mode, actuation of the control member causes a second type of motion of the introducer.

15. The system of claim 14, wherein when in the first mode, actuation of the control member causes introducer motion in the x/y directions, and when in the second mode, actuation of the control member causes introducer motion in the z direction.

16. The system of claim 14, wherein the at least one control member includes a pressable button, and wherein the at least one control member is in the first mode when the pressable button is in a first state and in the second mode when the pressable button is in a second state.

17. An intubation system, comprising:
a disposable blade that includes
a distal region sized and configured to be positioned in a mouth, an extension that extends from the distal region, and which is configured and sized to be handheld,
the extension including at least one control member that is adapted to be manually actuated by an operator, and a cavity; and
a reusable housing, at least a portion of which is sized and configured to be disposed in the cavity of the disposable blade, the reusable housing including:
at least one control member interface element that is adapted to be disposed in the cavity, positioned to be in operable communication with the at least one control member and responsive to the manual actuation of the at least one control member when at least a portion of the reusable housing is disposed in the cavity, and
at least one endotracheal tube introducer actuator in operable communication with the at least one control member interface element and adapted to be in operable communication with an endotracheal tube introducer to cause controlled robotic motion of the introducer in at least one direction of motion in response to user actuation of the at least one control member,
wherein the disposable blade does not comprise an introducer actuator that causes controlled robotic motion of the introducer.

18. The system of claim 17, wherein the at least one control member interface element is adapted and positioned to sense one or more of motion, proximity, positioning, velocity, acceleration, or current.

19. The system of claim 17, wherein the at least one control member comprises a magnet and the at least one control member interface element comprises a Hall sensor.

20. The system of claim 17, wherein the at least one control member includes a joystick, and the at least one control member interface element comprises one or more metal contact surfaces.

21. The system of claim 17, wherein the at least one control member and the at least one control member interface element are in at least one of electrical, magnetic, mechanical or optical operable communication.

22. The system of claim 17, wherein the at least one control member comprises a flexible material.

23. The system of claim 17, wherein the extension comprises a rigid material.

24. The system of claim 17, wherein the at least one control member comprises a rigid, movable material.

25. The system of claim 24, wherein the at least one control member comprises a movable joystick.

26. The system of claim 17, wherein the at least one control member comprises one or more pogo pins.

27. The system of claim 17, further comprising an endotracheal tube introducer that is adapted to be releasably coupled to the reusable housing to facilitate operable communication between the at least one introducer actuator and the introducer when the endotracheal tube introducer is releasably coupled to the reusable housing.

28. The system of claim 17, wherein the disposable blade comprises an endotracheal tube side channel separate and spaced from the cavity.

29. The system of claim 17, wherein the at least one introducer actuator comprises a motor.

30. The system of claim 17, wherein the at least one control member is operable in a first mode and a second mode, wherein when in the first mode, actuation of the control member causes a first type of motion of the introducer, and when in the second mode, actuation of the control member causes a second type of motion of the introducer.

31. The system of claim 30, wherein when in the first mode, actuation of the control member causes introducer motion in the x-y directions, and when in the second mode, actuation of the control member causes introducer motion in the z direction.

32. The system of claim 30, wherein the at least one control member includes a pressable button, and wherein the at least one control member is in the first mode when the pressable button is in a first state and in the second mode when the pressable button is in a second state.

33. An intubation system, comprising:
a disposable blade that includes
a distal region sized and configured to be positioned in a mouth, an extension that extends from the distal region, and which is configured and sized to be handheld,
the extension including at least one control member that is adapted to be manually actuated by an operator, and a cavity; and
a reusable housing, at least a portion of which is sized and configured to be disposed in the cavity of the disposable blade, the reusable housing including:
at least one control member interface element that is positioned to be disposed within the cavity, in close proximity to the at least one control member, and directly responsive to manual actuation of the at least one control member when the at least one control member interface element is disposed in the cavity, and
at least one endotracheal tube introducer actuator in operable communication with the at least one control member interface element and adapted to be in operable communication with an endotracheal tube introducer to cause controlled robotic motion of the introducer in at least one direction of motion in response to user actuation of the at least one control member.

34. An intubation system, comprising:
a disposable blade that includes
a distal region sized and configured to be positioned in a mouth,
an extension that extends from the distal region, and which is configured and sized to be handheld,
at least one control member that is adapted to be manually actuated by an operator, and an internal cavity defined at least by a portion of the disposable blade, wherein the portion of the disposable blade completely surrounds the internal cavity; and a reusable housing, at least a portion of which is sized and configured to be disposed in the internal cavity of the disposable blade, the reusable housing including:

at least one control member interface element that is adapted to be disposed in the internal cavity, positioned to be in operable communication with the at least one control member and responsive to the manual actuation of the at least one control member when at least a portion of the assembly is disposed in the internal cavity, and at least one endotracheal tube introducer actuator in operable communication with the at least one control member interface element and adapted to be in operable communication with an endotracheal tube introducer to cause controlled robotic motion of the introducer in at least one direction of motion in response to user actuation of the at least one control member.

\* \* \* \* \*